United States Patent
Emanuele et al.

(10) Patent No.: US 10,501,577 B2
(45) Date of Patent: *Dec. 10, 2019

(54) POLOXAMER COMPOSITION FREE OF LONG CIRCULATING MATERIAL AND METHODS FOR PRODUCTION AND USES THEREOF

(71) Applicant: LifeRaft Biosciences, Inc., Mt. Pleasant, SC (US)

(72) Inventors: R. Martin Emanuele, San Diego, CA (US); Mannarsamy Balasubramanian, Roswell, GA (US); Stewart V. Smith, San Diego, CA (US)

(73) Assignee: LifeRaft Biosciences, Inc., Mt. Pleasant, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/207,441

(22) Filed: Jul. 11, 2016

(65) Prior Publication Data

US 2017/0002141 A1    Jan. 5, 2017

Related U.S. Application Data

(63) Continuation of application No. 14/793,670, filed on Jul. 7, 2015, now Pat. No. 9,403,941.

(60) Provisional application No. 62/021,697, filed on Jul. 7, 2014.

(51) Int. Cl.

| | |
|---|---|
| *A61K 31/77* | (2006.01) |
| *A61K 35/14* | (2015.01) |
| *A61K 35/19* | (2015.01) |
| *A61K 9/00* | (2006.01) |
| *C08G 65/30* | (2006.01) |
| *C08G 65/08* | (2006.01) |
| *A61K 35/18* | (2015.01) |
| *A61K 35/12* | (2015.01) |

(52) U.S. Cl.
CPC .......... *C08G 65/30* (2013.01); *A61K 9/0019* (2013.01); *A61K 31/77* (2013.01); *A61K 35/14* (2013.01); *A61K 35/18* (2013.01); *A61K 35/19* (2013.01); *C08G 65/08* (2013.01); *A61K 2035/124* (2013.01); *C08G 2650/58* (2013.01)

(58) Field of Classification Search
CPC ..... A61K 9/0019; A61K 35/14; C08G 65/008
See application file for complete search history.

(56) References Cited

U.S. PATENT DOCUMENTS

| | | | |
|---|---|---|---|
| 4,522,811 A | 6/1985 | Eppstein et al. | 514/2 |
| 4,801,452 A | 1/1989 | Hunter | 424/94.63 |
| 4,837,014 A | 6/1989 | Hunter et al. | 424/78 |
| 4,873,083 A | 10/1989 | Hunter et al. | 424/83 |
| 4,879,109 A | 11/1989 | Hunter | 424/83 |
| 4,897,263 A | 1/1990 | Huter | 424/83 |
| 4,937,070 A | 6/1990 | Hunter | 424/83 |
| 4,997,644 A | 3/1991 | Hunter | 424/83 |
| 5,017,370 A | 5/1991 | Hunter | 424/83 |
| 5,028,599 A | 7/1991 | Hunter | 424/83 |
| 5,030,448 A | 7/1991 | Hunter | 514/83 |
| 5,032,394 A | 7/1991 | Hunter | 424/83 |
| 5,039,520 A | 8/1991 | Hunter | 424/83 |
| 5,041,288 A | 8/1991 | Hunter | 424/83 |
| 5,047,236 A | 9/1991 | Hunter | 424/83 |
| 5,064,643 A | 11/1991 | Hunter | 424/83 |
| 5,071,649 A | 12/1991 | Hunter | 424/83 |
| 5,078,995 A | 1/1992 | Hunter | 424/83 |
| 5,080,894 A | 1/1992 | Hunter | 424/83 |
| 5,089,260 A | 2/1992 | Hunter | 424/83 |
| 5,182,106 A | 1/1993 | Nezrow | |
| 5,523,492 A | 6/1996 | Emanuele et al. | 568/606 |
| 5,554,372 A | 9/1996 | Hunter | 424/280.1 |
| 5,567,859 A | 10/1996 | Emanuele et al. | 568/624 |
| 5,605,687 A | 2/1997 | Lee | 424/78.06 |
| 5,622,649 A | 4/1997 | Hunter et al. | 252/309 |
| 5,648,071 A | 7/1997 | Hunter et al. | 424/78.31 |
| 5,674,911 A | 10/1997 | Emanuele et al. | 514/723 |
| 5,691,387 A | 11/1997 | Emanuele et al. | 568/723 |
| 5,696,298 A | 12/1997 | Emanuele et al. | 568/623 |
| 5,800,711 A | 9/1998 | Reeve et al. | 210/639 |
| 5,811,088 A | 9/1998 | Hunter et al. | 424/78.08 |
| 5,885,590 A | 3/1999 | Hunter et al. | 424/280.1 |
| 5,990,241 A | 11/1999 | Emanuele et al. | 525/88 |
| RE36,665 E | 4/2000 | Emanuele et al. | 568/624 |

(Continued)

FOREIGN PATENT DOCUMENTS

| | | |
|---|---|---|
| EP | 0 682 946 | 7/2000 |
| WO | 92/16484 | 10/1992 |

(Continued)

OTHER PUBLICATIONS

Letter/Written Disclosure of the Supplemental Information Disclosure Statement for the above-referenced application, filed herewith Sep. 9, 2015, 2 pages.
Response, filed Aug. 17, 2015, to International Search Report and Written Opinion, dated Dec. 2, 2014, in connection with International Patent Application No. PCT/US2014/060982, 34 pages.
Letter/Written Disclosure of the Supplemental Information Disclosure Statement for the above-referenced application, filed herewith Aug. 17, 2015, 2 pages.
Spurney et al., "Membrane sealant Poloxamer P188 protects against Isoproterenol induced Cardiomyopathy in Dystrophin Deficient mice," BMC Cardiovascular Disorders 11:20, 10 pages (2011).

(Continued)

*Primary Examiner* — Alma Pipic
(74) *Attorney, Agent, or Firm* — Burr & Forman LLP; Douglas L. Lineberry

(57) ABSTRACT

Provided herein are long circulating material free (LCMF) poloxamer compositions and uses thereof. In particular, provided are LCMF poloxamer 188 compositions and uses thereof. Also provided are supercritical fluid extraction (SFE) methods and high pressure (subcritical) methods for preparing poloxamer compositions, particularly the LCMF poloxamer compositions.

29 Claims, 11 Drawing Sheets

(56) References Cited

U.S. PATENT DOCUMENTS

| | | | |
|---|---|---|---|
| RE37,285 E | 7/2001 | Emanuele et al. | 514/723 |
| 6,359,014 B1 | 3/2002 | Emanuele et al. | 514/723 |
| 6,448,371 B1 | 9/2002 | Berg et al. | 528/486 |
| 6,747,064 B2 | 6/2004 | Emanuele et al. | 514/44 |
| RE38,558 E | 7/2004 | Emanuele et al. | 568/623 |
| 6,761,824 B2 | 7/2004 | Reeve et al. | 210/639 |
| 6,844,001 B2 | 1/2005 | Balasubramanian et al. | 424/280.1 |
| 6,977,045 B2 | 12/2005 | Reeve et al. | 210/639 |
| 7,045,576 B2 | 5/2006 | Balasubramanian et al. | 525/242 |
| 7,846,426 B2 | 12/2010 | Metzger et al. | 424/78.38 |
| 8,133,918 B2 | 3/2012 | Zhang et al. | 514/731 |
| 8,137,677 B2 | 3/2012 | Hunt et al. | 424/234.1 |
| 8,372,387 B2 | 2/2013 | Markham et al. | 424/78.31 |
| 8,460,644 B2 | 6/2013 | Meadows et al. | 424/70.15 |
| 8,512,695 B2 | 8/2013 | Austen | 424/93.7 |
| 8,580,245 B2 | 11/2013 | Metzger et al. | 424/78.38 |
| 9,403,941 B2 * | 8/2016 | Emanuele | |
| 9,757,411 B2 * | 9/2017 | Emanuele et al. | |
| 9,757,441 B2 * | 12/2017 | Lin | |
| 2002/0183398 A1 | 12/2002 | Emanuele et al. | 514/44 |
| 2003/0206910 A1 | 11/2003 | Nicol et al. | 514/44 |
| 2004/0258718 A1 | 12/2004 | Meadows et al. | 424/70.15 |
| 2005/0095221 A1 | 5/2005 | Balasubramanian et al. | 424/78.38 |
| 2006/0013883 A1 | 1/2006 | Nicol et al. | 514/44 |
| 2006/0078616 A1 | 4/2006 | Georgewill et al. | 424/489 |
| 2006/0121016 A1 | 6/2006 | Lee et al. | 424/94.1 |
| 2007/0237740 A1 | 10/2007 | Reddington et al. | 424/78.38 |
| 2008/0260681 A1 | 10/2008 | Metzger et al. | 424/78.38 |
| 2008/0269449 A1 | 10/2008 | Chattopadhyay et al. | 526/329.7 |
| 2009/0214685 A1 | 8/2009 | Hunt et al. | 424/239.1 |
| 2009/0246162 A1 | 10/2009 | Markham et al. | 424/400 |
| 2009/0254104 A1 | 10/2009 | Murray | |
| 2010/0031066 A1 | 2/2010 | Geiger et al. | 424/497 |
| 2010/0087501 A1 | 4/2010 | Mehta et al. | 424/486 |
| 2010/0104542 A1 | 4/2010 | Austen | 424/93.7 |
| 2010/0178269 A1 | 7/2010 | Markham et al. | 424/78.18 |
| 2010/0183519 A1 | 7/2010 | Katz et al. | 424/9.2 |
| 2010/0249240 A1 | 9/2010 | Meadows et al. | 424/70.15 |
| 2010/0316590 A1 | 12/2010 | Kayed | 424/78.37 |
| 2011/0008266 A1 | 1/2011 | Tamarkin et al. | 424/43 |
| 2011/0033412 A1 | 2/2011 | Ng et al. | 424/78.3 |
| 2011/0044935 A1 | 2/2011 | Metzger et al. | 424/78.38 |
| 2011/0212047 A1 | 9/2011 | Hunter et al. | 424/78.17 |
| 2012/0141619 A1 | 6/2012 | Hunt et al. | 424/234.1 |
| 2012/0277199 A1 | 11/2012 | Ye et al. | 424/400 |
| 2013/0129662 A1 | 5/2013 | Markham et al. | 424/78.31 |
| 2013/0177524 A1 | 7/2013 | Emanuele et al. | 424/78.31 |
| 2014/0056839 A1 | 2/2014 | Zhang et al. | 424/78.06 |
| 2015/0030559 A1 | 1/2015 | Ng et al. | 424/78.3 |
| 2015/0093368 A1 | 4/2015 | Emanuele et al. | 424/78.31 |
| 2015/0190421 A1 | 7/2015 | Markham et al. | 424/78.3 |

FOREIGN PATENT DOCUMENTS

| | | |
|---|---|---|
| WO | WO 1994/08596 | 4/1994 |
| WO | WO 2006/044738 | 4/2006 |
| WO | WO 2006/037031 | 6/2006 |
| WO | WO 2006/091941 | 8/2006 |
| WO | WO 2008/016640 | 2/2008 |
| WO | WO 2009/023177 | 2/2009 |
| WO | WO 2012/068079 | 5/2012 |
| WO | WO 2012/091361 | 5/2012 |
| WO | WO 2015/058013 | 4/2015 |

OTHER PUBLICATIONS

Culley, B., "MAST Therapeutics, Inc.," presented at Canaccord Genuity 34th Annual Growth Conference on Aug. 14, 2014. Presentation. 32 pages.

Culley, B., "MAST Therapeutics, Inc.," presented at the Rodman and Renshaw 16th Annual Global Investment Conference on Sep. 9, 2014. Presentation. 32 pages.

International Search Report and Written Opinion, dated Aug. 19, 2014, in connection with International Patent Application No. PCT/US2014/045627, 12 pages.

Written Opinion, dated Jan. 16, 2015, in connection with International Patent Application No. PCT/US2014/045627, 7 pages.

International Search Report and Written Opinion, dated Dec. 2, 2014, in connection with International Patent Application No. PCT/US2014/060982, 15 pages.

Mast Therapeutics Press Release Feb. 4, 2015, "Mast Therapeutics Announces Initiation of Phase 2a Studies of AIR001 in Patients With Heart Failure With Preserved Ejection Fraction (HFpEF)," [online][retrieved on Feb. 9, 2015] retrieved from <URL:mast-therapeutics.com/investors/news/?releaseid=2013429>, 3 pages.

Letter/Written Disclosure of the Information Disclosure Statement for the above-referenced application, filed herewith Aug. 13, 2015, 2 pages.

Adams et al., "Experimental evaluation of pluronic F68 (A non-ionic detergent) as a method of diminishing systemic fat emboli resulting from prolonged cardiopulmonary bypass," Surg. Forum 10:585-589 (1960).

Adams-Graves et al., "RheothRx (Poloxamer 188) injection for the acute painful episode of Sickle Cell Disease: A pilot study," Blood 90:2041-2046 (1997).

Armstrong et al., "Modulation of red blood cell aggregation and blood viscosity by the covalent attachment of pluronic copolymers," Biorheology 38:239-247 (2001).

Ballas et al. "Safety of purified poloxamer 188 in sickle cell anemia phase I study of a non-ionic surfactant in the management of acute chest syndrome," Hemoglobin 28(2):85-102 (2004).

Bentley et al., "Purification of Pluronic F-68 for perfluorochemical emulsification," J Pharmacy and Pharmacology 41(9):661-663 (1988).

Cappel, M. and J. Kreuter, "Effect of nonionic surfactants on transdermal drug delivery: II. Poloxamer and poloxamine surfactants," Int J Pharm 69:155-167 (1991).

Carr et al., "Abnormal fibrin structure and inhibition of fibrinolysis in patients with multiple myeloma," J Lab Clin Med 128(1):83-88 (1996).

Chang et al., "Prolonged antifungal effects of clotrimazole-containing mucoadhesive thermosensitive gels on vaginitis," J. Controlled Rel. 82:39-50 (2002).

Chang et al., "Peselectivity of the glomerular capillary wall to macromolecules. II. Experimental studies in rats using neutral dextran," Biophys J 15(9):887-906 (1975).

Choi et al., "In situ gelling and mucoadhesive liquid suppository containing acetaminophen: enhanced bioavailability," Int J Pharm. 165:23-32 (1998).

Danielson et al., "Use of Pluronic F-68 to diminish fat emboli and hemolysis during cardiopulmonary bypass. A controlled clinical study," J Thorac Cardiovasc Surg. 59(2):178-184 (1970).

Desai et al., "Evaluation of selected micronized poloxamers as tablet lubricants," Drug Deliv. 14(7):413-426 (2007).

Emanuele, M. and Balasubramaniam, B. "Differential effects of commercial-grade and purified Poloxamer 188 on renal function," Drugs in R&D 14(2):73-83 (2014). Available online at :<URL:springer.com/article/10.1007/s40268-014-0041-0.

Emanuele, M. "FLOCOR: a new anti-adhesive, rheologic agent," Expert Opin Investig Drugs 7(7):1193-1200 (1998).

Frim et al., "The surfactant poloxamer-188 protects against glutamate toxicity in the rat brain," Neuro Report. 15:171-174 (2004).

Gibbs, W. and T. Hagemann, "Purified poloxamer 188 for sickle cell vaso-occlusive crisis," Ann. Pharmacother. 38(2):320-324 (2004).

Grindel et al., "Distribution, metabolism, and excretion of a novel surface-active agent, purified poloxamer 188, in rats, dogs, and humans," J. of Pharmaceutical Sciences 90(9): 1936-1947 (2002).

Grindel et al., "Pharmacokinetics of a novel surface-active agent, purified poloxamer 188, in rat, rabbit, dog and man," Biopharm. Drug Dispos. 23: 87-103 (2002).

(56) References Cited

OTHER PUBLICATIONS

Hoppensteadt et al., "Effect of purified poloxamer 188 and various dextrans on erythrocyte sedimentation rate in healthy subjects and patients with sickle cell disease," FASEB J.28(1):suppl. 1139.6, 1 page (2014).

Hunter et al., "Poloxamer 188 inhibition of ischemia/reperfusion injury: evidence for a novel anti-adhesive mechanism," Ann Clin Lab Sci. 40(2):115-125 (2010).

Isaac et al., "Acute repair of chondrocytes in the rabbit tibiofemoral joint following blunt impact using P188 surfactant and a preliminary investigation of its long-term efficacy," J Orthop Res. (4):553-558 (2010).

IUPAC_IUB Commission on Biochemical Nomenclature Biochem. 11:1726-1731 (1972).

Jeong et al., "Thermosensitive sol-gel reversible hydrogels," Adv Drug Del Rev, 54(1):37-51 (2002).

Jewell et al, "Pharmacokinetics of RheothRx injection in healthy male volunteers," J Pharm Sci 86(7):808-812 (1997).

Justicz et al., "Reduction of myocardial infarct size by poloxamer 188 and mannitol in a canine model," Am Heart J. 122(3 Pt 1):671-680 (1991).

Karmarkar, A., "Poloxamers and their applications" Pharmainfo.net Published Oct. 27, 2008; <URL:pharmainfo.net/pharma-student-magazine/poloxamers-and-their-applications-0, 31 pages.

Kerleta et al., "Poloxamer 188 supplemented culture medium increases the vitality of Caco-2 cells after subcultivation and freeze/thaw cycles," ALTEX. 27(3):191-197 (2010).

Lane, T. and V. Krukonis, "Reduction in the toxicity of a compound of an artificial blood substitute by supercritical fluid fractionation," Transfusion 28:375-378 (1988).

Lane, T. and G. Lamkin, "Paralysis of phagocyte migration due to an artificial blood substitute," Blood. 64:400-405 (1984).

Lee et al., "Surfactant-induced sealing of electropermeabilized skeletal muscle membranes in vivo," Proc. Natl. Acad. Sci. USA 89:4524-4528 (1992).

Mayer et al., "Effects of poloxamer 188 in a rabbit model of hemorrhagic shock," Ann Clin Lab Sci 24(4):302-311 (1994).

Moloughney, J. and N. Weisleder, "Poloxamer 188 (P188) as a membrane resealing reagent in biomedical applications," Recent Pat Biotechnol. 6(3):200-211 (2012).

Muzíková et al., "A study of micronized poloxamers as lubricants in direct compression of tablets," Acta Pol Pharm. 70(6):1087-1096 (2013).

O'Keefe et al., "Poloxamer-188 as an adjunct to primary percutaneous transluminal coronary angioplasty for acute myocardial infarction," Am. J. Cardiol. 78:747-750 (1996).

Orringer et al., "Purified poloxamer 188 for treatment of acute vaso-occlusive crisis of sickle cell disease: A randomized controlled trial," JAMA 286(17):2099-2106 (2001).

Paek et al., "Poloxamer 188 and propylene glycol-based rectal suppository enhances anticancer effect of 5-fluorouracil in mice," Biol Phar Bull 29:1060-1063 (2006).

Palmer et al., "The poloxamer 407-induced hyperlipidemic antherogenic animal model," Med Sci Sports Exerc 29(11):1416-1421 (1997).

Qi et al. "Development of a poloxamer analogs/carbopol-based in situ gelling and mucoadhesive ophthalmic delivery system for puerarin," Int. J. Pharm. 337:178-187 (2007).

Quinn et al., "Adjunctive use of the non-ionic surfactant Poloxamer 188 improves fetal dopaminergic cell survival and reinnervation in a neural transplantation strategy for Parkinson's disease," Eur J Neurosci. 27(1):43-52 (2008).

Reeve, L., "The Poloxamers: Their Chemistry and Medical Applications" in *Handbook of Biodegradable Polymers*, Domb et al., Eds., Harward Academic Publishers, OPA: Amsterdam, Chapter 12, pp. 232-249 (1997).

Schaer et al., "Reduction in reperfusion-induced myocardial necrosis in dogs by RhethRx injection (poloxamer 188 N.F.), a hemorheological agent that alters neurtrophil function," Circulation 90(6): 2964-2975 (1994).

Schmolka, J., "A review of block polymer surfactants," Am. Oil Chem. Soc. 54:110-116 (1977).

Weiner et al., "Liposome-collagen gel matrix: A novel sustained drug delivery system," J. Pharm Sci. 74(9): 922-925 (1985).

Yong et al, "Enhanced anti-tumor activity and alleviated hepatotoxicity of clotrimazole-loaded suppository using poloxamer-propylene glycol gel," Int. J. Pharm. 321:56-61 (2006).

Yong et al., "Preparation of ibuprofen-loaded liquid suppository using eutectic mixture system with menthol," Eur. J. Pharm. Sci. 23:347-353 (2004).

York et al., in: *Supercritical Fluid Technology for Drug Product Development*. (New York, Marcel Dekker, 2004), pp. 470-473.

Yun et al, "Development of a thermo-reversible insulin liquid suppository with bioavailability enhancement," Int. J. Pharm. 189:137-145 (1999).

MAST Therapeutics Press Release Jan. 6, 2014, "MAST Therapeutics Announces Positive Data in Model of Heart Failure," [online][retrieved on May 20, 2014] Retrieved from:<URL:masttherapeutics.com/investors/news/?releaseid=1887966>, 2 pages.

MAST Therapeutics Press Release Feb. 18, 2014, "MAST Therapeutics Announces Positive Data in Model of Heart Failure," [online][retrieved on May 20, 2014] Retrieved from:<URL:masttherapeutics.com/investors/news/?releaseid=1900672>, 3 pages.

Mast Therapeutics, "A Brief History of MST-188," [online][retrieved on May 20, 2014] Retrieved from <URL:sec.gov/Archives/edgar/data/1160308/000119312514192551/d725005dex991.htm>, 2 pages.

Mast Therapeutics Press Release Aug. 7, 2014, "Mast Therapeutics to present at the Canaccord Genuity 34th annual Growth Conference on Aug. 14," [online][retrieved on Aug. 20, 2014] Retrieved from <URL:masttherapeutics.com/investors/news/?releaseid=1956499>, 2 pages.

Mast Therapeutics Press Release Jun. 16, 2014, "Mast Therapeutics initiates sub-study within phase 3 epic trial," [online][retrieved on Aug. 20, 2014] Retrieved from <URL:masttherapeutics.com/investors/news/?releaseid=1939998>, 3 pages.

Mast Therapeutics Press Release Dec. 9, 2014, "Mast Announces Plans for Development of Vepoloxamer (MST-188) in Heart Failure," [online][retrieved on Dec. 9, 2014] Retrieved from <URL:masttherapeutics.com/investors/news/?releaseid=1996054>, 3 pages.

Mast Therapeutics Press Release Feb. 11, 2015, "Mast Therapeutics Announces New Data Supporting Vepoloxamer in Embolic Stroke," [online][retrieved on Feb. 11, 2015] Retrieved from <URL:masttherapeutics.com/investors/news/?releaseid=2015639>, 3 pages.

Mast Therapeutics Press Release Mar. 2, 2015, "Mast Announces Results From Nonclinical Study Investigating Repeat Treatment With Vepoloxamer in Advanced Heart Failure," [online][retrieved on Mar. 9, 2015] retrieved from <URL:masttherapeutics.com/investors/news/?releaseid=2021506>, 3 pages.

Mast Therapeutics Press Release Mar. 23, 2015, "Mast to Develop Vepoloxamer (MST-188) in Chronic Heart Failure," [online] Retrieved from <URL: masttherapeutics.com/investors/news/?releaseid=2027689 [retrieved on Mar. 24, 2015], 3 pages.

Moghimi et al., "Causative factors behind poloxamer 188 (Pluronic F68, Flocor)-induced complement activation in human sera. A protective role against poloxamer-mediated complement activation by elevated serum lipoprotein levels", Biochim Biophys Acta. Jun. 28, 2004;1689(2):103-13.

Schaer et al., "Beneficial effects of RheothRx injection in patients receiving thrombolytic therapy for acute myocardial infarction. Results of a randomized, double-blind, placebo-controlled trial", Circulation. Aug. 1, 1996;94(3):298-307.

Yusef et al., "Effects of RheothRx on mortality, morbidity, left ventricular function, and infarct Circulation. Jul. 1, 1997;96(1):192-201.size in patients with acute myocardial infarction. Collaborative Organization for RheothRx Evaluation (CORE)".

Related U.S. Appl. No. 14/793,662, filed Jul. 7, 2015.
Related U.S. Appl. No. 14/793,730, filed Jul. 7, 2015.
Related U.S. Appl. No. 13/783,158, filed Mar. 1, 2013.
Related U.S. Appl. No. 14/553,913, filed Nov. 25, 2014.

\* cited by examiner

POLOXAMER COMPOSITION FREE OF LONG CIRCULATING MATERIAL AND METHODS FOR PRODUCTION AND USES THEREOF

RELATED APPLICATIONS

The present application is a continuation of U.S. patent application Ser. No. 14/793,670, filed on Jul. 7, 2015, which claims the benefit of priority to U.S. Provisional Application Ser. No. 62/021,697, to R. Martin Emanuele and Mannarsamy Balasubramanian, filed Jul. 7, 2014, entitled "A POLOXAMER COMPOSITION FREE OF LONG CIRCULATING MATERIAL AND METHODS FOR PRODUCTION AND USES THEREOF."

This application is related to International PCT Application No. PCT/US2015/039418, to R. Martin Emanuele and Mannarsamy Balasubramanian, filed the same day herewith, and entitled "A POLOXAMER COMPOSITION FREE OF LONG CIRCULATING MATERIAL AND METHODS FOR PRODUCTION AND USES THEREOF."

This application also is related to U.S. Provisional Application Ser. No. 62/021,691, to R. Martin Emanuele, Santosh Vetticaden and Patrick Keran, filed Jul. 7, 2014, entitled "POLOXAMER THERAPY FOR HEART FAILURE;" to U.S. provisional application Ser. No. 62/126,400, to R. Martin Emanuele, Santosh Vetticaden and Patrick Keran, filed Feb. 27, 2015, entitled "POLOXAMER THERAPY FOR HEART FAILURE;" to International PCT Application No. PCT/US14/45627, to R. Martin Emanuele, Santosh Vetticaden and Patrick Keran, filed Jul. 7, 2014, entitled "POLOXAMER THERAPY FOR HEART FAILURE;" and this application also is related to International PCT Application No. PCT/US2015/039426 and U.S. application Ser. No. 14/793,662, each to R. Martin Emanuele, Santosh Vetticaden and Patrick Keran, each filed the same day herewith, and each entitled "POLOXAMER THERAPY FOR HEART FAILURE."

Where permitted, the subject matter of each application is incorporated by reference in its entirety.

FIELD OF THE INVENTION

Provided herein are a long circulating material free (LCMF) poloxamer composition and uses thereof. Also provided are supercritical fluid extraction (SFE) methods and high pressure (subcritical) methods for preparing the LCMF poloxamer compositions.

BACKGROUND

Certain polyoxypropylene/polyoxyethylene (POP/POE) copolymers, called poloxamers, have beneficial biological effects when administered to a human or animal. These copolymers have been used for treating circulatory diseases either alone or in combination with other compounds, including, for example, anticoagulants, free radical scavengers, anti-inflammatory agents, antibiotics, membrane stabilizers and perfusion media. Poloxamer 188 (P188) (see, e.g., U.S. Pat. No. 5,696,298) is useful for treating pathologic hydrophobic interactions in blood and other biological fluids of humans and animals. Commercially available preparations of poloxamers contain highly heterogeneous populations of molecules that vary widely in the size and configuration of the constituent molecules. The diversity of molecules present in the commercially available poloxamers can make prediction of the biological activity difficult and lead to unwanted biological activities. Hence, there is a need for alternative preparations of poloxamers.

SUMMARY

Provided herein are alternative poloxamer preparations and methods of making and using them. Provided are long circulating material free (LCMF) poloxamers, particularly LCMF poloxamer 188. The LCMF poloxamer, when administered to a subject, such as a human subject, does not result in material in the subject that has a significantly longer half-life than the main peak, such that, upon administration of the LCMF poloxamer to a subject, such as a human, the circulating half-life of all components in the distribution of the copolymer, is no more than 5.0-fold longer than the circulating half-life of the main component in the distribution of the co-polymer. Generally the half-life of all components in a human is less than 12 hours. Commercially available and prior preparations of poloxamer, such as poloxamer 188, have a long circulating material (LCM) that, when administered to a human, has a half life that is more than 5.0 fold the circulating half-life of the main component in the distribution of the copolymer. Also provided are methods of preparing the LCMF poloxamers and other poloxamers, including removal of low molecular weight impurities.

Among the LCMF poloxamers are LCMF poloxamer polyoxyethylene/polyoxypropylene copolymers that have the formula:

$HO(CH_2CH_2O)_a$—$[CH(CH_3)CH_2O]_b$—$(CH_2CH_2O)_{a'}H$, where: each of a and a' is an integer such that the percentage of the hydrophile ($C_2H_4O$) is between approximately or between 60% and 90% by weight of the total molecular weight of the copolymer; a and a' are the same or different; b is an integer such that the molecular weight of the hydrophobe ($C_3H_6O$) is between approximately 1,300 and 2,300 Daltons (Da); no more than 1.5% of the total components in the distribution of the co-polymer are low molecular weight components having an average molecular weight of less than 4,500 Da; no more than 1.5% of the total components in the distribution of the co-polymer are high molecular weight; components having an average molecular weight of greater than 13,000 Da; the polydispersity value of the copolymer is less than approximately 1.07 or less than 1.07, such as equal to or less than 1.06, 1.05, 1.04, 1.03 and 1.02; and the circulating half-life of all components in the distribution of the co-polymer, when administered to a subject, is no more than 5.0-fold longer than the circulating half-life of the main component in the distribution of the co-polymer. The LCMF poloxamer is more hydrophilic than the preparations of poloxamer 188 known in the art, such as the poloxamer described in U.S. Pat. No. 5,696,298, and commercially available preparations thereof, which contain long circulating material (LCM).

Provided is a long circulating material free (LCMF) poloxamer 188, where: the LCMF poloxamer 188 is a polyoxyethylene/polyoxypropylene copolymer that has the formula $HO(CH_2CH_2O)_a$—$[CH(CH_3)CH_2O]_b$—$(CH_2CH_2O)_{a'}H$; each of a and a' is an integer such that the percentage of the hydrophile ($C_2H_4O$) is between approximately 60% and 90% by weight of the total molecular weight of the copolymer; a and a' are the same or different; b is an integer such that the molecular weight of the hydrophobe ($C_3H_6O$) is between approximately 1,300 and 2,300 Daltons; no more than 1.5% of the total components in the distribution of the co-polymer are low molecular weight components having an average molecular weight of less than 4,500 Daltons; no more than 1.5% of the total components in the distribution of the co-polymer are high molecular weight components having an average molecular weight of greater than 13,000 Daltons; the polydispersity value of the copolymer is less than approximately 1.07 or less than 1.07, such as, 1.06, 1.05, 1.04 or 1.03, or less than 1.06, 1.05, 1.04 or 1.03; and following intravenous administration to a human subject, the circulating plasma half-life of any components not comprising the main peak is no more than 5.0-fold longer than the circulating half-life of the main component in the distribution of the copolymer.

Included are embodiments in which all components comprising the polymeric distribution of the co-polymer, have a circulating half-life in the plasma of the subject, such as a human subject, that is no more than 5.0-fold or 4.0-fold, or 3.0-fold longer than the circulating half-life of the main component of the co-polymer following intravenous administration to a subject. For example, all components in the distribution of the co-polymer, when administered to a human subject, have a circulating half-life in the plasma of the subject that is no more than 4-fold longer than the circulating half-life of the main component in the distribution of the co-polymer. Included are embodiments in which all components in the distribution of the co-polymer, when administered to a human subject, have a half-life in the plasma of the subject that is no more than 30 hours, 25 hours, 20 hours, 15 hours, 12 hours, 10 hours, 9 hours, 8 hours or 7 hours, such as 10 or 12 hours. The LCMF poloxamer, thus, does not include LCM.

Provided herein is a long circulating material free (LCMF) poloxamer 188, where: the LCMF poloxamer 188 is a polyoxyethylene/polyoxypropylene copolymer that has the formula $HO(CH_2CH_2O)_a$—$[CH(CH_3)CH_2O]_b$—$(CH_2CH_2CHO)_aH$; each of a and a' is an integer such that the percentage of the hydrophile ($C_2H_4O$) is between approximately 60% and 90% by weight of the total molecular weight of the copolymer; a and a' are the same or different; b is an integer such that the molecular weight of the hydrophobe ($C_3H_6O$) is between approximately 1,300 and 2,300 Daltons; no more than 1.5% of the total components in the distribution of the co-polymer are low molecular weight components having an average molecular weight of less than 4,500 Daltons; no more than 1.5% of the total components in the distribution of the co-polymer are high molecular weight components having an average molecular weight of greater than 13,000 Daltons; the polydispersity value of the copolymer is less than approximately 1.07 or less than 1.07; and the LCMF poloxamer is more hydrophilic than a purified poloxamer 188 that contains the long circulating material (LCM), whereby the circulating half-life of all components in the distribution of the copolymer, is no more than 5.0-fold longer than the circulating half-life of the main component in the distribution of the co-polymer.

Provided is a long circulating material free (LCMF) poloxamer 188, where: the LCMF poloxamer 188 is a polyoxyethylene/polyoxypropylene copolymer that has the formula $HO(CH_2CH_2O)_a$—$[CH(CH_3)CH_2O]_b$—$(CH_2CH_2O)_aH$; each of a and a' is an integer such that the percentage of the hydrophile ($C_2H_4O$) is between approximately 60% and 90% by weight of the total molecular weight of the copolymer; a and a' are the same or different; b is an integer such that the molecular weight of the hydrophobe ($C_3H_6O$) is between approximately 1,300 and 2,300 Daltons; no more than 1.5% of the total components in the distribution of the co-polymer are low molecular weight components having an average molecular weight of less than 4,500 Daltons; no more than 1.5% of the total components in the distribution of the co-polymer are high molecular weight components having an average molecular weight of greater than 13,000 Daltons; the polydispersity value of the copolymer is less than approximately 1.07 or less than 1.07; and the LCMF has a mean retention time ($t_R$) as assessed by reverse phase-high performance liquid chromatography that is shorter than purified poloxamer 188 that contains LCM. In some embodiments, for example, the RP-HPLC conditions are such that the mean $t_R$ of the LCM-containing poloxamer 188 is about or is 9.9-10; and the mean $t_R$ of the LCMF poloxamer is about or is 8.7-8.8.

Provided is a long circulating material free (LCMF) poloxamer 188, where: the LCMF poloxamer 188 is a polyoxyethylene/polyoxypropylene copolymer that has the formula $HO(CH_2CH_2O)_a$—$[CH(CH_3)CH_2O]_b$—$(H_2CH_2O)_a$ H; each of a and a' is an integer such that the percentage of the hydrophile ($C_2H_4O$) is between approximately 60% and 90% by weight of the total molecular weight of the copolymer; a and a' are the same or different; b is an integer such that the molecular weight of the hydrophobe ($C_3H_6O$) is between approximately 1,300 and 2,300 Daltons; no more than 1.5% of the total components in the distribution of the co-polymer are low molecular weight components having an average molecular weight of less than 4,500 Daltons; no more than 1.5% of the total components in the distribution of the co-polymer are high molecular weight components having an average molecular weight of greater than 13,000 Daltons; the polydispersity value of the copolymer is less than approximately 1.07 or less than 1.07; and the capacity factor (k') as assessed by RP-HPLC is less than the k' for purified LCM-containing poloxamer 188 under the same conditions. For example, the RP-HPLC conditions are such that the mean k' of the LCMF poloxamer is about or is 3.2-3.3, and that of the LCM-containing poloxamer 188 is about or is 3.6-3.7.

In embodiments herein, the LCMF poloxamer can be a poloxamer with a hydrophobe having a molecular weight of about 1,400 to 2,000 Daltons (Da) or 1,400 to 2,000 Da, such as, for example, 1,750 Da, and a hydrophile portion constituting approximately 70% to 90% or 70% to 90% by weight of the copolymer. The LCMF poloxamer can have an average molecular weight of 7,680 to 9,510 Daltons, such as 8,400-8,800 Daltons.

In some embodiments, the percentage of high molecular weight components in the preparation greater than 13,000 Daltons constitute less than 1% of the total distribution of components of the poloxamer preparation. In some embodiments, following intravenous administration to a human subject, the LCMF poloxamer does not result in a component with a circulating half-life greater than four-fold that of the circulating plasma half-life of the main peak. In some embodiments the percentage of high molecular weight components in the preparation greater than 13,000 Daltons constitutes less than 0.9%, 0.8%, 0.7%, 0.6%, 0.5% or less of the total distribution of components of the poloxamer preparation.

The LCMF poloxamers differ from the LCM-containing poloxamers in that, when administered to a subject, all components clear within a shorter time than the components of an LCM-containing poloxamer as described and shown throughout the disclosure herein. When characterized by RP-HPLC the LCMF poloxamers provided herein are such that the mean k' and the mean $t_R$ are less than the corresponding LCM-containing poloxamer. The LCMF poloxamers are more hydrophilic than the corresponding LCM-containing poloxamer.

Provided are LCMF poloxamers that are produced by supercritical fluid extraction methods, including those described herein. For example, provided are LCMF poloxamers produced by methods comprising: a) introducing a poloxamer solution into an extractor vessel, wherein the poloxamer is dissolved in a first alkanol to form a solution; b) admixing the poloxamer solution with an extraction solvent comprising a second alkanol and supercritical carbon dioxide under a temperature and pressure to maintain the supercritical carbon dioxide for a first defined period, where: the temperature is above the critical temperature of carbon dioxide but is no more than 40° C.; the pressure is 220 bars to 280 bars; and the alkanol is provided at an alkanol concentration that is 7% to 8% by weight of the total extraction solvent; and c) increasing the concentration of the second alkanol in step b) in the extraction solvent a plurality of times in gradient steps over time of the extraction method, where: each plurality of times occurs for a further defined period; and in each successive step, the alkanol concentration is increased 1-2% compared to the previous concentration of the second alkanol; and d) removing the extraction solvent from the extractor vessel to thereby remove the extracted material from the raffinate poloxamer preparation.

In some embodiments for producing LCMF poloxamers, in a), the ratio of poloxamer to first alkanol, by weight is about or is from 2:1 to 3:1, inclusive; and/or the plurality of times in step c) occurs in two, three, four or five gradient steps; and/or step c) can be performed in two steps comprising: i) increasing the concentration of the second alkanol from about 7% to 8% to about 8.2% to 9.5% for a second defined period; and ii) increasing the concentration of the second alkanol from about 8.2% to 9.5% to about 9.6% to 11.5% for a third defined period. In particular embodiments, the LCMF poloxamer is produced by a method where:

the alkanol concentration in step b) is about or is 7.4% by weight;

the alkanol concentration in step i) is about or is 9.1% by weight; and the alkanol concentration in step ii) is about or is 10.7% by weight.

The first defined period, second defined period and third defined period each can be performed for 2 hours to 12 hours; the defined periods can be the same or different. For example, the first defined period can be performed for 2 hours to 6 hours; the second defined period for 2 hours to 6 hours; and the third defined period for 4 hours to 10 hours. In the methods by which the LCMF poloxamer is produced the first and second alkanol are each independently selected from among methanol, ethanol, propanol, butanol, pentanol and a combination thereof. For example, the first and second alkanol can be the same or different, such as the first alkanol is methanol and the second alkanol is methanol or a different alkanol. Step d), where the extracted material is removed, can occur throughout steps b) and c). The method can be practiced, for example as a batch method or as a continuous method.

In embodiments herein, the LCMF poloxamer produced by the method is an LCMF poloxamer 188. Also provided are the methods for producing LCMF poloxamers, including the LCMF poloxamer 188 as described above and throughout the disclosure.

Provided are compositions containing the LCMF poloxamers provided herein. The compositions can be pharmaceutical compositions formulated in a pharmaceutically acceptable vehicle. In particular, provided are compositions, and pharmaceutical compositions containing or comprising the LCMF poloxamers provided herein. Provided are compositions comprising the LCMF poloxamer 188. Provided is a composition, comprising an a long circulating free (LCMF) poloxamer 188, where: the composition is formulated for intravenous administration; and the composition comprises 5-50 gm of the LCMF poloxamer. The LCMF poloxamer can be any LCMF poloxamer including any provided herein. Uses of the compositions and methods of treatment of any disease or disorder or condition for which poloxamers are administered are provided. Exemplary diseases and conditions, include, but are not limited to, heart failure, myocardial infarction, limb ischemia, shock, stroke, ischemic stroke, sickle cell disease, neurodegenerative diseases, macular degeneration, diabetic retinopathy and congestive heart failure. The diseases disorders and conditions, include acute heart failure and chronic heart failure, acute myocardial infarction, acute limb ischemia and acute stroke.

The LCMF poloxamer compositions can be used for other disorders, conditions, diseases and uses, including, but not limited to, treating disorders treated by membrane resealing and repair; treating tissue ischemia and reperfusion injury; reducing inflammatory responses; reducing blood viscosity; facilitating thrombolysis; promoting or maintaining hemostasis; as a vehicle for drug, nucleic acid or protein delivery; as an emulsifier to stabilize suspensions of hydrophobic drugs; cleansing skin wounds; as a surfactant in the formulation of cosmetics; to treat storage lesion compromised blood or prevent storage lesion in blood and blood products; to control the viscosity of personal care products and soaps; as a laxative and other uses known to those of skill in the art.

The compositions containing the LCMF poloxamer can be formulated in or contain blood, red blood cells and/or blood products, such as packed red blood cells. Such compositions can be used for transfusions. Transfusions are used in treatments for diseases that include, but are not limited, to sickle cell disease, acute chest syndrome, peripheral artery disease, heart failure, stroke, peripheral vascular disease, macular degeneration, acute respiratory distress syndrome (ARDS), multiple organ failure, ischemia, shock, acidosis, hypothermia, anemic decompensation, surgery, trauma, blood loss and blood disorders; and any treatment that comprises transfusion. These include hemorrhagic shock, septic shock and acute blood loss. Hence also provided are uses of the compositions for transfusions, and methods of treatment by administering a composition to a subject who has a disease or disorder selected from among sickle cell disease, acute chest syndrome, peripheral artery disease, heart failure, stroke, peripheral vascular disease, macular degeneration, acute respiratory distress syndrome (ARDS), multiple organ failure, ischemia, shock including hemorrhagic shock and septic shock, acidosis, hypothermia, anemic decompensation, surgery, trauma, acute blood loss and blood disorders, where treatment comprises transfusion.

The LCMF poloxamers can be prepared by any method in which the LCM is removed. These methods include the described methods for preparing, including, but not limited to, methods for preparing an LCMF poloxamer 188 or any poloxamer of choice, such as described below, by a method that includes the steps of: a) introducing a poloxamer 188 solution into an extractor vessel, wherein the poloxamer is dissolved in a first alkanol to form a solution; b) admixing the poloxamer solution with an extraction solvent comprising a second alkanol and a supercritical liquid under a temperature and pressure to maintain the supercritical liquid, where the concentration of the second alkanol in the extraction solvent is increased over time of the extraction method; and c) removing the extraction solvent from the extractor vessel to thereby remove the extracted material from the poloxamer preparation to thereby produce an LCMF poloxamer.

The methods include a method of preparing a long circulating free (LCMF) poloxamer, comprising: a) introducing a poloxamer 188 solution into an extractor vessel, wherein the poloxamer is dissolved in a first alkanol to form a solution; b) admixing the poloxamer solution with an extraction solvent comprising a second alkanol and supercritical carbon dioxide under a temperature and pressure to maintain the supercritical carbon dioxide for a first defined period, where: the temperature is above the critical temperature of carbon dioxide but is no more than 40° C.; the pressure is 220 bars to 280 bars; and the alkanol is provided at an alkanol concentration that is 7% to 8% by weight of the total extraction solvent; c) increasing the concentration of the second alkanol in step b) in the extraction solvent a plurality of times in gradient steps over time of the extraction method; each plurality of times occurs for a further defined period; and in each successive step, the alkanol concentration is increased 1-2% compared to the previous concentration of the second alkanol; and removing the extraction solvent from the extractor vessel to thereby remove the extracted material from the raffinate poloxamer preparation to thereby produce the LCMF poloxamer.

In some embodiments, step d) in which the extracted material is removed can be performed throughout steps b) and c). As described above, in step a), the ratio of poloxamer to first alkanol, by weight can be about or is from 2:1 to 3:1, inclusive; and/or the plurality of times in step c) occurs in two, three, four or five gradient steps. Step c) can be performed in two steps comprising: i) increasing the concentration of the second alkanol from about 7% to 8% to about 8.1% to 9.5% for a second defined period; and ii) increasing the concentration of the second alkanol from about 8.2% to 9.5% to about 9.6% to 11.5% for a third defined period. In a particular embodiment, the alkanol concentration in step b) is about or is 7.4% by weight; the alkanol concentration in step i) is about or is 9.1% by weight; and/or the alkanol concentration in step ii) is about or is 10.7% by weight. The first defined period, second defined period and third defined period each can be performed for 2 hours to 12 hours; and the defined periods can be the same or are different. For example, the first defined period can be carried out for 2 hours to 6 hours; the second defined period can be carried out for 2 hours to 6 hours; and the third defined period can be carried out for 4 hours to 10 hours. The first and second alkanol each can be independently selected from among methanol, ethanol, propanol, butanol, pentanol and a combination thereof. Each can be the same or different, for example, the first alkanol can be methanol and/or the second alkanol can be methanol.

Provided are extraction methods for preparing the LCMF poloxamers, that include the steps of: a) charging a poloxamer into an extractor vessel and dissolving the poloxamer in a first alkanol to form a solution; b) admixing an extraction solvent comprising a second alkanol and a supercritical liquid under pressure with the solution to form an extraction mixture, wherein the concentration of the second alkanol in the extraction solvent is increased over the time of extraction method; and c) removing the extraction solvent from the extractor vessel to thereby remove the low molecular weight substances from the poloxamer. In some embodiments the method comprises a) charging a poloxamer into an extractor vessel and dissolving the poloxamer in a first solvent to form a solution, wherein the first solvent is selected from the group consisting of alcohols, aliphatic ketones, aromatic ketones, amines, and mixtures thereof; b) admixing an extraction solvent with the solution to form an extraction mixture, wherein the extraction solvent comprises high-pressure carbon dioxide and the first solvent, wherein the concentration of the solvent in the extraction solvent is increased over the time of extraction method; and c) removing the extraction solvent from the extractor vessel to thereby remove the low molecular weight impurities from the poloxamer. In embodiments of the methods, after step c, the method further can include repeating steps b and c.

The poloxamers used in the methods described herein can be any poloxamer, including, but not limited to poloxamer 188, poloxamer 331 and poloxamer 407. As described above, for all of the methods, the first and the second alkanol are each independently selected from among methanol, ethanol, propanol, butanol, pentanol and a combination thereof. For example, one or both alkanols can be methanol. In all methods provided herein, the supercritical liquid under pressure can be any suitable supercritical liquid, such as, but not limited to, carbon dioxide, methane, ethane, propane, ammonia and freon. In particular embodiments, the supercritical liquid under pressure is carbon dioxide. In embodiments of the methods for preparing the LCMF poloxamer, such as the LCMF poloxamer 188, the extraction solvent comprises methanol and carbon dioxide. Exemplary of ratios of methanol to carbon dioxide is 1:100 to about or 15:100, such as 2:100 to about or 10:100. The ratio of methanol to carbon dioxide can be increased over the course of performing the method. The methods herein include batch methods and continuous methods. In an exemplary embodiment of practicing the methods, the extractor vessel can be pressurized in a range of 125 to 500 bars, such as a range of 25 to 100 bars, or 200 bars to 400 bars or 280 bars to 340 bars. The temperature of the extractor vessel can be 10° C. to 80° C. In embodiments of the methods, the second alkanol can be provided as a percentage (w/w) of the total extraction solvent that is 3% to 20% or 3% to 15%.

In step b) of the above described methods, the concentration of the second alkanol in step b) in the extraction solvent can be increased a plurality of times in gradient steps over time of the extraction method, where: each plurality of times occurs for a further defined period; and in each successive step, the alkanol concentration is increased, for example, by 1-2%, compared to the previous concentration of the second alkanol; and removing the extraction solvent from the extractor vessel to thereby remove the extracted material from the raffinate poloxamer preparation.

In other embodiments, the methods for purifying the LCMF poloxamer, can include the steps of: a) introducing a poloxamer solution into an extractor vessel, wherein the poloxamer is dissolved in a solvent to form a solution, where the solvent is selected from among alcohols, aliphatic ketones, aromatic ketones, amines, and mixtures thereof; b) admixing the poloxamer solution with an extraction solvent comprising a solvent and high-pressure carbon dioxide, wherein the concentration of the solvent in the extraction solvent is increased over the time of extraction method; and c) removing the extraction solvent from the extractor vessel to thereby remove the extracted material from the poloxamer to produce the LCMF poloxamer. The solvent in step a) can be methanol. The extraction solvent can comprise methanol and carbon dioxide. Extracted material includes low molecular weight impurities less than 4,500 Daltons. The methods, including those described above, and exemplified herein, can produce an LCMF poloxamer, particularly an LCMF poloxamer having the properties as described throughout the disclosure herein, including the poloxamer that is a polyoxyethylene/polyoxypropylene copolymer that has the formula HO(CH$_2$CH$_2$O)$_a$—[CH(CH$_3$)CH$_2$O]$_b$—(CH$_2$CH$_2$O)$_a$H, where: each a or a' is an integer such that the percentage of the hydrophile (C$_2$H$_4$O) is between approximately 60% and 90% by weight of the total molecular weight of the copolymer; a and a' are the same or different; and b is an integer such that the molecular weight of the hydrophobe (C$_3$H$_6$O) is between approximately 1,300 and 2,300 Daltons. The resulting poloxamer is an LCMF poloxamer that does not have the LCM material as described herein. such as a poloxamer LCMF 188, where: the LCMF poloxamer 188 is a polyoxyethylene/polyoxypropylene copolymer that has the formula HO(CH$_2$CH$_2$O)$_a$—[CH(CH$_3$)CH$_2$O]$_b$—(CH$_2$CH$_2$CHO)$_a$H; each of a and a' is an integer such that the percentage of the hydrophile (C$_2$H$_4$O) is between approximately 60% and 90% by weight of the total molecular weight of the copolymer; a and a' are the same or different; b is an integer such that the molecular weight of the hydrophobe (C$_3$H$_6$O) is between approximately 1,300 and 2,300 Daltons; no more than 1.5% of the total components in the distribution of the co-polymer are low molecular weight components having an average molecular weight of less than 4,500 Daltons; no more than 1.5% of the total components in the distribution of the co-polymer are high molecular weight components having an average molecular weight of greater than 13,000 Daltons; the polydispersity value of the copolymer is less than approximately 1.07 or less than 1.07; and the poloxamer does not include the LCM material so that, when administered to a subject, such as a human, the circulating half-life of all components in the distribution of the copolymer, is no more than 5.0-fold longer than the circulating half-life of the main component in the distribution of the co-polymer. The resulting LCMF poloxamer, such as an LCMF poloxamer 188, is more hydrophilic than the corresponding LCM-containing poloxamer, such as a purified LCM-containing poloxamer 188. The resulting LCMF poloxamer, has a lower average $t_R$ and a lower k' than the corresponding LCM-containing poloxamer when assessed under the same appropriate conditions on RP-HPLC, such as those exemplified and described herein.

Also provided are methods of confirming or identifying that the resulting poloxamer is an LCMF poloxamer. These methods include, for example, testing the LCMF poloxamer on RP-HPLC and comparing the material to the starting material and/or to a standard known to contain the LCM, or assessing the hydrophilicity of the poloxamer and comparing it to the starting material and/or to a standard known to contain the LCM material.

BRIEF DESCRIPTION OF THE DRAWINGS

The drawings described herein are for illustrative purposes only of selected embodiments and not all possible implementations, and are not intended to limit the scope of the present disclosure.

DETAILED DESCRIPTION

Figure 1:
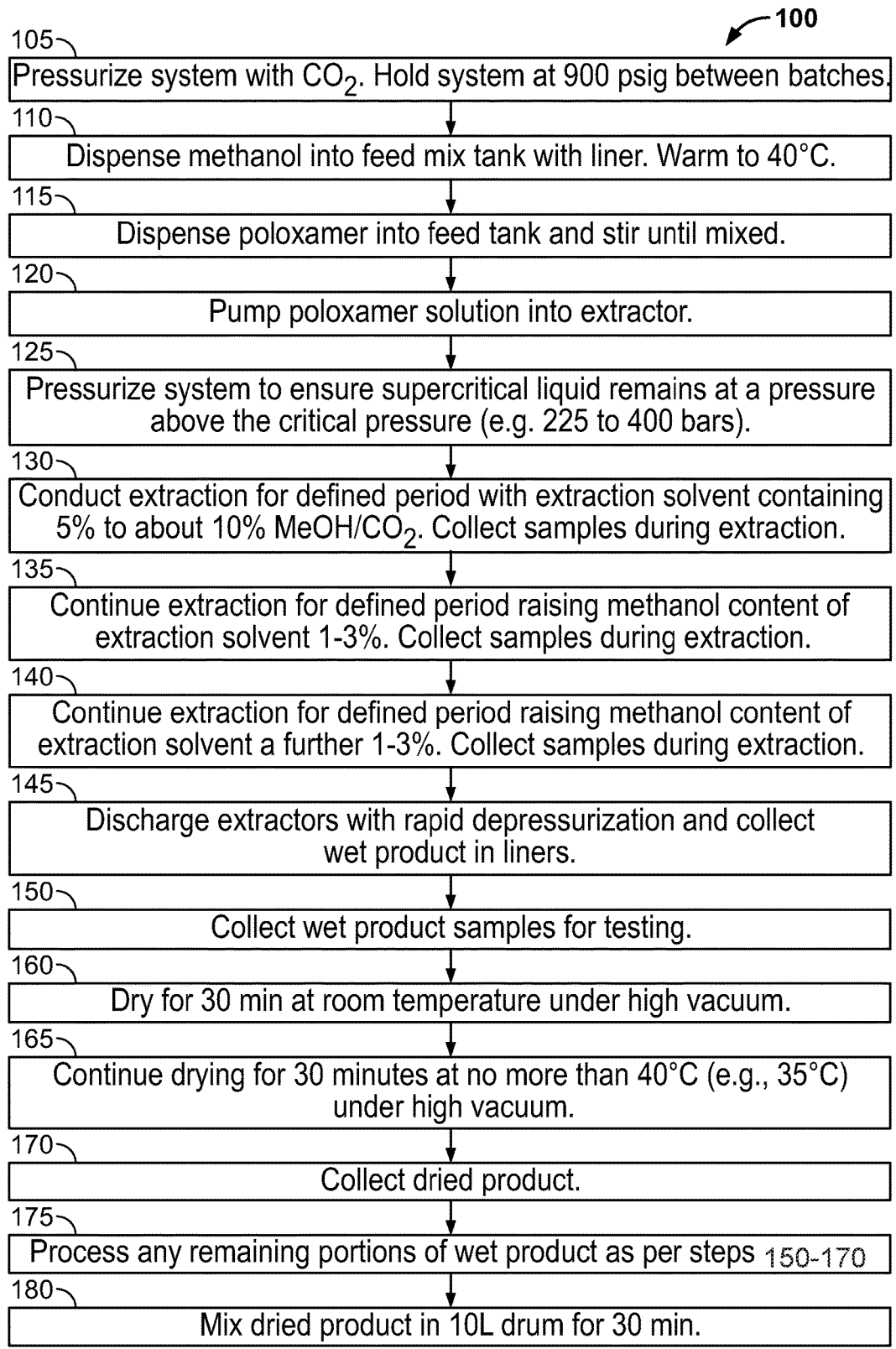
FIG. 1 is a general process 100 for supercritical fluid extraction (SFE) of a poloxamer.

Outline
A. DEFINITIONS
B. MOLECULAR DIVERSITY OF POLOXAMERS, POLOXAMER 188, LCM-CONTAINING POLOXAMER 188 AND LCMF POLOXAMERS
  1. Poloxamers
  2. Poloxamer 188
  3. Molecular Diversity of Poloxamer 188
    a. Low Molecular Weight Components
    b. Components Resulting in Long Circulating Half-Life
C. LONG CIRCULATING MATERIAL FREE (LCMF) POLOXAMER
D. EXTRACTION METHODS FOR PURIFYING POLOXAMERS
  1. Process for Extraction
    a. Supercritical Methods
    b. High Pressure Methods
  2. Extraction Vessel and System
  3. Extraction and Removal of Extractants
  4. Exemplary Methods for preparation of purified poloxamers
    a. Removal of Low Molecular Weight (LMW) Components
    b. Preparation of Long Circulating Material Free (LCMF) poloxamer
  5. Methods for Confirming the Identity of LCMF Poloxamers E. PHARMACEUTICAL COMPOSITIONS AND FORMULATIONS
  1. Formulations
  2. Dosage
  3. Dosages and Administration
F. METHODS AND THERAPEUTIC USES OF POLOXAMER 188 AND LCMF P188
G. EXAMPLES Definitions Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, poloxamers are synthetic block copolymers of ethylene oxide and propylene oxide. A "polyoxyethylene/poloxypropylene copolymer," "PPC" or "poloxamer" refers to a block copolymer containing a central block of polyoxypropylene (POP) flanked on both sides by blocks of polyoxyethylene (POE) having the following chemical formula:

$$HO(C_2H_4O)_{a'}-[C_3H_6O]_b-(C_2H_4O)_aH$$

where: a' and a can be the same or different and each is an integer such that the hydrophile portion represented by ($C_2H_4O$) (i.e. the polyoxyethylene portion of the copolymer) constitutes approximately 60% to 90% by weight of the copolymer, such as 70% to 90% by weight of the copolymer; and b is an integer such that the hydrophobe represented by $(C_3H_6O)_b$ (i.e., the polyoxypropylene portion of the copolymer) has a molecular weight of approximately 950 to 4,000 Daltons (Da), such as about 1,200 to 3,500 Da, for example, 1,200 to 2,300 Da, 1,500 to 2,100 Da, 1,400 to 2,000 Da or 1,700 to 1,900 Da. For example, the molecular weight of the hydrophile portion can be between 5,000 and 15,000 Da. Exemplary poloxamers having the general formula described above include poloxamers wherein a or a' is an integer 5-150 and b is an integer 15-75, such as poloxamers wherein a is an integer 70-105 and b is an integer 15-75. Poloxamers include poloxamer 188 (e.g., those sold under the trademarks Pluronic® F-68, Flocor®, Kolliphor® and Lutrol®).

The nomenclature of the polyoxyethylene/polyoxypropylene copolymer relates to its monomeric composition. The first two digits of a poloxamer number, multiplied by 100, gives the approximate molecular weight of the hydrophobic polyoxypropylene block. The last digit, multiplied by 10, gives the approximate weight percent of the hydrophilic polyoxyethylene content. For example, poloxamer 188 describes a polymer containing a polyoxypropylene hydrophobe of about 1,800 Da with a hydrophilic polyoxyethylene block content of about 80% of the total molecular weight.

Poloxamers can be synthesized in two steps, first by building the polyoxypropylene core, and then by addition of polyoxyethylene to the terminal ends of the polyoxypropylene core. Because of variation in the rates of polymerization during both steps, a poloxamer can contain heterogeneous polymer species of varying molecular weights. The distribution of polymer species can be characterized using standard techniques including, but not limited to, gel permeation chromatography (GPC).

As used herein, Poloxamer 188 (also called P-188 or P188) refers to a polyoxyethylene/polyoxypropylene copolymer that has the following chemical formula:

$$HO(CH_2CH_2O)_{a'}-[CH(CH_3)CH_2O]_b-(H_2CH_2O)_aH, \text{ where:}$$

a' and a can be the same or different and each is an integer such that the hydrophile portion represented by ($C_2H_4O$) (i.e. the polyoxyethylene portion of the copolymer) constitutes approximately 60% to 90%, such as approximately 80% or 81%; and b is an integer such that the hydrophobe represented by ($C_3H_6O$) has a molecular weight of approximately 1,300 to 2,300 Da, such as 1,400 to 2,000 Da, for example approximately 1,750 Da. For example, a is about 79 and b is approximately or is 28. The average total molecular weight of the compound is approximately 7,680 to 9,510 Da, such as generally 8,400-8,800 Da, for example about or at 8,400 Da. Poloxamer 188 is a preparation that can contain a heterogeneous distribution of polymer species that primarily vary in overall chain length of the polymer, but also include truncated polymer chains with unsaturation, and certain low molecular weight glycols. Included among poloxamer 188 molecules are those that exhibit a species profile (e.g., determined by GPC) containing a main peak and "shoulder" peaks on both sides representing low molecular weight (LMW) polymer species and high molecular weight (HMW) polymer species. Poloxamer 188 also refers to materials that are purified to remove or reduce species other than the main component.

As used herein, "main component" or "main peak" with reference to a poloxamer 188 preparation refers to the species of copolymer molecules that have a molecular weight of less than about 13,000 Da and greater than about 4,500 Da, with an average molecular weight of between about 7,680 to 9,510 Da, such as generally 8,400-8,800 Da, for example about or at 8,400 Da. Main peak species include those that elute by gel permeation chromatography (GPC) at between 14 and 15 minutes depending on the chromatography conditions (see U.S. Pat. No. 5,696,298).

As used herein, "low molecular weight" or "LMW" with reference to species or components of a poloxamer 188 preparation refers to components that have a molecular weight generally less than 4,500 Da. LMW species include those that elute by gel permeation chromatography (GPC) after 15 minutes depending on the chromatography conditions. (see U.S. Pat. No. 5,696,298). Such impurities can include low molecular weight poloxamers, poloxamer degradation products (including alcohols, aldehydes, ketones, and hydroperoxides), diblock copolymers, unsaturated polymers, and oligomeric glycols including oligo(ethylene glycol) and oligo(propylene glycol).

As used herein, "high molecular weight" or "HMW" with reference to species or components of a poloxamer 188 preparation refers to components that have a molecular weight generally greater than 13,000 Da, such as greater than 14,000 Da, greater than 15,000 Da, greater than 16,000 Da or greater. HMW species include those that elute by gel permeation chromatography (GPC) at between 13 and 14 minutes depending on the chromatography conditions (see U.S. Pat. No. 5,696,298).

As used herein, "polydispersity" or "D" refers to the breadth of the molecular weight distribution of a polymer composition. A monodisperse sample is defined as one in which all molecules are identical. In such a case, the polydispersity (Mw/Mn) is 1. Narrow molecular weight standards have a value of D near 1 and a typical polymer has a range of 2 to 5. Some polymers have a polydispersity in excess of 20. Hence, a high polydispersity value indicates a wide variation in size for the population of molecules in a given preparation, while a lower polydispersity value indicates less variation. Methods for assessing polydispersity are known in the art, and include methods as described in U.S. Pat. No. 5,696,298. For example, polydispersity can be determined from chromatograms. It is understood that polydispersity values can vary depending on the particular chromatogram conditions, the molecular weight standards and the size exclusion characteristics of gel permeation columns employed. For purposes herein, reference to polydispersity is as employed in U.S. Pat. No. 5,696,298, as determined from chromatograms obtained using a Model 600E Powerline chromatographic system equipped with a column heater module, a Model 410 refractive index detector, Maxima 820 software package (all from Waters, Div. of Millipore, Milford, Mass.), two LiChrogel PS-40 columns and a LiChrogel PS-20 column in series (EM Science, Gibbstown, N.J.), and polyethylene glycol molecular weight standards (Polymer Laboratories, Inc., Amherst, Mass.). It is within the level of a skilled artisan to convert any polydispersity value that is obtained using a different separation method to the values described herein simply by running a single sample on both systems and then comparing the polydispersity values from each chromatogram.

As used herein, "purified poloxamer 188" or "P188-P" or "purified long circulating material (LCM)-containing poloxamer 188" refers to a poloxamer 188 that has polydispersity value of the poloxamer of less than or about 1.07, such as less than or 1.05 or less than or 1.03, and is a purified poloxamer 188 that has a reduced amount of low molecular weight components, but contains the longer circulating material. A poloxamer 188 in which "low molecular weight material has been removed" or "low molecular weight material has been reduced," or similar variations thereof, refers to a purified poloxamer 188 in which there is a distribution of low molecular weight components of no more than or less than 3.0%, and generally no more than or less than 2.0% or no more than or less than 1.5% of the total distribution of components. Typically, such a poloxamer 188 exhibits reduced toxicity compared to forms of poloxamer 188 that contain a higher or greater percentage of low molecular weight components. The poloxamer 188 is purified to remove or reduce low molecular weight components. Commercially available and prior preparations of poloxamer, such as poloxamer 188, have a long circulating material (LCM) that, when administered to a human, has a half life that is more than 5.0 fold the circulating half-life of the main component in the distribution of the copolymer.

An exemplary purified LCM-containing poloxamer 188 is poloxamer 188 available under the trademark FLOCOR® (see, also U.S. Pat. No. 5,696,298, which describes LCM-containing poloxamer 188). When the purified LCM-containing poloxamer 188 is administered as an intravenous injection to a mammal, particularly a human, GPC analysis of blood obtained from the treated subject exhibits two circulating peaks: a peak designated the main peak that comprises the main component of the polymeric distribution and a peak of higher molecular weight, compared to the main peak, that exhibits a substantially slower rate of clearance (more than 5-fold slower than the main peak, typically more than 30 hours and as much as 70 hours, as shown herein) from the circulation, i.e., a long circulating material (LCM).

As used herein, long circulating material (LCM) refers to material in prior poloxamer preparations that, upon administration to a subject, have a half-life in the subject, such as a human, that is substantially longer than the half-life of the main component of the poloxamer preparation. When administered to a human subject the LCM material in a poloxamer preparation has more than about or more than 5-fold the half life of the main component of the poloxamer preparation. The LCMF poloxamers as provided herein do not give rise to such longer circulating material. There is no component that has a half-life that it 5-fold longer than the main component. For comparing poloxamers, components of corresponding poloxamers are compared, where a corresponding poloxamers have the same formula. For example, an LCMF poloxamer 188 is compared to a poloxamer 188.

As used herein, "long circulating material free" or "LCMF" with reference to poloxamer 188 refers to a purified poloxamer 188 preparation that has a reduced amount of low molecular weight components, as described above for purified poloxamer 188, and that, following intravenous administration to a subject, the components of the polymeric distribution clear from the circulation in a more homogeneous manner such that any long circulating material exhibits a half-life (in human subjects) that is no more than 5-fold longer than the circulating half-life ($t_{1/2}$) of the main peak. Thus, an LCMF is a poloxamer 188 that does not contain components, such as a high molecular weight components or low molecular weight components as described herein, that are or gives rise to a circulating material with a $t_{1/2}$ that, when administered to a human subject, is more than 5.0-fold greater than the $t_{1/2}$ of the main component, and generally no more than 4.0, 3.0, 2.0 or 1.5 fold greater than the half-life of the main component in the distribution of the copolymer. Typically, an LCMF poloxamer is a poloxamer in which all of the components of the polymeric distribution clear from the circulation at a more homogeneous rate.

As used herein, "distribution of copolymer" refers to the molecular weight distributions of the polymeric molecules in a poloxamer preparation. The distribution of molecular masses can be determined by various techniques known to a skilled artisan, including but not limited to, colligative property measurements, light scattering techniques, viscometry and size exclusion chromatography. In particular, gel permeation chromatography (GPC) methods can be employed that determine molecular weight distribution based on the polymer's hydrodynamic volume. The distribution of molecular weight or mass of a polymer can be summarized by polydispersity. For example, the greater the disparity of molecular weight distributions in a poloxamer, the higher the polydispersity.

As used herein, half-life, biological half-life, plasma half-life, terminal half-life, elimination half-life or $t_{1/2}$ refer to the time that a living body requires to eliminate one half of the quantity of an administered substance through its normal channels of elimination. The normal channels of elimination generally include the body's cleansing through the function of kidneys and liver in addition to excretion functions to eliminate a substance from the body. Half-life can be described as the time it takes the blood plasma concentration of a substance to halve its steady state level, i.e. the plasma half-life. A half-life can be determined by giving a single dose of drug, usually intravenously, and then the concentration of the drug in the plasma is measured at regular intervals. The concentration of the drug will reach a peak value in the plasma and will fall as the drug is broken down and cleared from the blood.

As used herein "Cmax" refers to the peak or maximal plasma concentration of a drug after administration.

As used herein, the "concentration of a drug at steady state" or "Css" refers to the concentration of drug at which the rate of drug elimination and drug administration are equal. It is achieved generally following the last of an infinite number of equal doses given at equal intervals. The time required to achieve a steady state concentration depends on the half-life of the drug. The shorter the half-life, the more rapidly steady state is reached. Typically it takes 3-5 half-lives to accumulate to greater than 90% of the final steady state concentrations.

As used herein, "impurities" refer to unwanted components in a poloxamer preparation. Typically impurities include LMW components less than 4,500 Daltons and high molecular weight components greater than 13,000 Daltons.

As used herein, "remove or reduce" with reference to a poloxamer component in a preparation refers to decreasing the weight percentage of the component in the poloxamer preparation relative to the initial percentage of the component. Generally, a poloxamer component is removed or reduced if the percentage by weight of the component to the total distribution of components is decreased by at least 1%, and typically at least 2%, 3%, 4%, 5%, or more. For example, most commercial preparations of a poloxamer 188 contain a LMW component (less than 4,500 Daltons) that is about 4% by weight of the total components in the distribution. The LMW component is reduced in a purified product if there is less than 3% by weight of the component, such as less than 2% or 1%.

As used herein, "solvent" refers to any liquid in which a solute is dissolved to form a solution.

As used herein, a "polar solvent" refers to a solvent in whose molecules there is either a permanent separation of positive and negative charges, or the centers of positive and negative charges do not coincide. These solvents have high dielectric constants, are chemically active, and form coordinate covalent bonds. Examples of polar solvents are alcohols and ketones.

As used herein, "feed" refers to a solute dissolved in a solvent.

As used herein, an "extraction solvent" refers to any liquid or supercritical fluid that can be used to solubilize undesirable materials that are contained in a poloxamer preparation. It is a solvent that can effect solvent extraction to separate a substance from one or more others based on variations in the solubilities. Generally an extraction solvent is immiscible or partially miscible with the solvent in which the substance of interest is dissolved. For example, an extraction solvent is one that does not mix or only partially mixes with a first solvent in which the substance of interest is dissolved, so that, when undisturbed, two separate layers form. Exemplary extraction solvents are supercritical liquids or high pressure liquids.

As used herein, the terms "supercritical liquid" and "supercritical fluid" include any compound, such as a gas, in a state above its critical temperature ($T_c$; i.e. the temperature, characteristic of the compound, above which it is not possible to liquefy the compound) and critical pressure ($p_c$; i.e., the minimum pressure which would suffice to liquefy the compound at its critical temperature). In this state, distinct liquid and gas phases typically do not exist. A supercritical liquid typically exhibits changes in solvent density with small changes in pressure, temperature, or the presence of a co-modifier solvent.

As used herein, "supercritical carbon dioxide" refers to a fluid state of carbon dioxide where it is held at or is above its critical temperature (about 31° C.) and critical pressure (about 74 bars). Below its critical temperature and critical pressure, carbon dioxide usually behaves as a gas in air or as a solid, dry ice, when frozen. At a temperature that is above 31° C. and a pressure above 74 bars, carbon dioxide adopts properties midway between a gas and a liquid, so that it expands to fill its container like a gas but with a density like that of a liquid.

As used herein, "critical temperature" or "critical point" refers to the temperature that denotes the vapor-liquid critical point, above which distinct liquid and gas phases do not exist. Thus, it is the temperature at and above which vapor of the substance cannot be liquified no matter how much pressure is applied. For example, the critical temperature of carbon dioxide is about 31° C.

As used herein, "critical pressure" refers to the pressure required to liquefy a gas at its critical temperature. For example, the critical pressure of carbon dioxide is about 74 bars.

As used herein, the term "high pressure liquid" includes a liquid formed by pressurizing a compressible gas into the liquid at room temperature or a higher temperature.

As used herein, a "co-modifier solvent" refers to a polar organic solvent that increases the solvent strength of an extraction solvent (e.g., supercritical fluid carbon dioxide). It can interact strongly with the solute and thereby substantially increase the solubility of the solute in the extraction solvent. Examples of co-modifier solvents include alkanols. Typically between 5% and 15% by weight of co-modified solvent can be used.

As used herein, the term "alkanol" includes simple aliphatic organic alcohols. In general, the alcohols intended for use in the methods provided herein include six or fewer carbon atoms (i.e., $C_1$-$C_6$ alkanols). The alkane portion of the alkanol can be branched or unbranched. Examples of alkanols include, but are not limited to, methanol, ethanol, isopropyl alcohol (2-propanol), and tert-butyl alcohol.

As used herein, "subcritical extraction" refers to processes using a fluid substances that would usually be gaseous at normal temperatures and pressures, that are converted to liquids at higher pressures and lower temperatures. The pressures or temperatures are then normalized and the extracting material is vaporized leaving the extract. Extractant can be recycled.

As used herein, "extraction vessel" or "extractor" refers to a high-pressure vessel that is capable of withstanding pressures of up to 10,000 psig and temperatures of up to 200° C. The volume of the vessels can range from 2 mL to 200 L, and generally is 1 L to 200 L, such as 5 L to 150 L. Extraction vessels generally are made out of stainless steel. Such devices are well known to a skilled artisan and available commercially.

As used herein, "isocratic" refers to a system in which an extraction solvent is used at a constant or near constant concentration.

As used herein, "gradient" or "gradient steps" refers to a system in which two or more extraction solvents are used that differ in their composition of components, typically by changes in concentration of one or more components. For example, the concentration of the alkanol solvent (e.g., methanol) is successively increased during the course of the extraction. Thus, the extraction solvent does not remain constant.

As used herein, "plurality" refers to a number of iterations of a process or step. The number of repeats can be 2, 3, 4, 5, 6 or more.

As used herein, "extracted material" refers to the product containing the removed materials.

As used herein, "raffinate" refers to a product which has had a component or components removed. For example, the purified poloxamer in which extracted material has been removed.

As used herein, "batch method" or "batch extraction" refers to a process of extracting the solute from one immiscible layer by shaking the two layers until equilibrium is attained, after which the layers are allowed to settle before sampling. For example, a batch extraction can be performed by mixing the solute with a batch of extracting solvent. The solute distributes between the two phases. Once equilibrium is achieved, the mixing is stopped and the extract and raffinate phases are allowed to separate. In this method, the spent solvent can be stripped and recycled by distillation or fresh solvent can be added continuously from a reservoir.

As used herein, a "continuous method" or "continuous extraction" refers to a process in which there is a continuous flow of immiscible solvent through the solution or a continuous countercurrent flow of both phases. For example, a continuous extracting solvent is mixed with the solute. The emulsion produced in the mixer is fed into a settler unit where phase separation takes place and continuous raffinate and extract streams are obtained.

As used herein, "pharmaceutical composition" includes a composition comprising a polyoxyethylene/polyoxypropylene copolymer described herein, such as an LCMF poloxamer, formulated as a pharmaceutically acceptable formulation and/or with one or more pharmaceutically acceptable excipients. In certain instances, the pharmaceutical composition comprises an aqueous injectable solution of the poloxamer buffered at a desired pH, such as 6-7 or 6 or about 6, with a suitable buffer. Exemplary of buffers are any known to those of skill in the art to be biocompatible, such as citrate, including for example sodium citrate/citric acid. Suitable concentrations can be empirically determined, but typically range from 0.005 to 0.05 M, particularly about 0.01 M in an isotonic solution such as saline. In certain instances, pharmaceutical compositions useful in the methods herein are known to those of skill in the art for formulating poloxamer (see, e.g., Published International PCT Application No. WO 94/008596 and other such references and publications described herein).

As used herein, "treatment" refers to ameliorating or reducing symptoms associated with a disease or condition. Treatment means any manner in which the symptoms of a condition, disorder or disease are ameliorated or otherwise beneficially altered. Hence treatment encompasses prophylaxis, therapy and/or cure. Treatment also encompasses any pharmaceutical use of the compositions herein.

As used herein, "treating" a subject having a disease or condition means that a composition or other product provided or described herein is administered to the subject to thereby effect treatment thereof.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, "prevention" or "prophylaxis" refers to methods in which the risk of developing a disease or condition is reduced. Prophylaxis includes reduction in the risk of developing a disease or condition and/or a prevention of worsening of symptoms or progression of a disease, or reduction in the risk of worsening of symptoms or progression of a disease.

As used herein an "effective amount" of a compound or composition for treating a particular disease is an amount that is sufficient to ameliorate, or in some manner reduce symptoms to achieve the desired physiological effect. Such amount can be administered as a single dosage or can be administered according to a regimen, whereby it is effective. The effective amount is readily determined by one of skill in the art following routine procedures, and depends upon the particular indication for which the composition is administered.

As used herein, "therapeutically effective amount" or "therapeutically effective dose" refers to an agent, compound, material, or composition containing a compound that is at least sufficient to produce a therapeutic effect. An effective amount is the quantity of a therapeutic agent sufficient to treat, such as prevent, cure ameliorate, arrest or otherwise treat a particular disease or disorder.

As used herein, "disease" or "disorder" refers to a pathological condition in an organism resulting from cause or condition including, but not limited to, infections, acquired conditions, and genetic conditions, and characterized by identifiable symptoms. Diseases and disorders of interest herein include, but are not limited to, any requiring membrane resealing and repair, tissue ischemia and reperfusion injury, decreasing inflammatory disorders, disorders related thrombolysis, and disorders related to hemostasis. For example, diseases and disorders include acute myocardial infarction, acute limb ischemia, shock, acute stroke, heart failure, sickle cell disease, neurodegenerative diseases, macular degeneration, diabetic retinopathy and congestive heart failure.

As used herein, "subject" refers to an animal, particularly human or a veterinary animal, including dogs, cats, pigs, cows, horses and other farm animals, zoo animals and pets. Thus, "patient" or "subject" to be treated includes humans and or non-human animals, including mammals. Mammals include primates, such as humans, chimpanzees, gorillas and monkeys; domesticated animals, such as dogs, horses, cats, pigs, goats, cows; and rodents such as mice, rats, hamsters and gerbils.

As used herein, a "combination" refers to any association between two or among more items. The association can be spatial, such as in a kit, or refer to the use of the two or more items for a common purpose.

As used herein, a "composition" refers to any mixture of two or more products or compounds (e.g., agents, modulators, regulators, etc.). It can be a solution, a suspension, liquid, powder, a paste, aqueous or non-aqueous formulations or any combination thereof.

As used herein, an "article of manufacture" is a product that is made and sold. The term is intended to encompass purified poloxamers contained in articles of packaging.

As used herein, fluid refers to any composition that can flow. Fluids thus encompass compositions that are in the form of semi-solids, pastes, solutions, aqueous mixtures, gels, lotions, creams and other such compositions.

As used herein, a "kit" refers to a packaged combination, optionally including reagents and other products and/or components for practicing methods using the elements of the combination. For example, kits containing purified poloxamers provided herein and another item for a purpose including, but not limited to, administration, diagnosis, and assessment of a biological activity or property are provided. Kits optionally include instructions for use.

As used herein, animal includes any animal, such as, but not limited to; primates including humans, gorillas and monkeys; rodents, such as mice and rats; fowl, such as chickens; ruminants, such as goats, cows, deer, sheep; ovine, such as pigs and other animals. Non-human animals exclude humans as the contemplated animal.

As used herein, the singular forms "a," "an" and "the" include plural referents unless the context clearly dictates otherwise.

As used herein, ranges and amounts can be expressed as "about" or "approximately" a particular value or range. About also includes the exact amount. Hence "about 0.05 mg/mL" means "about 0.05 mg/mL" and also "0.05 mg/mL."

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein "retention time" or "$t_R$" means the time elapsed between the injection of a sample, such as an LCMF poloxamer 188 sample, onto a reverse phase column for reverse phase high performance liquid chromatography and the peak response by the evaporative light scattering detector. The retention time is longer for more hydrophobic samples compared to less hydrophobic samples.

As used herein "capacity factor" or k' is determined by the following equation where to is equal to the void time or the time a non retained substance passes through a reverse phase HPLC column (see, Example 7 below):

$$k' = \frac{t_R - t_0}{t_0}.$$

LCM-containing purified poloxamer 188, such as the poloxamer sold under the trademark FLOCOR®, has a mean retention time ($t_R$) of 9.883 and a k' of 3.697; whereas the LCMF poloxamer 188 has a mean retention time ($t_R$) of 8.897 and a mean k' of 3.202 (see Example 7)

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

B. MOLECULAR DIVERSITY OF POLOXAMERS, POLOXAMER 188, LCM-CONTAINING POLOXAMER 188 AND LCMF POLOXAMERS

1. Poloxamers

Poloxamers are a family of synthetic, linear, triblock copolymers composed of a core of repeating units of polyoxypropylene (PO or POP), flanked by chains of repeating units of polyoxyethylene (EO or POE). All poloxamers are defined by this EO-PO-EO structural motif. Specific poloxamers (e.g., poloxamer 188) are further defined by the number of repeating EO and PO units, which provide specific poloxamers with different chemical and physical characteristics, as well as unique pharmacodynamic properties.

Certain polyoxyethylene/polyoxypropylene copolymers, including poloxamer 188, have beneficial biological effects on several disorders when administered to a human or animal. These activities have been described, for example in numerous publications and patents (see, e.g., U.S. Pat. Nos. 4,801,452, 4,837,014, 4,873,083, 4,879,109, 4,897,263, 4,937,070, 4,997,644, 5,017,370, 5,028,599, 5,030,448, 5,032,394, 5,039,520, 5,041,288, 5,047,236, 5,064,643, 5,071,649, 5,078,995, 5,080,894, 5,089,260, RE 36,665 (Reissue of U.S. Pat. No. 5,523,492), 5,605,687, 5,696,298 6,359,014, 6,747,064, 8,372,387, 8,580,245, U.S. Patent Publication Nos. 2011/0044935, 2011/0212047, 2013/0177524, and International Applications WO2006/037031 (filed as PCT/US2005/034790), WO2009/023177 (filed as PCT/US2005/037157) and WO2006/091941 (filed as PCT/US2006/006862), and PCT/US2014/45627, U.S. Provisional Application Ser. Nos. 62/021,691 and 62/021,676). Among the activities of poloxamers, such as poloxamer 188, that make them useful as therapeutic agents is their ability to incorporate into cellular membranes, and thereby repair damaged cell membranes.

Poloxamers include POP/POE block copolymers having the following formula:

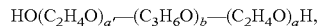

where "a'" and "a" can be the same or different and each is an integer such that the hydrophile portion represented by ($C_2H_4O$) constitutes approximately 50% to 95% by weight of the compound, such as 60% to 90%, for example 70% to 90%, by weight of the compound; and the "b" is an integer such that the hydrophobe represented by ($C_3H_6O$) has a molecular weight of approximately 950 to 4,000 Da, such as 1,200 to 3,500 Da. For example, the hydrophobe has a molecular weight of 1,200 to 2,300 Da, such as generally 1,500 to 2,100 Da. The average molecular weight of the copolymer is 5,000 to 15,000 Da, such as 5,000 to 12,000 Da, for example 5,000 to 9,000 Da.

In certain instances, b is an integer of from about 15 to about 70, such as from about 15 to about 60, or from about 15 to about 30, or any of the numbers in between. In some instances, b is about 15, 16, 17, 18, 19, 20, 21, 22, 23, 24, 25, 26, 27, 28, 29, or 30. In certain aspects, the integers for the flanking units with the subscript "a'" and "a" can differ or are the same values. In some instances, a or a' is an integer of about 45 to about 910, such as 90, 100, 200, 300, 400, 500, 600, 700, 800, or 900. In some other instances, a or a' is an integer from about 10 to about 215, such as 10, 20, 30, 40, 50, 60, 70, 80, 100, 125, 150, 175, 200 or 215. In still other instances, a or a' is about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70. A skilled artisan will appreciate that these values are average values. The values for a', a and b represent an average; generally the polymeric molecules are a distribution or population of molecules. Therefore the actual values of a, a' and b within the population constitute a range of values.

The nomenclature of the poloxamer relates to the composition of the various polymer members. The first two digits of a poloxamer number, multiplied by 100, gives the approximate molecular weight of the hydrophobe. The last digit, times 10, gives the approximate weight percent of the hydrophile (polyoxyethylene) content of the surfactant. For example, poloxamer 407 describes a polymer containing a polyoxypropylene hydrophobe of about 4,000 Da with the polyoxyethylene hydrophile comprising about 70% of the total molecular weight. Poloxamer 188 (P188) has a hydrophobe with a molecular weight of about 1,800 Da and has a hydrophile that is about 80% of the total molecular weight of the copolymer.

Poloxamers are sold and referred to under trade names and trademarks including, but not limited to, ADEKA NOL, Synperonic™, Pluronic® and Lutrol®. Exemplary poloxamers include, but are not limited to, poloxamer 188 (P188; sold under the trademarks Pluronic® F-68, Kolliphor® P 188, 80% POE), poloxamer 407 (P407; sold under the trademark Lutrol F-127, Kolliphor® P 188, Pluronic® F-127; 70% POE), poloxamer 237 (P237; sold under the trademark Pluronic® F87, Kolliphor® P 237; 70% POE), poloxamer 338 (P338; sold under the trademark Kolliphor® P 338, Pluronic® F-108; 80% POE) and poloxamer 331 (Pluronic® L101; 10% POE).

Hence, non-purified P188 is commercially available or known under various names as described above. While the discussion below references using the methods herein to produce a more homogenous (LCMF) poloxamer 188, methods herein can be used to produce more homogenous preparations of any of the known poloxamers.

Poloxamers can be synthesized using standard polymer synthesis techniques. For example, poloxamers are formed by ethylene oxide-propylene oxide condensation using standard techniques know to those of ordinary skill in the art (see, e.g., U.S. Pat. Nos. RE 36,665, RE 37,285, RE 38,558, 6,747,064, 6,761,824 and 6,977,045; see also Reeve, L. E., The Poloxamers: Their Chemistry and Medical Applications, in Handbook of Biodegradable Polymers, Domb, A. J. et al. (eds.), Hardwood Academic Publishers, 1997). Poloxamers can be synthesized by sequential addition of POP and POE monomers in the presence of an alkaline catalyst, such as sodium or potassium hydroxide (See, e.g., Schmolka, J. Am. Oil Chem. Soc. 54 (1977) 110-116). The reaction is initiated by polymerization of the POP block followed by the growth of POE chains at both ends of the POP block. Methods of synthesizing polymers also are described in U.S. Pat. No. 5,696,298.

2. Poloxamer 188

A poloxamer 188 (P188) copolymer has the following chemical formula:

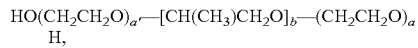
H, where the hydrophobe represented by (C₃H₆O) has a molecular weight of approximately 1,750 Daltons and the poloxamer 188 has an average molecular weight of 7,680 to 9,510 Da, such as generally approximately 8,400-8,800 Daltons. The polyoxyethylene-polyoxypropylene-polyoxyethylene weight ratio is approximately 4:2:4. According to specifications, P188 has a weight percent of oxyethylene of 81.8±1.9% and an unsaturation level of 0.026±0.008 mEq/g.

Various poloxamers, and in particular P188, are used for treatment of diseases and conditions in which resistance to blood flow is pathologically increased by injury due to the presence of adhesive hydrophobic proteins or damaged membranes. This adhesion is produced by pathological hydrophobic interactions and does not require the interaction of specific ligands with their receptors. Such proteins and/or damaged membranes increase resistance in the microvasculature by increasing friction and reducing the effective radius of the blood vessel. For example, it is believed that poloxamer 188 acts as a lubricant to increase blood flow through damaged tissues. Advantageously, this blocks adhesion of hydrophobic surfaces to one another and thereby reduces friction and increases flow.

P188 binds to hydrophobic areas developed on injured cells and denatured proteins thereby restoring hydration lattices. Such binding facilitates sealing of damaged membranes and aborts the cascade of inflammatory mediators that could destroy the cell. This polymer also inhibits hydrophobic adhesive interactions that cause deleterious aggregation of formed elements in the blood. P188's anti-adhesive and anti-inflammatory effects are exhibited by enhancing blood flow in damaged tissue by reducing friction, preventing adhesion and aggregation of formed elements in the blood, maintaining the deformability of red blood cells, non-adhesiveness of platelets and granulocytes and the normal viscosity of blood, reducing apoptosis, and by multiple markers of inflammation including VEGF, various chemokines, and interleukins.

3. Molecular Diversity of Poloxamer 188

Commercially available poloxamer 188 preparations are stated to have a molecular weight of approximately 8,400 Daltons. Such poloxamer 188, however, is composed of molecules having a molecular weight from less than 3,000 Daltons to over 20,000 Daltons. The molecular diversity and distribution of molecules of commercial poloxamer 188 can be seen in the broad primary and secondary peaks detected using gel permeation chromatography (see, e.g., International PCT published Application No. WO 94/08596).

The diversity in structure means that there is a diversity in biological activity. For example, the optimal rheologic, cytoprotective, anti-adhesive and antithrombotic effects are observed with molecules of P188 that are approximately 8,400 to 9,400 Daltons. Such components can be identified as the main or predominant component in a poloxamer preparation using methods that separate components based on size, such as gel permeation chromatography (GPC). The distribution of components, however, also typically show a smaller fraction of low molecular weight (LMW, i.e. generally below 4,500 Daltons) or high molecular weight (HMW, i.e. generally above 13,000 Daltons) components. P188 components above 15,000 and below 4,500 Daltons are less effective rheologic or cytoprotective agents and exhibit unwanted side effects. The other substances or components in a poloxamer preparation, such as a P188 preparation, originate from two different sources, synthesis and degradation.

A primary mechanism contributing to the molecular diversity is the process by which poloxamers are synthesized. During the typical manufacturing process, the first step is the formation of the POP blocks. These are formed by reacting a propylene glycol initiator with propylene oxide monomer. Subsequently, ethylene oxide monomer is added to both ends forming the block copolymer. The synthesis of poloxamers can result in a variation in the rates of polymerization during the steps of building the PO core and EO terminal ends.

During the synthesis of the POP, two different reaction mechanisms limit POP chain growth and result in unintended diblock polymers. These substances are typically of lower molecular weight (relative to the polymeric distribution of P188). In one mechanism, unsaturation is formed directly from propylene oxide by reacting with an alkali catalyst. The base catalyzes the rearrangement of the propylene oxide to an allyl alcohol, which then initiates a mono functional chain with terminal unsaturation. These types of side reactions will produce low molecular weight (LMW) substances throughout the time of the reaction. On gel permeation chromatography (GPC), the distribution of these impurities are located in the main peak as well as in the LMW shoulder. In a second mechanism, the abstraction of a hydrogen atom, located six carbon atoms away, by the negative oxygen atom in a growing polymer chain can terminate and transfer the chain, producing an allyl end group. These back-biting reactions are predominant with high molecular weight (HMW) POP blocks. The distribution of these substances is mostly in the LMW shoulder.

In addition, high molecular weight substances (relative to the polymeric distribution of P188) can be formed due to inadequate cleaning of the polymerization reactor between batches of poloxamer 188 during a typical commercial manufacturing campaign. If the reactor is not completely cleaned to remove residual product after manufacturing a typical batch of poloxamer, such as P188, the residual product will act as an initiator in the subsequent batch and form a "dimer like" poloxamer molecule. This substance is of higher molecular weight and would be part of the polymeric distribution observed on GPC as the HMW shoulder.

The degradation pathways for poloxamers include peroxidation leading to low molecular aldehydes and acids and thermal degradation leading to LMW polyethylene glycols. Oxidative degradation is the primary degradation pathway affecting stability of poloxamers. This process generates structural changes to the polymer chain and generates peroxides and carbonyls. Peroxides are transient in nature and quickly combine with butylated hydroxytoluene (BHT), which is typically added to commercial preparations as an antioxidant. Thermal degradation is another pathway that produces other substances. Glycols of various chain lengths are major degradation products of thermal degradation. Forced thermal degradation studies have shown that ethylene glycol, propylene glycol, diethylene glycol and triethylene glycol are formed.

Thus, specific poloxamers are composed of multiple chemical entities that have the EO-PO-EO structural motif, but vary in the number of repeating EO and PO units. Various truncated polymers with an EO-PO motif and a variety of other substances can form as a result of side reactions occurring during synthesis of the intended poloxamer compound. These other substances can be present and found within the overall poloxamer distribution. The result is material that is non-uniform (i.e. material that is polydisperse).

For example, due to the synthesis of P188, there can be variation in the rates of polymerization during the steps of building the PO core and EO terminal ends. Thus, most non-purified forms of P188 contain a bell-shaped distribution of polymer species, which vary primarily in overall chain length. In addition, various low molecular weight (LMW) components (e.g., glycols and truncated polymers) formed by incomplete polymerization, and high molecular weight (HMW) components (e.g., dimerized polymers) can be present. Typically, characterization of P188 by gel permeation chromatography (GPC) identifies a main peak of P188 with "shoulder" peaks representing the unintended LMW and HMW components (Emanuele and Balasubramanian (2014) *Drugs R D*, 14:73-83). For example, the preparation of P188 that is available from BASF (Parsippany, N.J.) has a published structure that is characterized by a hydrophobic block with a molecular weight of approximately 1,750 Da, POE blocks making up 80% of the polymer by weight, and a total molecular weight of approximately 8,400 Da. The actual compound is composed of the intended POE-POP-POE copolymer, but also contains other molecules which range from a molecular weight of less than 1,000 Da to over 30,000 Da. The molecular diversity and distribution of molecules of commercial poloxamer 188 is illustrated by broad primary and secondary peaks detected using gel permeation chromatography. The diversity of molecules present in the non-purified poloxamer preparations, including commercially available poloxamers, can result in diverse biological activities. Many of the observed biological activities are undesired or/and can result in unwanted side effects that limit the therapeutic efficacy of poloxamers as drugs. Complement activation, phagocyte migration paralysis, and cytotoxicity observed upon administration of artificial blood preparations have been attributed in part to impurities in the poloxamer 188 component of those preparations. In addition, infusion of poloxamer 188 was shown to result in elevated creatinine, indicating kidney damage, and increased organ weights (kidney) in toxicological animal studies. Histologic evaluation of the kidney demonstrated a dose related cytoplasmic vacuolation of the proximal tubular epithelial cells.

Poloxamer 188 (see, e.g., Grindel et al. (2002) *Journal of Pharmaceutical Sciences*, 90:1936-1947 (Grindel et al. 2002a) or Grindel et al. (2002) *Biopharmaceutics & Drug Disposition*, 23:87-103 (Grindel et al. 2002b)), which is purified to remove lower molecular weight components, contains components that, when administered to a subject, exhibit different pharmacokinetic profiles. The main component exhibits a half-life ($t_{1/2}$) in plasma of about 7 hours and a higher molecular weight component (i.e. the longer retention time species) exhibits about a 10-fold or more increase in half-life with a $t_{1/2}$ of approximately 70 hours or more and, thus, a substantially longer plasma residence time with slower clearance from the circulation than the main component. This is demonstrated herein (see, e.g., FIG. 8A and FIG. 8B).

a. Low Molecular Weight Components

Substances in poloxamer 188 that are toxic to kidneys have been identified as being of lower molecular weights than the main components. Studies on the therapeutic potential of P188 led to the discontinuance of the poloxamer available under the trademark RheothRx® for therapeutic applications in part due to an acute renal dysfunction observed during clinical trial evaluation as evidenced by elevated serum creatinine. It was found that these effects were due to the presence of various low molecular weight (LMW) substances that formed during the synthesis process (Emanuele and Balasubramanian (2014) *Drugs R D*, 14:73-83). The LMW substances were accumulated by the proximal tubule epithelial cells in the kidney.

The molecular weight of the LMW substances can range from a few hundred Da to a few thousand Da. The complex nature of these impurities with wide solubility characteristics make it difficult to selectively remove them from the parent molecules. Conventional purification processes such as distillation, crystallization, ultrafiltration, and the like, do not effectively separate the low molecular weight (LMW) substances from the main component. Use of chromatographic techniques for purification, such as preparative GPC, are expensive and practically difficult to scale-up. Fine-tuning mixed solvent systems to differentially solubilize and remove various substances is also challenging and requires the use of large amounts of solvents that are costly to recycle.

Supercritical fluid chromatography that reduces the level of these low molecular weight substances present in P188 has been reported (see, e.g., U.S. Pat. No. 5,567,859).

Supercritical fluid extraction was performed using carbon dioxide to purify the copolymers to reduce the polydispersity to less than 1.17. The method, however, does not sufficiently remove or reduce LMW components, as shown herein.

As described in more detail below, the methods provided herein produce poloxamer preparations that are substantially free of these LMW components. For example, purified P188 reduced in LMW components have less than about 5%, 4%, 3%, 2% or 1% LMW components. Thus, the poloxamer preparations provided herein, and in particular P188 poloxamer preparations, generally exhibit reduced toxicity and do not result in elevated creatinine levels when administered. In addition, as described herein, the resulting LCMF P188 poloxamer preparation has other advantageous properties, including a reduction of long circulating material upon administration.

b. Components Resulting in Long Circulating Half-Life

A component in P188 has been identified that is or gives rise to a material in the plasma or blood with a longer circulating half-life compared to the main or predominant poloxamer species. This material with the longer circulating half-life is observed in non-clinical and clinical studies. Analysis of plasma obtained following intravenous administration of purified P188 by high performance liquid chromatography—gel permeation chromatography (HPLC-GPC) shows two distinct peaks in the circulation (Grindel et al. (2002) *Journal of Pharmaceutical Sciences*, 90:1936-1947 (Grindel et al. 2002a) or Grindel et al. (2002) *Biopharmaceutics & Drug Disposition*, 23:87-103 (Grindel et al. 2002b). There is a main peak with an average peak molecular weight of about 8,600 Daltons and a smaller peak with an average molecular weight of about 16,000 Daltons. The two peaks exhibit distinctly different pharmacokinetic profiles with the higher molecular weight peak exhibiting a distinctly longer plasma residence time with slower clearance from the circulation (see, e.g., FIG. 8A and FIG. 8B). Similar observations were reported in rats and dogs. A similar longer circulating component is observed with native or unpurified poloxamer 188 (see International PCT Published Application No. WO 94/008596).

Figure 8A:
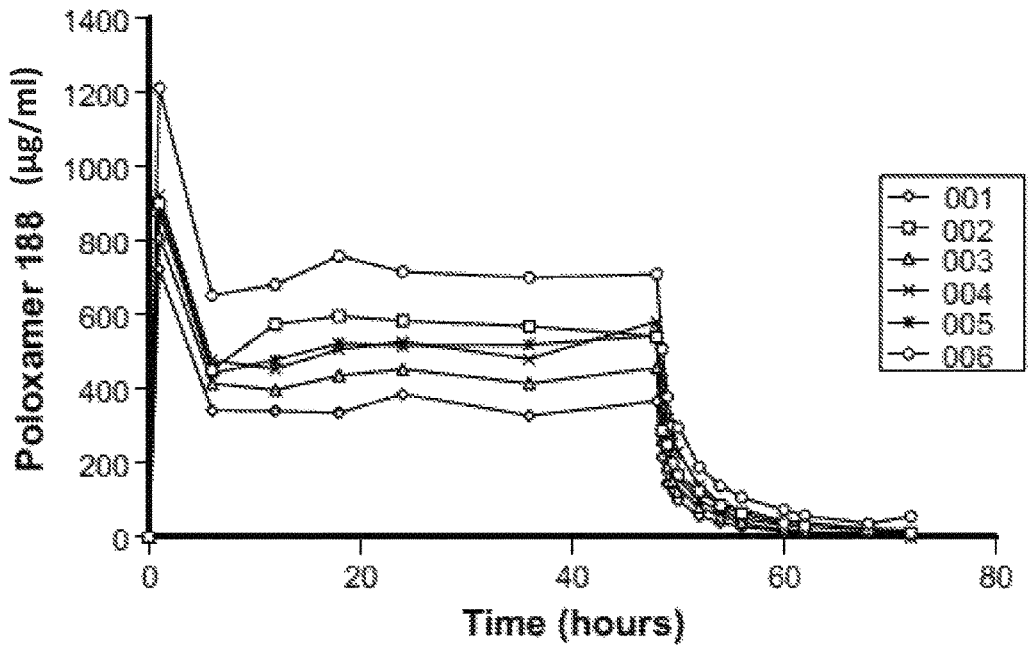
FIG. 8A shows individual plasma concentrations of Poloxamer 188 in healthy humans during and following a 48 hour continuous IV infusion of purified poloxamer 188 as described in Grindel et al. (2002) (Biopharmaceutics & Drug Disposition, 23:87-103).
Figure 8B:
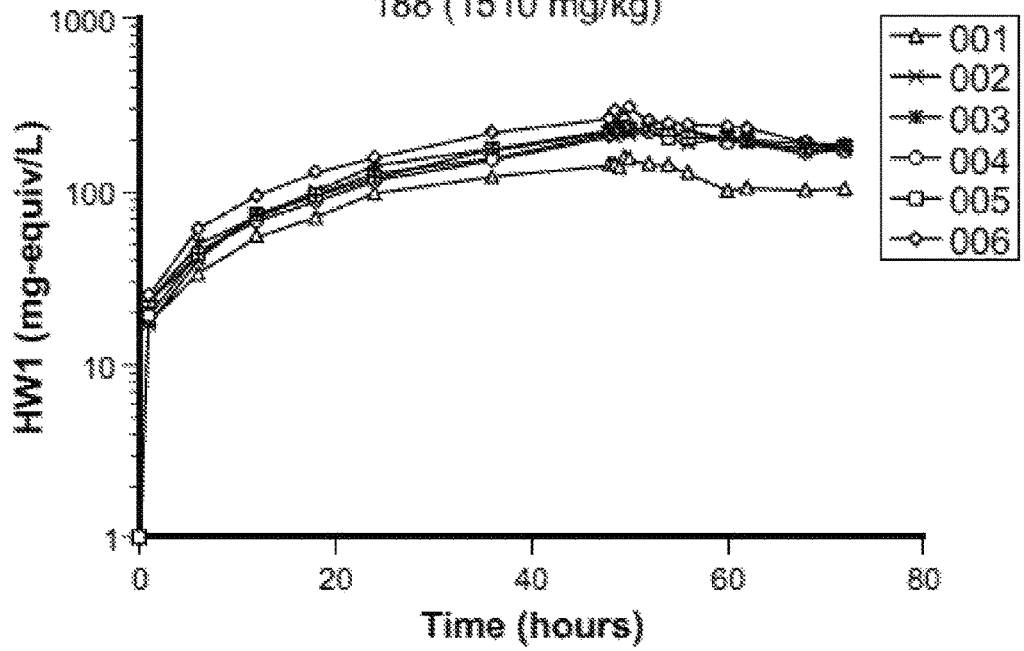
FIG. 8B shows individual plasma concentrations of high molecular weight component in healthy humans during and following a 48 hour continuous IV infusion of purified poloxamer 188 as described in Grindel et al. (2002) (Biopharmaceutics & Drug Disposition, 23:87-103).

For example, as shown in FIG. 8A, following administration of a purified P188 intravenously to healthy volunteers as a loading dose of 100 mg/kg/hr for one hour followed by a maintenance dose of 30 mg/kg/hr for 47 hours, the main or predominant peak reached a mean maximum concentration (Cmax) of 0.9 mg/mL by the end of the one hour loading infusion. A mean steady state concentration (Css) of 0.5 mg/mL was achieved essentially coincident with the start of the maintenance infusion. With the discontinuation of the maintenance infusion, plasma concentrations declined rapidly with an elimination half-life (t½) of about 7 hours. As shown in FIG. 8B, a HMW component was identified that exhibited a Cmax of 0.2 mg/mL, which was not attained until the end of the maintenance infusion. Steady state was not attained as the concentration continued to accumulate during infusion. Following discontinuation of the maintenance infusion, plasma levels of the high molecular weight peak declined slowly such that plasma levels had only declined by about 33% during the 24 hour post-infusion monitoring period. This elimination rate is approximately ⅒ that of the main peak and the $t_{1/2}$ is approximately 70 hours. See, also Grindel et al. (2002) *Journal of Pharmaceutical Sciences*, 90:1936-1947 (Grindel et al. 2002a) and Grindel et al. (2002) *Biopharmaceutics & Drug Disposition*, 23:87-103 (Grindel et al. 2002b). The long circulating material (or long retention time material) is identified in the HMW fraction of the P188 distribution (Grindel et al. (2002a)). This HMW component was determined to be approximately 16,000 Da as identified by MALDI-TOF mass spectrometry with a fragmentation pattern consistent with a block copolymer (see, e.g., Grindel et al. (2002a)).

Since the rheologic, cytoprotective, anti-adhesive and antithrombotic effects of P188 are optimal within the predominant or main copolymers of the distribution, which are approximately 8,400 to 9400 Daltons and have a half-life of about 7 hours, the presence of other components that exhibit a long circulating half-life is not desirable. For example, among the desired activities of P188 is its rheologic effect to reduce blood viscosity and inhibit red blood cell (RBC) aggregation, which account for its ability to improve blood flow in damaged tissues. In contrast, higher molecular weight poloxamers such as P338 (also called Pluronic® F108) and P308 (Pluronic® F98), increase blood viscosity and RBC aggregation (Armstrong et al. (2001) *Biorheology*, 38:239-247). This is the opposite effect of P188 and indicates that higher molecular weight poloxamer species may have undesirable biological effects.

As described in more detail below, provided are poloxamer preparations that are substantially reduced in the component that is or gives rise to a long circulating material, i.e., they are long circulating material free (LCMF). Also provided are exemplary methods (see, e.g., Example 7) for production of LCMF poloxamer. Thus, the LCMF poloxamer preparations provided herein, and in particular LCMF poloxamer 188 preparations, exhibit a more uniform pharmacokinetic profile, and thus a more consistent therapeutic effect. The LCMF poloxamer is described in more detail in the following section.

C. LONG CIRCULATING MATERIAL FREE (LCMF) POLOXAMER

Provided herein is a long circulating material free (LCMF) P188 that is a purified P-188 that has a polydispersity value less than 1.07; has no more than 1.5% of low molecular weight (LMW) components less than 4,500 Daltons; no more than 1.5% high molecular weight components greater than 13,000 Daltons; a half-life of all components in the distribution of the co-polymer that, when administered to a subject, is no more than 5.0-fold longer half-life in the blood or plasma than the half-life of the main component in the distribution of the co-polymer. Hence the LCMF Poloxamer 188, when administered, does not give rise to a component that has a significantly longer half-life than the main component. The LCMF P-188 has the following chemical formula:

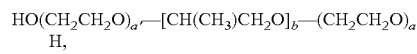

where a' and a can be the same or different and each is an integer such that the hydrophile portion represented by ($C_2H_4O$) (i.e., the polyoxyethylene portion of the copolymer) constitutes approximately 60% to 90%, such as approximately 80% or 81%; and b is an integer such that the hydrophobe represented by ($C_3H_6O$) has a molecular weight of approximately 1,300 to 2,300 Da, such as approximately 1,750 Da; and the average total molecular weight of the compound is approximately 7,680 to 9,510 Da, such as generally 8,400-8,800 Da, for example about or at 8,400 Da, where the copolymer has been purified to remove impurities, including low molecular weight impurities or other impurities, so that the polydispersity value is less than 1.07.

Studies have demonstrated that the main peak component of a purified (LCM-containing) P-188 preparation, when administered to a human subject, has a half-life ($t_{1/2}$) in (human) plasma of about 7 hours (Grindel et al. (2002) *Journal of Pharmaceutical Sciences*, 90:1936-1947 (Grindel et al. 2002a) or Grindel et al. (2002) *Biopharmaceutics & Drug Disposition*, 23:87-103 (Grindel et al. 2002b)). The purified poloxamer also resulted in a long circulating material (LCM) containing higher molecular weight components that have an average molecular weight of about 16,000 Daltons, which exhibit about a 10-fold or more increase in half-life with a $t_{1/2}$ of approximately 70 hours.

In contrast to the purified P-188 (LCM-containing) characterized, for example, in the studies of Grindel et al., (2002a and 2002b), the purified poloxamer, designated LCMF P-188, is one in which all components of the polymeric distribution, when administered to a subject, clear from the circulation at approximately the same rate. Thus, the LCMF P-188 is different from prior LCM-containing p188 poloxamers. Like LCM containing poloxamers, LCMF poloxamer contains a substantially less polydisperse composition of less than 1.07, and generally less than 1.05 or 1.03, but where the half-life in the blood or plasma of any components in the distribution of the co-polymer, when administered to a human subject, is no more than 5.0-fold longer than the half-life of the main component in the distribution of the co-polymer, and generally no more than 4.0-fold, 3.0-fold, 2.0-fold, 1.5-fold more longer. Typically, the LCMF does not contain any component that exhibits a half-life in the blood or plasma, when administered to a subject, that is substantially more (more than 5-fold) than or is more than the main component in the distribution of the co-polymer.

In some examples, the half-life in the blood or plasma of all components in the LCMF poloxamer, when administered to a human subject, is such that no component has a half-life that is more than 30 hours, and generally is no more than 25 hours, 20 hours, 15 hours, 10 hours, 9 hours, 8 hours or 7 hours.

Without being bound by theory, higher molecular weight components of the poloxamer polymeric distribution, such as those greater than 13,000 Daltons could account for the long circulating half-life material. The rate of glomerular filtration of uncharged molecules like poloxamer 188 and purified poloxamer 188 is highly dependent upon molecular size. This is observed for components of the poloxamer 188 polymeric distribution with molecular weights greater than 5,000 Daltons since, the rate of glomerular filtration becomes increasingly restricted above that size threshold (Chang et al., (1975) Biophysic. J. 15:887-906). Accordingly, the higher molecular weight components of the poloxamer 188 polymeric distribution (such as those greater than 13,000 Daltons) would be more likely to be cleared from the circulation at a slower rate than those of smaller size.

For the LCMF preparations, however, the presence of HMW components in the distribution does not result in a longer circulating species (i.e., a species with a half-life more than 5-fold longer than the main peak). For example, HMW impurities greater than 13,000 Daltons in an LCMF preparation generally constitute no more than 1.5% by weight of the total component. When the LCMF preparation is administered to a subject, these HMW impurities do not result in a circulating half-life that is more than 5.0-fold longer than the half-life of the main component in the distribution, and generally no more than 4.0-fold, 3.0-fold, 2.0-fold, 1.5-fold longer. When the LCMF preparation is administered to a subject, they do not result in any component with a circulating half-life that is substantially more (i.e., more than 5-fold) than or is more than the main component in the distribution (see, e.g., FIGS. 7A and 7B).

In the LCMF preparation, the HMW components can be either increased or decreased compared to other existing purified P-188 preparations. For example, an LCMF poloxamer provided herein includes P-188 poloxamers in which there are no more than 1.3% high molecular weight components greater than 13,000 Daltons, such as no more than 1.2%, 1.1%, 1.0% or less. In particular examples provided herein, an LCMF poloxamer provided herein includes P-188 poloxamers in which there are less than 1.0% by weight high molecular weight components greater than 13,000 Daltons, and generally less than 0.9%, 0.8%, 0.7%, 0.6%, 0.5% or less.

The LCMF poloxamer provided herein can be prepared by methods as described herein below in Section D, and in particular in Section D.1.b (see e.g., FIG. 3). In view of the description and exemplification of the properties of the LCMF poloxamer, those of skill in the art can envision other methods for producing an LCMF poloxamer. For example, an LCMF poloxamer provided herein is made by a method that includes:

a) introducing a poloxamer solution into an extractor vessel, where the poloxamer is dissolved in a first alkanol to form a solution;

b) contacting the poloxamer solution with an extraction solvent comprising a second alkanol and supercritical carbon dioxide under a temperature and pressure to maintain the supercritical carbon dioxide for a first defined period, wherein:

the temperature is above the critical temperature of carbon dioxide but can typically range between 35° C.-45° C.;

the pressure is 220 bars to 280 bars; and the alkanol is provided at an alkanol concentration that is 7% to 8% by weight of the total extraction solvent; and c) increasing the concentration of the second alkanol in step b) in the extraction solvent a plurality of times in gradient steps over time of the extraction method, wherein:

each plurality of times occurs for a further defined period; and in each successive step, the alkanol concentration is increased 1-2% compared to the previous concentration of the second alkanol; and d) removing the extraction solvent from the extractor vessel to thereby remove the extracted material from the raffinate poloxamer preparation.

D. EXTRACTION METHODS FOR PURIFYING POLOXAMERS

Provided herein are supercritical fluid extraction (SFE) and high-pressure procedures for purifying poloxamers such that the purified polymer is more homogenous with regard to structure (diblock, triblock, etc.), the percentage of molecules without unsaturation, the distribution of molecular weights, and distribution of hydrophobic/hydrophilic (HLB) ratios. The tunability of the processes can be leveraged to effectively remove extraneous components and can be adjusted over time, which can increase the yield of the purified product. The method provided herein uses a solvent system that is variable in its solvation characteristics in order to selectively remove various substances. The methods provide an exemplary way to produce the LCMF poloxamer 188 product, which has the above properties.

Methods herein provide poloxamer preparations that differ from those produced by prior methods. These include the LCMF poloxamer 188 preparation that, upon administration, does not give rise to longer circulating material observed with purified poloxamer 188, such as that described in U.S. Pat. No. 5,696,298. The LCMF poloxamer 188 has the molecule size distribution similar to the purified poloxamer 188, but the component molecules produce a preparation that is more hydrophilic than purified poloxamer.

The absence of the long circulating material (LCM) improves the properties of the poloxamer, including faster clearance and other such improved pharmacological properties by virtue of the elimination of the longer circulating material. The methods provided herein eliminate unwanted components in a poloxamer preparation, and thereby prepare a more homogenous or uniform poloxamer preparation that exhibits desired therapeutic activity while minimizing or reducing undesired activities. Because commercially available poloxamers have been reported to exhibit toxicity as well as variation in biological activity, a poloxamer preparation that is more uniform and homogenous has reduced toxicity but retains therapeutic efficacy of the main copolymer component.

Provided herein are methods for preparing such poloxamers, and provided are the resulting poloxamers, including the LCMF poloxamer 188. The methods provided herein, in addition to resulting in poloxamer preparations in which low molecular weight (LMW) components are reduced or removed, also result in long circulating material free (LCMF) preparations that are reduced or removed for any component that is or gives rise to a circulating material in the plasma or blood as described herein. Hence, also provided herein are LCMF preparations of poloxamers, and in particular LCMF poloxamer 188. The LCMF poloxamer 188 provided herein can be used for all of the uses known for poloxamer 188.

Provided herein are extraction methods for purifying poloxamers, such as P188, in order to remove or reduce components other than the main component, and thereby decrease the molecular diversity of the preparation. For example, the methods provided herein can remove or reduce LMW substances in a poloxamer. It is also found herein, that, in addition to removing or reducing LMW substances, particular methods provided herein also can remove or reduce components in a poloxamer preparation that is or gives rise to a longer circulating material that has a half-life that is substantially longer than the half-life of the main component in the distribution. The degree of extraction, and components that are extracted, are controlled by the particular temperature, pressure and alkanol concentration employed in the methods as described herein.

The methods provided herein employ a supercritical or subcritical extraction solvent in which the solvent power is controlled by manipulation of temperature, pressure in the presence of a co-solvent modifier. It is found that carbon dioxide is not a particularly efficient extraction solvent of poloxamers, such as P188, but that the presence of a polar co-solvent, such as an alkanol, as a modifier increases the solubilizing efficiency of $CO_2$ in the extraction solvent. In particular, the methods provided herein are performed in the presence of a polar co-solvent, such as an alkanol, whose concentration is increased in a gradient fashion (e.g., a step-wise gradient or a continuously escalating gradient) as the extraction process progresses. It is found that by employing an alkanol co-solvent whose concentration is increased in this manner, the removal of impurities can be increased, and to a much greater extent than when carbon dioxide is used alone. For example, an extraction method that uses carbon dioxide alone is not capable of removing the unwanted components, such as the LMW components and HMW components as described herein, to the same degree as that achieved by the provided method.

In the methods provides herein for purifying a poloxamer using supercritical fluid extraction, the LMW components or impurities of a poloxamer distribution can be selectively removed with a lower alkanol concentrations (e.g., methanol) and higher pressure than other HMW components in the distribution. As described further below, by increasing the solubilizing power of the extraction solvent, for example by carefully controlling the pressure and concentration of polar solvent, such as an alkanol (e.g., methanol), it also is possible to remove other impurities. In particular, a method is provided employing a gradient of higher concentrations of an alkanol (such as methanol), alone or in conjunction with a decrease in the pressure, that results in the removal of components (e.g., HMW components) in a poloxamer distribution such that, when the resulting product is administered to a subject, it does not result in a longer circulating material in the plasma that is observed with the previous P-188 products.

There, however, can be a tradeoff with respect to the yield of poloxamer. Generally, as the concentration of the alkanol (e.g., methanol) co-solvent increases, the solvating power of the extraction solvent is increased so that more compounds are solubilized and the degree of extraction increases. By increasing the concentration of extraction solvent in a gradient fashion, the reduction of poloxamer yield is minimized, while the purity of the final product is maximized. Typically, the methods provided herein achieve a yield such that the amount of the extracted or purified polymer obtained by the method is at least 55%, 60%, 70%, 75%, 80%, 85%, 90% or more of the starting amount of the poloxamer prior to performance of the method. The resulting poloxamers, however, exhibit a substantially greater purity with a higher percentage of main component in the distribution than the starting material, and without impurities that exhibit toxic side effects or that can result in a longer circulating material in the plasma when administered.

The methods can be performed on any poloxamer in which it is desired to increase the purity, for example by decreasing or reducing components that are undesired in the distribution of a polymer. It is within the level of a skilled artisan to choose a particular poloxamer for purification in this manner. Undesired components include any that are or give rise to a material that is toxic or that has a biological activity that is counter or opposing to the desired activity. For example, the poloxamer can be one in which it is desired to reduce or remove LMW components in the poloxamer, for example, any LMW components that result in acute renal side effects, such as elevated creatinine, when administered. The poloxamer also can be one that contains any component, such as a HMW component, that, when administered, is or gives rise to a material that has a half-life in the blood that is different (e.g., longer) than the half-life of the main component in the distribution of the polymer. Such components can increase blood viscosity and red blood cell aggregation, and hence are undesired.

Exemplary of poloxamers for use in the methods include, but are not limited to, poloxamer 188, poloxamer 331 and poloxamer 407. Typically, the poloxamer is one in which the average molecular weight of the main component is within or about 4,700 Da to 12,800 Da, such as generally 7,680 Da to 9,510 Da, for example generally 8,400-8,800 Da. In particular, the poloxamer is P188.

For example, the extraction methods provided herein can be employed to purify a P188 preparation, where the P188 preparation has the following chemical formula:

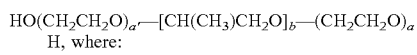
H, where:

the hydrophobe represented by ($C_3H_6O$) has a molecular weight of approximately 1,750 Daltons and an average molecular weight of 7,680 to 9,510 Da, such as generally approximately 8,400-8,800 Daltons. The polyoxyethylene:polyoxypropylene:polyoxyethylene weight ratio of P188 is approximately 4:2:4. P188 has a weight percent of oxyethylene of 81.8±1.9%, and an unsaturation level of 0.026±0.008 mEq/g. P188 preparations for use in the extraction methods herein include commercially available preparations. These include, but are not limited to, Pluronic® F68 (BASF, Florham Park, N.J.) and RheothRx® (developed by Glaxo Wellcome Inc.).

In practicing the extraction methods provided herein, the methods include: a) providing a poloxamer (e.g., P188) solution into an extractor vessel, where the poloxamer solution is prepared by dissolving the poloxamer in a first solvent to form the solution; b) admixing an extraction solvent containing a supercritical liquid (e.g., supercritical carbon dioxide) or sub-critical fluid (e.g., high pressure carbon dioxide) and a co-modifier solvent with the solution to form an extraction mixture, wherein the concentration of the co-modifier solvent in the extraction solvent is increased over the time of extraction method; and c) removing the extraction solvent from the extractor vessel to thereby remove the impurities (e.g., LMW and/or other components), from the poloxamer. In the method, the step of dissolving the poloxamer solution in the first solvent can occur prior to charging the solution into an extraction vessel or at the time of charging the solution into an extraction vessel. For example, the poloxamer is dissolved in a separate vessel and then the solution is added to the extraction vessel.

The method can be a high pressure or supercritical fluid extraction method. Typically, the method is performed using supercritical fluid extraction (SFE) using a supercritical liquid in the extraction solvent. A supercritical liquid is any liquid that is heated above the critical temperature and compressed to above the critical pressure. For example, carbon dioxide has a critical temperature of 31.1° C. and a critical pressure of 73.8 bars. Thus, extraction conditions for a supercritical carbon dioxide are above the critical temperature of about 31° C. and critical pressure of about 74 bars. In contrast, high pressure extraction can be achieved under sub-critical conditions in which the pressure exceeds the critical pressure, but the temperature does not exceed the critical temperature.

1. Processes

A. For Extraction Supercritical Methods

In certain instances, the supercritical fluid extraction process employed in the methods provided herein is essentially a solvent extraction process using a supercritical fluid as the solvent. With supercritical fluid, multi-component mixtures can be separated by exploiting the differences in component volatilities and the differences in the specific interactions between the component mixture and supercritical fluid solvent (solvent extraction). In the supercritical region of the phase diagram, a compressible fluid such as carbon dioxide exhibits liquid-like density and much increased solvent capacity that is pressure dependent.

The supercritical fluid exhibits a number of highly advantageous characteristics making it a superior solvent. For example, the tunable solvent power of a supercritical fluid changes rapidly around critical conditions within a certain range. The solvent power of the supercritical fluid, and thus the nature of the component that can be selectively removed during extraction, can be fine-tuned by varying the temperature and pressure of the supercritical fluid solvent.

Another beneficial property of various supercritical fluids is the difference in their critical temperatures and pressures. Each supercritical fluid has a range of solvent power. The tunable solvent power range can be selected by choosing an appropriate supercritical fluid.

In addition to its unique solubility characteristics, supercritical fluids exhibit certain physicochemical properties making them more useful. For example, supercritical fluids exhibit liquid-like density, and possess gas-like transport properties such as diffusivity and viscosity. These characteristics also change rapidly around the critical region. Supercritical fluids also have zero surface tension. Since most of the useful supercritical fluids have boiling points around or below ambient temperature, the solvent removal step after purification is simple, energy efficient and does not leave any residual solvents.

The use of solid matrices during extraction provides an additional dimension for a fractionation parameter. A suitable solid matrix provides solvent-matrix and solute-matrix interactions in addition to solute-solvent interactions to enhance the fractionation resolution. The desirable transport properties of supercritical fluids make the process easily scalable for manufacturing. Heat transfer and mass transfer characteristics do not significantly change upon process scale up with supercritical fluid extraction processes. Since the extraction process conditions, such as pressure, temperature, and flow rate, can be precisely controlled, the purification process is reproducible in addition to highly tunable.

In such a method, the extraction solvent can contain a supercritical liquid (e.g., supercritical carbon dioxide), as well as another co-modifier solvent, generally an alkanol, that is increased over time in the extraction. As described above, the presence of the co-modifier solvent can improve the solubility of solutes, such as higher molecular weight or more non-polar solutes, and thereby increase their extraction in the method.

For example, the method provided herein can include: a) providing or introducing a poloxamer (e.g., a poloxamer 188) solution into an extractor vessel, wherein the poloxamer solution is prepared by dissolving the poloxamer in a first alkanol to form the solution; b) admixing an extraction solvent containing a second alkanol and a supercritical liquid, under high pressure and high temperature sufficient to create supercritical liquid conditions, with the solution to form an extraction mixture, wherein the concentration of the second alkanol in the extraction solvent is increased over the time of extraction method; and c) removing the extraction solvent from the extractor vessel to thereby remove the impurities (e.g., LMW component or other components) from the poloxamer preparation. The first and second alkanol can be the same or different. In the method, the step of dissolving the poloxamer solution in the first solvent can occur prior to charging the solution into an extraction vessel or at the time of charging the solution into an extraction vessel. For example, the poloxamer is dissolved in a separate vessel and then the solution is added to the extraction vessel.

An exemplary process is detailed in FIG. 1. FIG. 1 depicts a process (100) that removes impurities (e.g., LMW component or other components) from a poloxamer preparation. The extraction system is pressurized, as shown in step 105, typically prior to dispensing a first alkanol into the feed mix tank, as shown in step 110. The system is heated to a temperature suitable for the extraction process. The temperature is typically a temperature that is above the critical temperature of the supercritical liquid (e.g., carbon dioxide). Generally, the temperature is approximately 40° C.

Any suitable alkanol or combination of alkanols can be used in the methods provided herein. Examples of suitable alkanols include, but are not limited to, methanol, ethanol, propanol and butanol. For example, the method provided herein includes an extraction method as described above, wherein the first and the second alkanol are each independently selected from methanol, ethanol, propanol, butanol, pentanol and a combination thereof. In some embodiments, the first alkanol is methanol. In certain instances, methanol is selected as the purification solvent and is the second alkanol in practice of the method. A skilled artisan will appreciate that methanol has relatively low toxicity characteristics. Moreover, methanol has good solubility for poloxamer 188.

The first alkanol (e.g., methanol) is used to form a poloxamer solution according to step 115 in process 100. A poloxamer, such as a P188 preparation, is dispensed into the feed tank and is stirred until mixed with the first alkanol. The amount of poloxamer that is added to the feed tank is a function of the scalability of the extraction method, the size of the extraction vessel, the degree of purity to achieve and other factors within the level of a skilled artisan. For example, non-limiting amounts of poloxamer (e.g., P188) per mL of an extraction vessel can be 0.1 kg to 0.5 kg or 0.2 kg to 0.4 kg. In some examples, in methods of extraction using a 3 L extraction vessel, non-limiting amounts of poloxamer (e.g., P188) can be 0.6 kg to 1.2 kg, such as 0.8 kg to 1.0 kg. In another example, in methods of extraction using a 12 L extraction vessel, non-limiting amounts of poloxamer (e.g., P188) can be 1.5 kg to 5 kg, such as 2 kg to 4 kg. In a further example, in methods of extraction using a 50 L extraction vessel, non-limiting amounts of poloxamer (e.g., P188) can be 8 kg to 20 kg, such as 10 kg to 16 kg or 12 kg to 15 kg. Variations in the amounts are contemplated depending on the particular applications, extraction vessel, purity of the starting material and other considerations within the level of a skilled artisan.

Any suitable ratio of poloxamer and alkanol is contemplated for use in the methods provided herein. The ratio of poloxamer to alkanol, by weight, can be, for example, from about 4:1 to about 1:4, such as from about 3:1 to about 1:3, 2:1 to about 1:2, 1:1 to 4:1 or 1:2 to 1:4. For example, the ratio of poloxamer to alkanol, by weight, can be about 4 to 1, or about 3 to 1, or about 2 to 1, or about 1 to 1, or about 1 to 2, or about 1 to 3 or about 1 to 4. For example, a quantity of poloxamer, such as P188, can be mixed with an equal quantity, by weight, of alkanol (e.g., methanol). A quantity of poloxamer, such as P188, can be mixed with a lesser amount, by weight, of alkanol, such as half the amount, by weight, of alkanol (e.g., methanol). One of skill in the art will appreciate that the appropriate poloxamer to alkanol ratio will depend on poloxamer properties, such as solubility, in a given alkanol.

After forming a poloxamer/alkanol mixture, all or part of the mixture is pumped into the extractor as shown in step 120. In such examples, the process of preparing the poloxamer solution is performed in a separate vessel from the extractor. A skilled artisan will appreciate that the poloxamer can also be introduced as a solid into the extractor prior to mixing with the first alkanol. Thus, the process of preparing the poloxamer solution can be made directly in the extractor vessel.

The extractor is then pressurized and the extraction solvent is introduced into the extractor as shown in step 125 of process 100. The extraction solvent contains the supercritical liquid. Examples of supercritical liquids include, but are not limited to, carbon dioxide, methane, ethane, propane, ammonia, Freon®, water, ethylene, propylene, methanol, ethanol, acetone, and combinations thereof. In some embodiments, the supercritical liquid under pressure is a member selected from carbon dioxide, methane, ethane, propane, ammonia and the refrigerants sold as freons. In some embodiments, the supercritical liquid under pressure is carbon dioxide ($CO_2$).

The extraction occurs under high pressure and high temperature to maintain a supercritical liquid condition (e.g., supercritical carbon dioxide). Typically, these are kept constant. At this pressure and temperature, the supercritical liquid (e.g., supercritical carbon dioxide) is provided at a substantially constant flow rate. The flow rate can be varied between 0.5 kg/h to 600 kg/h, such as 1 kg/h to 400 kg/h, 1 kg/h to 250 kg/h, 1 kg/h to 100 kg/h, 1 kg/h to 50 kg/h, 1 kg/h to 20 kg/h, 1 kg/h to 10 kg/h, 10 kg/h to 400 kg/h, 10 kg/h to 250 kg/h, 10 kg/h to 100 kg/h, 10 kg/h to 50 kg/h, 10 kg/h to 20 kg/h, 20 kg/h to 400 kg/h, 20 kg/h to 250 kg/h, 20 kg/h to 100 kg/h, 20 kg/h to 50 kg/h, 50 kg/h to 400 kg/h, 50 kg/h to 250 kg/h, 50 kg/h to 100 kg/h, 100 kg/h to 400 kg/h, 100 kg/h to 200 kg/h or 200 kg/h to 400 kg/h, each inclusive. For example, the flow rate is 20 kg/h to 100 kg/h, inclusive, such as generally about or 100 kg/h.

Any suitable temperature that maintains the supercritical liquid in the supercritical state can be used to conduct the extraction processes. For example, the critical temperature of carbon dioxide is about 31° C. Thus, the extractor vessel is kept at a temperature greater than 31° C. In some embodiments, the extractor vessel has a temperature of 32° C. to 80° C., and generally about 32° C. to 60° C. or 32° C. to 60° C., each inclusive. For example, the temperature can be a temperature that is no more than 35° C., 36° C., 37° C., 38° C., 39° C., 40° C., 41° C., 42° C., 43° C., 44° C., 45° C., 50° C. or 60° C. Generally the temperature is greater than 31° C. but no more than 40° C. One of skill in the art will appreciate that the temperature can be varied, depending in part on the composition of the extraction solvent as well as the solubility of a given poloxamer in the solvents employed in the process.

Any suitable pressure can be used in the methods. When supercritical fluid extraction is employed, the system is pressurized at a level to ensure that the supercritical liquid remains at a pressure above the critical pressure. For example, the critical pressure of carbon dioxide is about 74 bars. Thus, the extractor vessel is pressurized to greater than 74 bars. The particular degree of pressure can alter the solubility characteristics of the supercritical liquid. Therefore, the particular pressure chosen can affect the yield and degree of extraction of impurities. Typically, the extractor vessel is pressurized in a range of 125 to 500 bars. In some embodiments, the extractor vessel is pressurized in a range of 200 bars to 400 bars, 200 bars to 340 bars, 200 bars to 300 bars, 200 bars to 280 bars, 200 bars to 260 bars, 200 bars to 240 bars, 200 bars to 220 bars, 220 bars to 400 bars, 220 bars to 340 bars, 220 bars to 300 bars, 220 bars to 280 bars, 220 bars to 260 bars, 220 bars to 240 bars, 240 bars to 400 bars, 240 bars to 340 bars, 240 bars to 300 bars, 240 bars to 280 bars, 240 bars to 260 bars, 260 bars to 400 bars, 260 bars to 340 bars, 260 bars to 300 bars, 260 bars to 280 bars, 280 bars to 400 bars, 280 bars to 340 bars, 280 bars to 300 bars or 300 bars to 340 bars. For example, the extraction vessel can be pressurized at about or at least 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, or 400 bars, but generally no more than 500 bars. The extraction vessel can be pressurized, for example, at 310±15 bars.

Typically, in the methods provided herein, the extraction solvent introduced into the extraction vessel also contains an alkanol. Thus, the extraction solvent includes a second alkanol and a supercritical liquid under high pressure and high temperature. The second alkanol acts as a co-solvent modifier of the supercritical liquid to change the solvent characteristics of the supercritical liquid and improve extractability of the solute in the method. Any suitable alkanol or combination of alkanols, as described above, can be used as the second alkanol in the methods provided herein. As described above, in particular examples, the second alkanol is methanol.

Any suitable combination of the second alkanol and the supercritical liquid, such as any described above, can be used in the extraction solvent in the methods provided herein. In some embodiments, the extraction solvent includes methanol and carbon dioxide. The second alkanol typically is provided as a percentage (w/w) of the total extraction solvent that is 3% to 20%, and generally 3% to 15%, for example 5% to 12%, 5% to 10%, 5% to 9%, 5% to 8%, 5% to 7%, 7% to 15%, 7% to 12%, 7% to 10%, 7% to 9%, 7% to 8%, 8% to 15%, 8% to 12%, 8% to 10%, 8% to 9%, 9% to 15%, 9% to 12%, 9% to 10%, 10% to 15% or 10% to 12%, each inclusive. The flow rate (kg/h) of the alkanol is a function of the amount of alkanol introduced into the extractor.

For example, a suitable ratio of the alkanol (e.g., methanol) to supercritical liquid (e.g., carbon dioxide) can be selected based on the identity and purity of the poloxamer starting material, or based on other extraction parameters such as temperature or pressure. For example, the ratio of alkanol (e.g., methanol) to supercritical liquid (e.g., carbon dioxide) can be from about 1:100 to about 20:100. In some embodiments, the ratio of alkanol (e.g., methanol) to supercritical liquid (e.g., carbon dioxide) is from about 1:100 to about 15:100. In some embodiments, the ratio of alkanol (e.g., methanol) to supercritical liquid (e.g., carbon dioxide) is from about 2:100 to about 14:100. The ratio of alkanol (e.g., methanol) to supercritical liquid (e.g., carbon dioxide) can be about 3:100, or about 4:100, or about 5:100, or about 6:100, or about 7:100, or about 8:100, or about 9:100, or about 10:100, or about 11:100, or about 12:100, or about 13:100 or about 14:100.

In certain aspects, the extraction can be conducted in an isocratic fashion, wherein the composition of the extraction solvent remains constant throughout the extraction procedure. For example, the amount of supercritical liquid (e.g., carbon dioxide) and alkanol (e.g., methanol) are constant over the time of extraction, for example, by maintaining a constant flow rate of each. Alternatively, the composition of the extraction solvent can be varied over time, typically, by altering (e.g., increasing or decreasing) the amount of the supercritical liquid and/or alkanol components that make up the extraction solvent. Generally, the supercritical liquid (e.g., carbon dioxide) is kept constant while the concentration of the alkanol (e.g., methanol) in the extraction solvent is altered (e.g., increased or decreased) over time of the extraction. The concentrations of the components can be altered by adjusting the flow rate.

In aspects in which the composition of the extraction solvent can be varied over time, a method in which the second alkanol is increased as the extraction process progresses, either as a step-wise gradient or continuously escalating gradient, is beneficial to the method. In certain instances, commercial grade poloxamers have both high molecular weight components and low molecular weight components along with the main product or component. Low alkanol (e.g., methanol) concentrations in high pressure carbon dioxide extraction fluid can selectively remove low molecular weight components. The solubility of impurity enriched extractables, however, is low and it takes time to significantly reduce the low molecular weight components, making it less efficient. By increasing the alkanol concentration of the extraction solvent in a gradient fashion (either as a step-wise gradient or as a continuously escalating gradient), the amount of low molecular weight impurities that are extracted increases.

Also, higher alkanol (e.g., methanol) concentrations increase the solubility, and hence extraction, of higher molecular weight components. Thus, a gradient with successively higher alkanol (e.g., methanol) concentrations in the extraction solvent can progressively extract low molecular weight components, as well as eventually higher molecular weight components, or components that are less soluble. As a non-limiting example to illustrate this, it is believed that a lower alkanol (e.g., methanol) concentration of about 6.6% w/w can remove low molecular weight components. Increasing the concentration of alkanol by 1% to 3% will continue to effect extraction of low molecular weight components, but also result in removal of higher molecular weight components. A further increase in the concentration of alkanol by 1% to 3% will further remove these components as well as other components that have a higher molecular weight and/or were less soluble in the previous extraction solvents.

An extraction solvent with higher alkanol (e.g., methanol) concentrations, however, is not as selective because it provides more solubility for low molecular weight components, but also increases the solubility of other components including the main components. Therefore, the yield of purified product is reduced with high methanol concentrations. By increasing the concentration of the extraction solvent in a gradient fashion, as provided in methods herein, the reduction of poloxamer yield is minimized and the purity of the final product is maximized.

It was found that increasing the methanol concentration step-wise increases the loading capacity of the extractor, thereby increasing the throughput in a given extraction system. A two-phase system forms inside the extractor. A lower phase consists primarily of a mixture of poloxamer and methanol with some dissolved carbon dioxide. The extraction solvent (carbon dioxide with a lower methanol co-solvent fraction) permeates through the lower phase. An upper phase consists primarily of the extraction solvent and the components extracted from the poloxamer. The relative amount of the two phases depends upon the methanol concentration in the solvent flow. In a typical extraction system there is adequate head space for proper phase separation of the upper phase. Increasing the methanol co-solvent concentration step-wise during the extraction process leads to higher feed charge into the extractor.

For example, returning to process 100, the composition of the extraction solvent can be varied as shown in steps 130-140. In some embodiments, the percentage of alkanol (e.g., methanol) by weight of the extraction solvent is increased over the course of the method. The methanol content in a methanol/carbon dioxide mixture can be increased in a stepwise fashion or a continuous fashion as the extraction process progresses. In some embodiments, for example, the extraction process for a poloxamer (e.g., P188) starts using about 3% to about 10% by weight (w/w) of an alkanol (e.g., methanol) in an extraction solvent with a supercritical liquid (e.g., carbon dioxide), such as about 5% to about 10%, such as 6% to 8% (e.g., about 6.6% or 7.4%). After a defined period, the alkanol (e.g., methanol) content of the extraction solvent is raised about 1-3%, such as 1-2% (e.g., to 7.6% or 9.1%, respectively). The alkanol (e.g., methanol) content is again subsequently raised about 1-3% such as 1-2% (e.g., to 8.6% or 10.7%, respectively) during a final period. Any suitable solvent gradient can be used in the methods. For example, the alkanol (e.g., methanol) concentration in the supercritical liquid (e.g., carbon dioxide) can be increased from about 5% to about 20% over the course of extraction procedure. The alkanol (e.g., methanol) concentration in the supercritical liquid (e.g., carbon dioxide) can be increased from about 5% to about 20%, or from about 5% to about 15%, or from about 5% to about 10%. The alkanol (e.g., methanol) concentration in the supercritical liquid (e.g., carbon dioxide) can be increased from about 6% to about 18%, or from about 6% to about 12%, or from about 6% to about 10%. The alkanol (e.g., methanol) concentration in supercritical liquid (e.g., carbon dioxide) can be increased from about 7% to about 18%, or from about 7% to about 12%, or from about 7% to about 10%. The alkanol (e.g., methanol) concentration can be increased in any suitable number of steps. For example, the alkanol (e.g., methanol) concentration can be increased over two steps, or three steps, or four steps, or five steps over the course of the extraction procedure. A skilled artisan will appreciate that other solvent ratios and solvent gradients can be used in the extraction processes.

Time of extraction of the process provided herein can be for any defined period that results in a suitable extraction of material in the preparation while minimizing reductions in poloxamer yield and maximizing purity. The time is a function of the choice of pressure, temperature, second alkanol concentration, and process of providing the extraction solvent (e.g., isocratic or as a gradient of increasing alkanol concentration as described herein). Generally, the extraction proceeds for 5 hours to 50 hours, and generally 10 hours to 30 hours, or 15 hours to 25 hours, each inclusive, such as or about 15 hours or 24 hours. The higher the alkanol (e.g., methanol) concentration employed in the method, typically the shorter the time of the extraction. It also is understood that in examples in which a gradient of alkanol is employed in the method, the total time of extraction is divided as a function of the number of gradient steps in the procedure. The extraction in each gradient step can be for the same amount of time or for different times. It is within the level of a skilled artisan to empirically determine the times of extraction to be employed.

Samples can be collected during the extraction process to monitor the removal of substances or to determine if adjustment of extraction parameters, such as temperature or the composition of the extraction solvent, is necessary.

In particular, the methods can be used to purify P188. The process can be applied to other polymers as well. For example, in some embodiments, the methods provided herein provide a method for preparing a purified polyoxypropylene/polyoxyethylene composition. The method includes:

a) providing or introducing a polyoxypropylene/polyoxyethylene block copolymer solution into an extractor vessel that is dissolved in a first solvent to form the copolymer solution, wherein the first solvent is methanol, ethanol, propanol, butanol, pentanol or a combination thereof, and the composition comprises:

i) a polyoxypropylene/polyoxyethylene block copolymer having the formula $HO(CH_2CH_2O)_a$—$[CH(CH_3)CH_2O]_b$—$(CH_2CH_2O)_aH$, the mean or average molecular weight of the copolymer is from about 4,000 to about 10,000 Da; and ii) a plurality of low molecular weight substances having a molecular weight of less than 4,500 Da, wherein the plurality of low molecular weight substances constitutes more that 4% of the total weight of the composition;

b) adding a second solvent to form an extraction mixture, wherein the second solvent contains a supercritical liquid under high pressure and high temperature and an alkanol that is methanol, ethanol, propanol, butanol, pentanol or a combination thereof, and the concentration of the second solvent in the extraction solvent is increased over the time of extraction method; and c) allowing the extraction mixture to separate to form a plurality of phases comprising a raffinate phase and an extract phase, wherein the raffinate phase and extract phase are separately removed or isolated.

In some cases of the above method, the mean or average molecular weight of the copolymer is from about 7,680 to 9,510 Da, such as generally 8,400-8,800 Da, for example about or at 8,400 Da. In the method, the copolymer solution can be formed in the extractor vessel by the addition of the copolymer and by adding a first solvent to form a solution or a suspension of the copolymer, wherein the first solvent comprises an alkanol selected from the group consisting of methanol, ethanol, propanol, butanol, pentanol and a combination thereof. Alternatively, the addition of the first solvent to the copolymer to form a copolymer solution can be in a separate vessel and the copolymer solution, which is dissolved in the first solvent, is provided or introduced (i.e. charged) into the extractor vessel. In some cases, prior to step c) the method includes stirring the extraction mixture under high pressure and high temperature to extract impurities (e.g., low molecular weight extractable components and other components) from the copolymer composition.

b. High Pressure Methods

The method provided herein to purify a poloxamer (e.g., P188) can be a high pressure fluid extraction method with mixed solvent systems. One of the solvents in the mixed system is a gaseous solvent that can be compressed to liquid at moderate pressures, such as carbon dioxide. For example, the solvent power of methanol or ethanol can be modified with high pressure carbon dioxide (although not necessarily supercritical carbon dioxide i.e., sub-critical) to give the precise solvating power required to selectively remove different fractions of poloxamers.

In such a method, the extraction solvent contains carbon dioxide that is provided under sub-critical conditions, as well as another solvent that is increased over time in the extraction. Accordingly, some embodiments of methods provided herein provide an extraction method for removing impurities in a poloxamer preparation (e.g., low molecular weight components), wherein the method includes:

a) providing or introducing a poloxamer into an extractor vessel that is dissolved in a first solvent to form a solution, wherein the first solvent is selected from among alcohols, aliphatic ketones, aromatic ketones, amines, and mixtures thereof;

b) admixing an extraction solvent with the solution to form an extraction mixture, wherein the extraction solvent comprises high-pressure carbon dioxide and the solvent, and the concentration of the solvent in the extraction solvent is increased over the time of extraction method; and c) removing the extraction solvent from the extractor vessel to thereby remove the low molecular weight impurities from the poloxamer.

The first and second solvent can be the same or different. In the method, the step of dissolving the poloxamer solution in the first solvent can occur prior to providing or introducing the solution into an extraction vessel or at the time of providing or introducing the solution into an extraction vessel. For example, the poloxamer is dissolved in a separate vessel and then the solution is added to the extraction vessel.

In aspects of the method, the extraction solvent is under sub-critical conditions. In this process, one of the solvents is preferably a gas at room temperature (or close to room temperature) that can be compressed to a liquid at high pressures. Suitable gases that can be compressed to liquids are carbon dioxide, methane, ethane, propane, ammonia, and refrigerants sold as Freon®. A typical solvent pair is chosen in such a way that one is a solvent for the component to be removed by extraction, while the other liquid is a non-solvent, or vice-versa. The solvating capacity of the solvent pair is primarily controlled by the ratio of the solvents in the mixture. By passing the solvent pair through the product containing the substances, the relatively more soluble component can be extracted. Gaseous solvents can be pressurized at any suitable sub-critical pressure. For example, carbon dioxide can be employed at a pressure of from about 25 bars to about 100 bars. The pressure can be about 25, 30, 35, 40, 45, 50, 55, 60, 65, 70, 75, 80, 85, 90, 95, or 100 bars. In some embodiments, the pressure is from about 60 to about 85 bars. In some embodiments, the pressure is about 75 bars.

Any suitable temperature can be used to conduct the extraction processes. In some embodiments, the extractor vessel has a temperature of 10° C. to 80° C. The temperature can be, for example, about 10° C., or about 15° C., or about 20° C., or about 25° C., or about 30° C., or about 35° C., or about 40° C., or about 45° C., or about 50° C., or about 55° C., or about 60° C., or about 65° C., or about 70° C., or about 75° C., or about 80° C. In some embodiments, the extractor vessel has a temperature of from about 20° C. to about 50° C. When purifying poloxamer 188, for example, the extractor vessel can have a temperature of from about 20° C. to about 60° C. (e.g., about 40° C.). Other temperatures can be suitable for purification of poloxamer 188 depending on the extraction apparatus and the chosen extraction parameters. One of skill in the art will appreciate that the temperature can be varied, depending in part on the composition of the extraction solvent as well as the solubility of a given poloxamer in the solvents employed in the process.

Similar to supercritical fluid extraction methods discussed above, the extraction can be conducted in an isocratic fashion, wherein the composition of the extraction solvent remains constant throughout the extraction procedure. For example, the amount of carbon dioxide and solvent (e.g., methanol) in the extraction solvent are constant over the time of extraction, for example, by maintaining a constant flow rate of each. Alternatively, the composition of the extraction solvent can be varied over time, typically by altering (e.g., increasing or decreasing) the amount of the carbon dioxide and/or other solvent (e.g., methanol) that make up the extraction solvent. Generally, the carbon dioxide is kept constant while the concentration of the other solvent (e.g., methanol) in the extraction solvent is altered (e.g., increased or decreased) over time of the extraction. The concentrations of the components can be altered by adjusting the flow rate. The particular concentration of solvent, and the gradient of concentrations employed, can be similar to those discussed above with respect to the supercritical extraction methods. It is within the level of a skilled artisan to adjust concentrations and extraction time appropriately to achieve a desired purity or yield.

Samples can be collected during the extraction process to monitor the removal of substances or to determine if adjustment of extraction parameters, such as temperature or the composition of the extraction solvent, is necessary.

In particular, the methods can be used to purify P188. The process can be applied to other polymers as well. The benefits of the mixed solvent system include effective removal of high molecular weight (HMW) substances and/or low molecular weight (LMW) substances using the mixed system.

In certain embodiments, the provided methods provide a method for preparing a purified polyoxypropylene/composition. The method includes:

a) providing or introducing a polyoxypropylene/polyoxyethylene block copolymer composition into an extractor vessel that is dissolved in a first solvent to form the copolymer solution, wherein the first solvent is an alcohol, aliphatic ketone, aromatic ketone, amines and mixtures thereof, and the composition contains:
  i) a polyoxypropylene/polyoxyethylene block copolymer wherein the mean or average molecular weight of the copolymer is from about 4,000 to about 10,000 Da; and
  ii) a plurality of low molecular weight substances having a molecular weight of less than 4,000 Da, wherein the plurality of low molecular weight substances constitutes more that 4% of the total weight of the composition;

b) adding a second solvent to form an extraction mixture, wherein the second solvent comprises high-pressure carbon dioxide and the first solvent, and the concentration of the first solvent in the extraction solvent is increased over the time of extraction method; and c) allowing the extraction mixture to separate to form a plurality of phases including a raffinate phase and an extract phase, and the raffinate phase and extract phase are separately removed or isolated.

When the poloxamer is a poloxamer 188 that is purified, the mean or average molecular weight of the copolymer is from about 7,680 to 9,510 Da, such as generally 8,400-8,800 Da, for example about or at 8,400 Da. In the method, the copolymer solution can be formed in the extractor vessel by the addition of the copolymer and by adding a first solvent to form a solution or a suspension of the copolymer, wherein the first solvent comprises an alkanol selected from the group consisting of methanol, ethanol, propanol, butanol, pentanol and a combination thereof. Alternatively, the addition of the first solvent to the copolymer to form a copolymer solution can be in a separate vessel and the copolymer solution, which is dissolved in the first solvent, is provided or introduced (i.e. charged) into the extractor vessel. In some cases, prior to step c) the method includes stirring the extraction mixture under high pressure and high temperature to extract impurities (e.g., low molecular weight extractable components and other components) from the copolymer composition.

In certain aspects, this approach does not have the density variation and permeability characteristics of the supercritical fluid extraction process. The solvent recycling is easy and energy efficient. In a typical high pressure extraction, the exit stream containing the extracted component is subjected to lower pressure that causes phase separation and separation of the more volatile solvent as a gas. This leaves the other solvent enriched with the extracted component. The extraction process continues until the extractable component is substantially depleted from the mixture. The gaseous solvent is compressed back into liquid and is available for continued extraction. This solvent recycling process is efficient because the compressible solvent is selected to have complete separation from the solvent mixture with minimum change in the pressure.

2. Extraction Vessel and System

Figure 4:
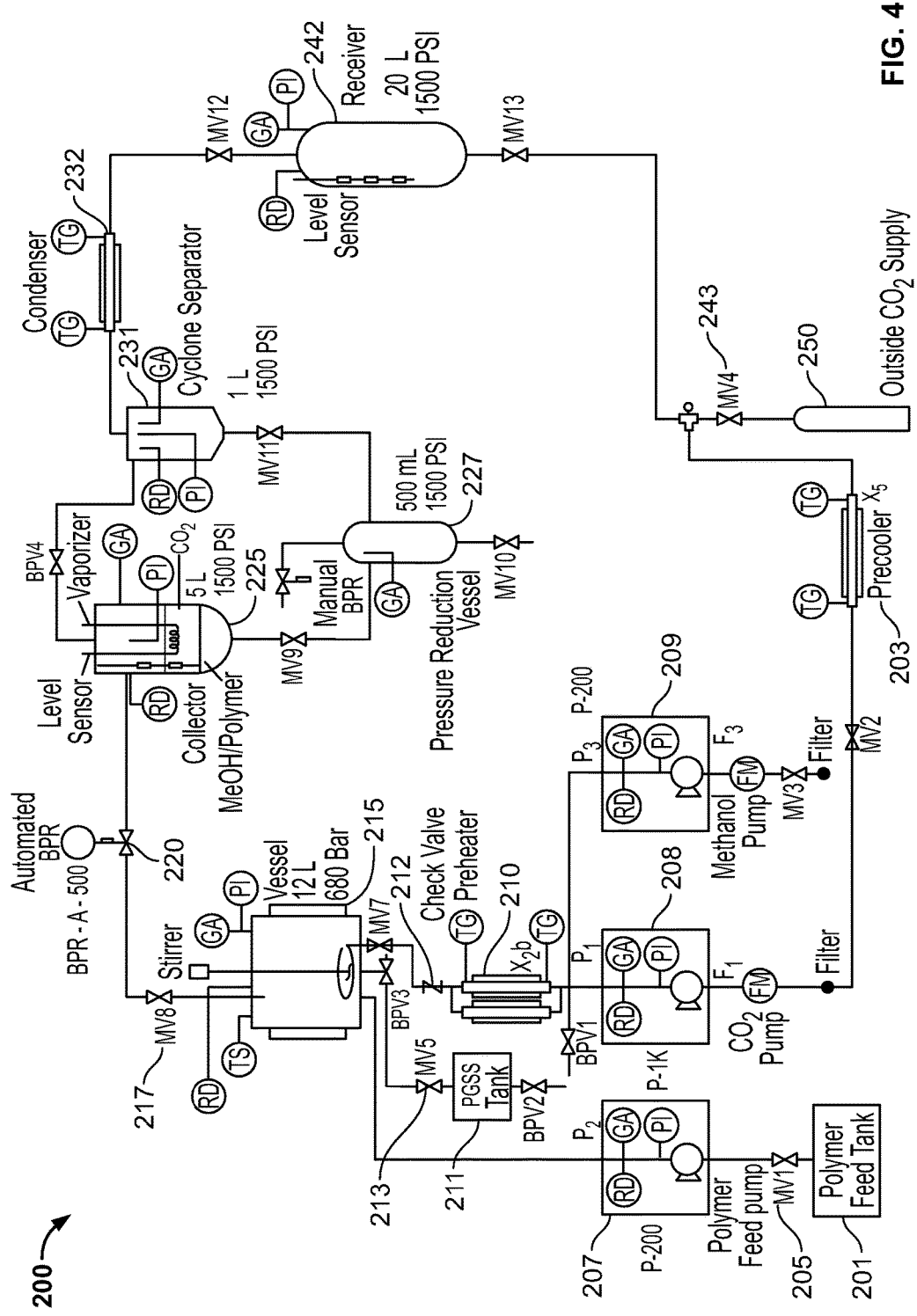
FIG. 4 shows an extraction apparatus useful in the methods provided herein.

For any of the methods provided herein, system 200 in FIG. 4 represents one embodiment for practice of the provided methods. System 200 is one system that can be used to extract impurities (e.g., LMW substances and/or other components) from the poloxamers using supercritical fluids or sub-supercritical methods. Polymer feed pump 201 is charged with a poloxamer (e.g., P188) to be purified. Poloxamer is transported into polymer feed tank 207 through valve 205. The extractor vessel 215 is used to remove the extracted impurities from the sample, such as LMW substances or other components from the poloxamer. Carbon dioxide (or other supercritical liquid or sub-supercritical liquid) pump 208 is charged with carbon dioxide from outside carbon dioxide supply 250 through valve 243 and pre-cooler 203. Carbon dioxide is pumped from pump 208 into heat exchanger 210 and then into extractor 215. Methanol (or other suitable solvents) is pumped into extractor 215 through pump 209. In such embodiments, methanol and carbon dioxide extract impurities, such as LMW substances or other components, from the poloxamer in extractor 215. After extraction, the purified poloxamer mixture is discharged and collected via rapid depressurization processing. The extracted components are isolated from the solvent stream using collector 225, pressure reduction vessel 227, and cyclone separator 231. Carbon dioxide vapor released during collection in collector 225 can be liquefied and recycled using condenser 232.

In some embodiments, the extraction apparatus can include a solvent distribution system that contains particles of certain shapes forming a "fluidized" bed at the bottom of the extraction vessel. The bed can be supported by a screen or strainer or sintered metal disk. The particles used for the bed can be either perfectly shaped spheres or particles of irregular shape, such as pebbles. Having a smooth surface with less porosity or less surface roughness is preferred for easy cleaning. These advantages can be validated in a pharmaceutical manufacturing process.

The density of the particles forming the bed is selected to be higher than the solvent density so the bed remains undisturbed by the incoming solvent flow during the extraction process. The size of the particles can be uniform or can have a distribution of different sizes to control the packing density and porosity of the bed. The packing distribution arrangement is designed to provide for balanced, optimum extraction and subsequent coalescence of the solvent particles before exiting the extraction vessel. This facilitates maximum loading of the extractor with poloxamer charge. This can also maximize extraction efficiency, minimize the extraction time, and minimize undesirable carry-over of the purified product out of the extraction vessel.

Figure 5:
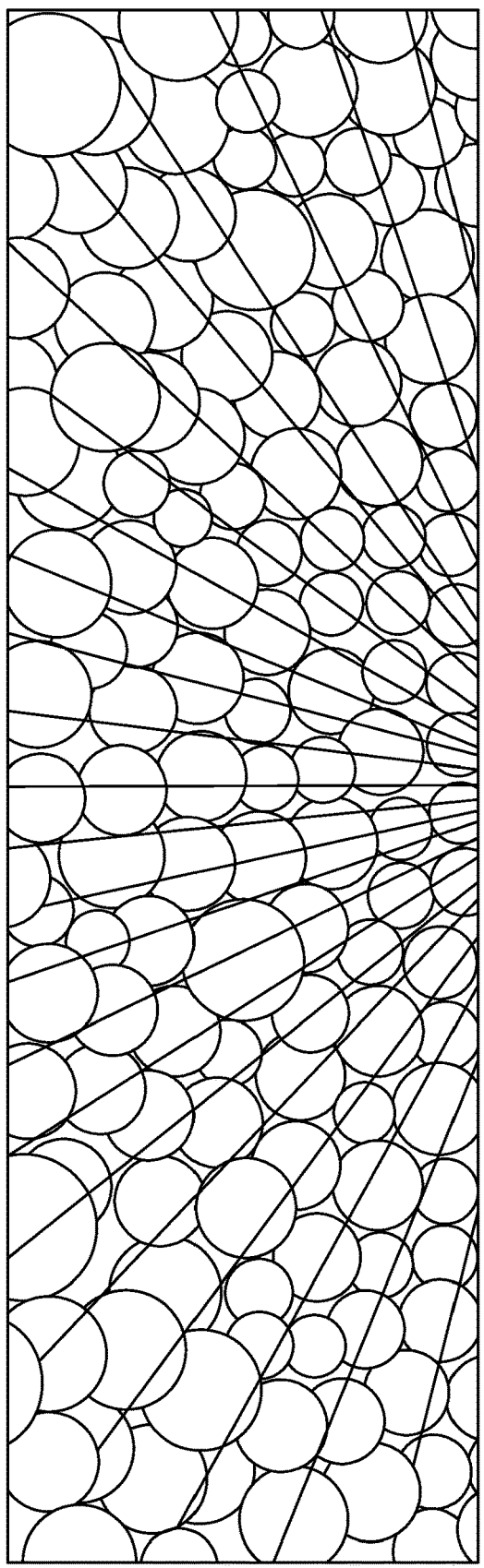
FIG. 5 shows one embodiment of the cross section of stainless spheres of different sizes in a solvent distribution bed.

The size of the spheres in the bed is selected based on one or more system properties including the dimensions of the extraction vessel, the residence time of the solvent droplets in the extraction vessel, and the ability of the solvent droplets to coalesce. The diameter of the spheres can range from about 5 mm to about 25 mm. The diameter can be an average diameter, wherein the bed contains spheres of different sizes. Alternatively, all of the spheres in the bed can have the same diameter. An example of the cross section of stainless steel spheres of different sizes in a solvent distribution bed is shown in FIG. 5.

Accordingly, an efficient solvent extraction apparatus is provided. The apparatus includes:

a) a distribution system at the bottom of the extractor, wherein the distribution system comprises a plurality of spheres; and b) a particle coalescence system at the top of the extractor.

In some embodiments, the plurality of spheres includes metallic spheres, ceramic spheres, or mixtures thereof. In some embodiments, the plurality of spheres are the same size. In some embodiments, the plurality of spheres include spheres of different sizes. In some embodiments, the particle coalescence system includes one or more members selected from a demister pad, a static mister, and a temperature zone.

3. Extraction and Removal of Extractants

Any of the methods provided herein can be performed as a batch method or as a continuous method. In some embodiments, the method is a batch method. A batch method can be performed with extraction vessels of various dimensions and sizes as described above. For example, the equipment train can contain a 120-L high pressure extractor. A poloxamer (e.g., P188) solution, which is a poloxamer dissolved in an appropriate solvent (e.g., an alkanol solvent, such as methanol), is provided or introduced into the extraction vessel. The extraction solvents, such as any described in the methods above (e.g., supercritical or high-pressure carbon dioxide and methanol) are independently and continuously pumped into the extraction vessel maintained at a controlled temperature, flow, and pressure. Substances are removed by varying the extraction solvent composition as described herein. Alternatively, the extraction process conditions such as temperature and pressure can also be varied independently or in combination. As described below, after substances are removed, the purified product is discharged into a suitably designed cyclone separator to separate the purified product from carbon dioxide gas. The product is dried to remove the residual alkanol solvent.

In some embodiments, the extraction method is a continuous method. In a typical continuous extraction, a poloxamer (e.g., P188) solution, which is a poloxamer dissolved in an appropriate solvent (e.g., an alkanol solvent, such as methanol), is loaded at the midpoint of a high pressure extraction column packed with a suitable packing material. The extraction solvent is pumped through the extraction column from the bottom in counter current fashion. The extracted material, such as LMW substances or other components, are removed at the top of the column while purified product is removed from the bottom of the column. The purified product is continuously collected at the bottom of the extractor column and periodically removed and discharged into a specially designed cyclone separator. The purified polymer particles containing residual methanol are subsequently dried under vacuum.

Depending on the level of purity desired in the purified poloxamer product, the extraction step can be repeated for a given batch. That is, additional portions of the extraction solvent can be introduced into the extractor vessel and removed until a sufficient level of poloxamer purity is obtained. Accordingly, some embodiments of methods provided herein provide extraction methods as described above, wherein after step c), the method further includes repeating steps b) and c). Steps b) and c) can be repeated until the poloxamer is sufficiently pure. For example, steps b) and c)

can be repeated one time, or two times, or three times, or four times, or five times, or in an iterative fashion.

When the poloxamer material is sufficiently pure, the product is prepared for further processing. In some embodiments, the product is handled according to process 100 as summarized in FIG. 1. The product can be discharged from the extractor vessel and collected in an appropriate receiver, as shown in step 145. The wet product can be sampled for testing with respect to purity, chemical stability, or other properties, as shown in step 150. The product can be dried by removing residual solvents under vacuum. Vacuum level can be adjusted to control drying rates. Drying can be conducted at ambient temperature, or at elevated temperatures if necessary. In general, the drying temperature is held below the melting point of the poloxamer. The wet product can be dried in a single lot or in smaller portions as sub-lots. As shown in steps 160-170, drying of the product can be initiated, for example on a sub-lot, under vacuum at ambient temperature. Drying can be then continued at higher temperatures and lower pressures as the process progresses. If necessary, for example if collection was made in sub-lots, any remaining portions of the wet product can be processed in a similar manner, as shown in step 175 of process 100. The resulting product, such as the various sub-lots that have been combined, are mixed in a suitable container, as shown in step 180, and the resulting product can be characterized, stored, transported, or formulated.

Advantageously, the methods disclosed herein effectively recycle carbon dioxide. In particular, supercritical carbon dioxide or high-pressure carbon dioxide can be recovered by subjecting the extract phase to changes in temperature and pressure. In certain embodiments, the methods employed herein have recycling efficiencies of greater than 80%, preferably greater than 90%, and most preferably greater than 95%.

In the methods provided herein (see, e.g., steps a)-c) above), the extract phase can be further processed. The methods further can include: passing the extract phase to a system consisting of several separation vessels; isolating the impurities (e.g., low molecular-weight impurities); processing the purified material or raffinate; and recovering the compressed carbon dioxide for reuse.

In any of the methods provided herein, various parameters can be assessed in evaluating the methods and resulting products. For example, parameters such as methanol concentration, gradient profile, temperature, and pressure can be assessed for process optimization. Processes and suitable conditions for drying wet raffinate, such as vacuum level, mixing mode, time, and temperature, also can be assessed.

4. Exemplary Methods for Preparation of Purified Poloxamers

The methods provided herein above result in the generation of particular purified poloxamer preparations, and in particular LCMF P188 preparations. In particular, the methods provided herein can be used to purify a P188 copolymer as described herein that has the formula: $HO(CH_2CH_2O)_{a'}$—$(CH_2CH(CH_3)O)_b$—$(CH_2CH_2O)_a H$, and a mean or average molecular weight of the copolymer that is from 7,680 to 9,510 Da, such as generally 8,400-8,800 Da, for example about or at 8,400 Da, and that contains a plurality of low molecular weight substances having a molecular weight of less than 4,000 Da, wherein the plurality of low molecular weight substances constitutes more that 4% of the total weight of the composition.

In some embodiments, the present methods generate purified poloxamers with less than about 4% low molecular weight components such as less than about 3%, 2% or 1%. Typically, the low molecular weight components include glycols, and volatile degradation impurities such as formaldehyde, acetaldehyde, propionaldehyde, acetone, methanol, and peroxides. In certain instances, the processes herein produce poloxamer substantially free of low molecular weight components, i.e., less than 4%, 3%, 2% or 1% of the foregoing components. The methods also can produce poloxamer substantially free of long circulating material, such that when the purified poloxamer is administered to a subject, there are no components in the poloxamer that are or give rise to a material that has a longer half-life in the blood or plasma more than 5.0-fold the half-life of the main component in the poloxamer distribution, such as generally no more than 4.0-fold, 3.0-fold, 2.0-fold, or 1.5-fold. The following discussion details an exemplary of method that produces such purified poloxamer.

a. Removal of Low Molecular Weight (LMW) Components

Figure 2:
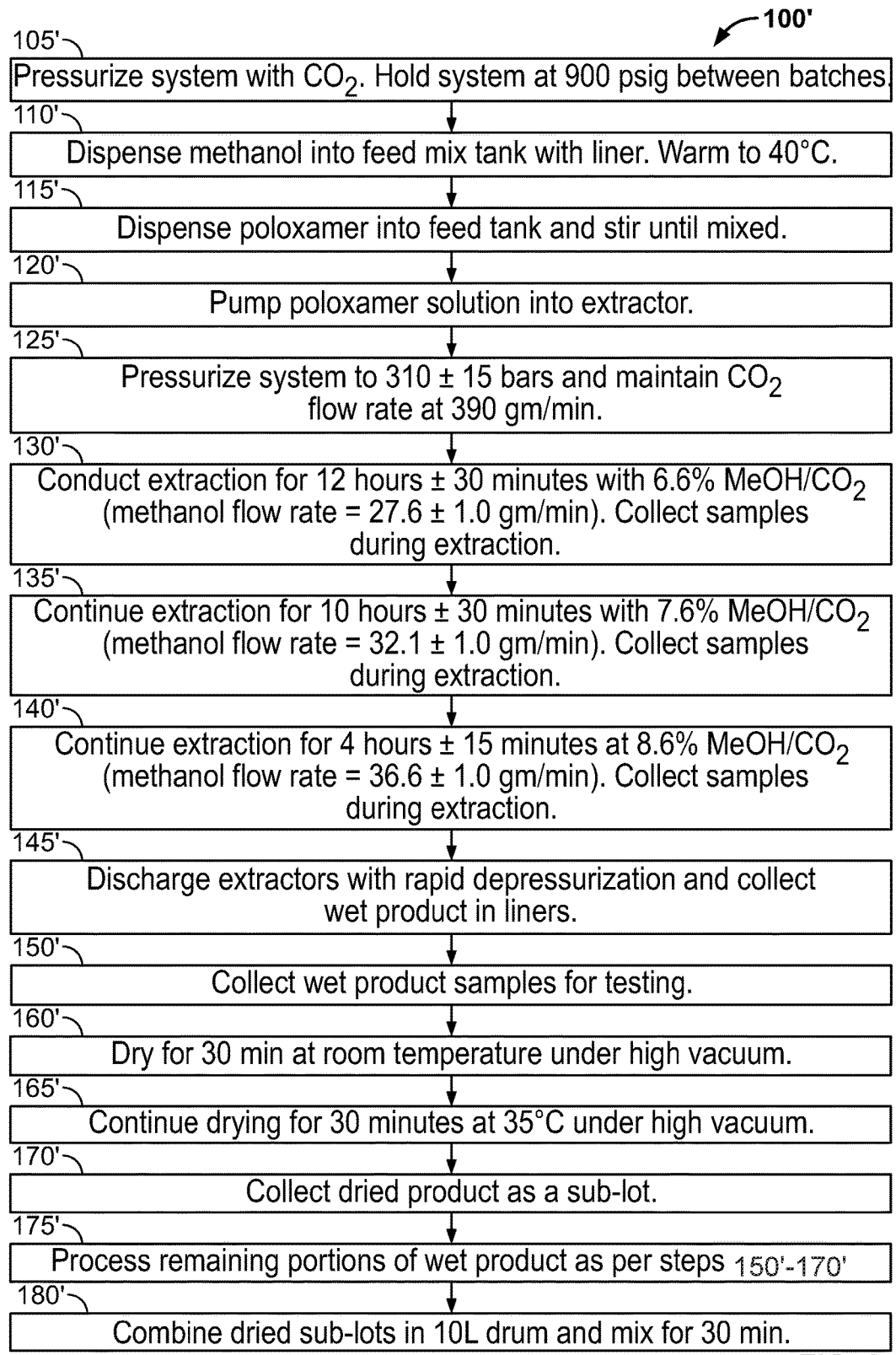
FIG. 2 is a specific exemplary process 100' for preparing a poloxamer, such as poloxamer 188, using the methods described herein.

FIG. 2 depicts certain embodiments of the methods herein that provide a process 100' that is useful for removing LMW substances in a poloxamer. The extraction system is pressurized, as shown in step 105', prior to dispensing a first alkanol (e.g., methanol) into the feed mix tank, as shown in step 110'. The system is heated to a temperature suitable for the extraction process, which is a temperature above the critical temperature of carbon dioxide used in the process that is about 31° C. Typically, the temperature is no more than 40° C. The temperature is generally kept constant through the process.

The first alkanol (e.g., methanol) is used to form a poloxamer solution according to step 115' in process 100'. In this process, dispensing of a P188 poloxamer into the feed tank with the alkanol (e.g., methanol) results in a P188 poloxamer solution that is dissolved in the alkanol (e.g., methanol). The amount of poloxamer for use in the method can be any amount, such as any amount described herein above. After forming a poloxamer/alkanol mixture, all or part of the mixture is pumped into the extractor as shown in step 120'. In some cases, the poloxamer solution can be formed in the extraction vessel by introducing the poloxamer as a solid into the extractor prior to mixing with the alkanol.

The extractor is then pressurized and the extraction solvent is introduced into the extractor as shown in step 125' of process 100'. The extraction solvent typically contains carbon dioxide and extraction is performed at a temperature greater than the critical temperature of 31° C. as described above and under high pressure greater than the critical pressure of 74 bars. For example, in an exemplary method, the extraction vessel is pressurized to about 310±15 bars, and the carbon dioxide is provided at a flow rate that is 20 kg/h to 50 kg/h, such as generally about or approximately 24 kg/h (i.e., 390 g/min).

The extraction then is conducted in the presence of a second alkanol acting as a co-solvent modifier of the carbon dioxide. The second alkanol, such as methanol, is added in a gradient step-wise fashion such that the concentration of the second alkanol in the extraction solvent is increased over the time of extraction method. For example, the composition of the extraction solvent can be varied as shown in steps 130'-140'. For example, as shown in step 130', the extraction process for a poloxamer (e.g., P188) starts using about 5% to 7%, by weight (w/w) of an alkanol (e.g., methanol) in an extraction solvent with a supercritical liquid (e.g., carbon dioxide), (e.g., about 6.6%). After a defined period, the alkanol (e.g., methanol) content of the extraction solvent is raised about 1-3%, such as 1% (e.g., to 7.6%). The alkanol (e.g., methanol) content is again subsequently raised about 1-3% such as 1% (e.g., to 8.6%) during a final period. The total time of the extraction method can be 15 hours to 25 hours. Each gradient is run for a portion of the total time.

For a commercially efficient purification process, it desirable to have successively increasing methanol concentrations where the profile is suitably modified to selectively remove most of the low molecular weight components. Residual low molecular weight components can be subsequently removed with high methanol concentrations in a short time. Therefore a stepwise methanol concentration profile where about a 5-10% (e.g., 6.6%) methanol is used for 12 hours, a higher methanol is used for 10 hours and finally an even higher methanol is used for 4 hours is used to produce purified product in high yields without significantly reducing the overall yield and not enriching the high molecular weight components.

When the poloxamer material is sufficiently pure, the product is prepared for further processing as shown in process 100'. The product can be discharged from the extractor vessel and collected in an appropriate receiver, as shown in step 145'. The wet product can be sampled for testing with respect to purity, chemical stability, or other properties, as shown in step 150'. The product can be dried by removing residual solvents under vacuum as described herein. In an exemplary method, as shown in steps 160'-170', drying can be initiated with a sub-lot under vacuum at ambient temperature and drying can be then continued at higher temperatures and lower pressures as the process progresses. Remaining sub-lots can be processed in a similar manner, as shown in step 175' of process 100. Sub-lots can be combined and mixed in a suitable container, as shown in step 180', and the resulting product can be characterized, stored, transported, or formulated.

b. Preparation of Long Circulating Material Free (LCMF) Poloxamer

Figure 3:
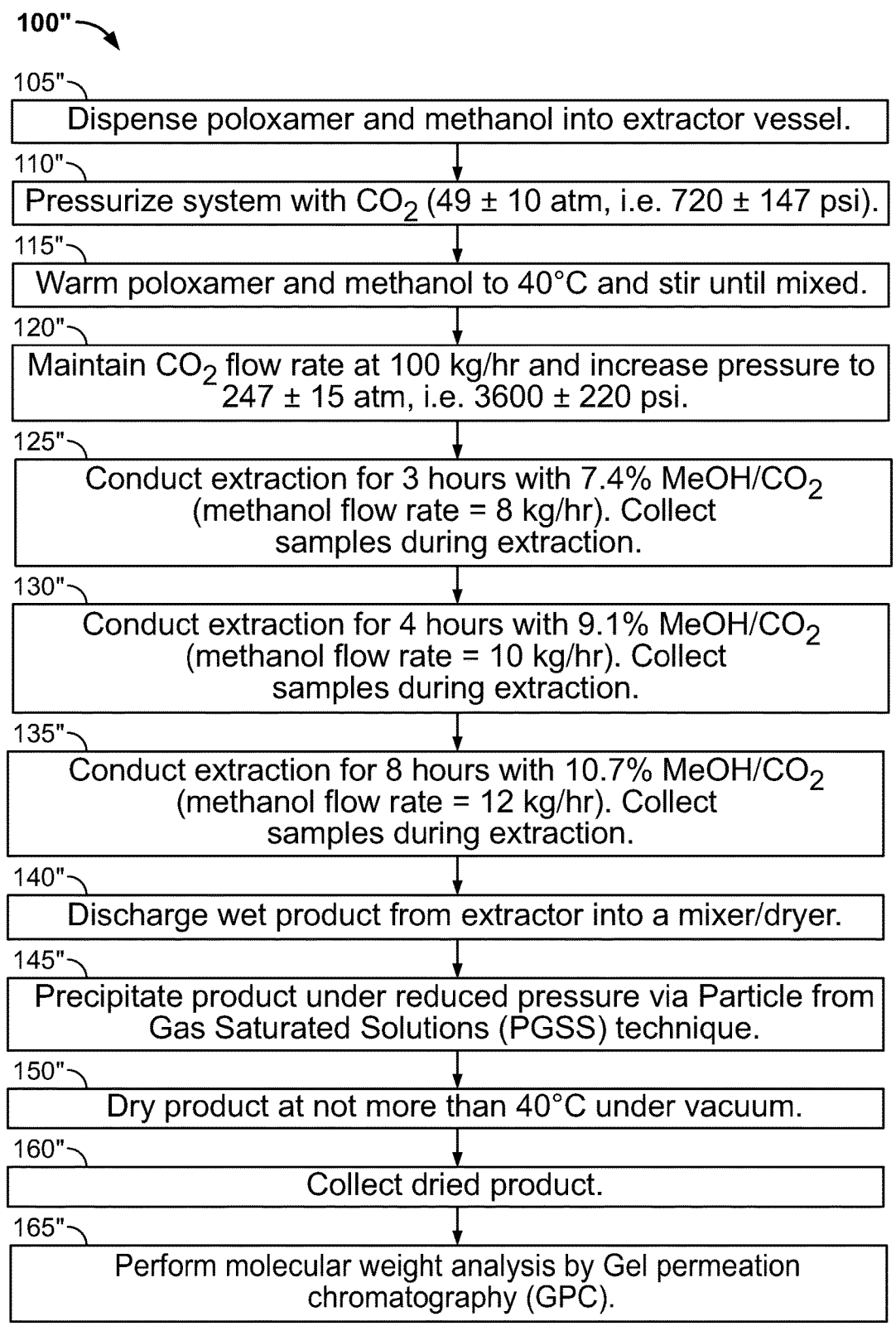
FIG. 3 is a specific exemplary process 100" for preparing a poloxamer, such as poloxamer 188, using methods described herein.

FIG. 3 depicts embodiments for preparation of LCMF poloxamer. Certain embodiments of the methods herein provide a process 100" that generates a poloxamer that does not contain any components that, after administration to a subject, results in a long circulating material in the plasma or blood as described herein. As shown in step 105", the poloxamer and first alkanol (e.g., methanol) are dispensed into the extractor vessel and to form the poloxamer solution. In this process, dispensing of a P188 poloxamer into the extraction vessel with the alkanol (e.g., methanol) results in a P188 poloxamer solution that is dissolved in the alkanol (e.g., methanol). The amount of poloxamer for use in the method can be any amount as described herein. In some cases, the poloxamer solution can be formed a separate vessel, and the poloxamer solution transferred to the extractor vessel.

The extraction system is pressurized, as shown in step 110", after dispensing a first alkanol (e.g., methanol) and poloxamer. As shown in step 115", the system is heated to a temperature suitable for the extraction process, which is a temperature above the critical temperature of carbon dioxide used in the process, that is about 31° C. Typically, the temperature is between 35° C. and 45° C. The temperature is generally kept constant through the process. The poloxamer solution is formed under pressurized carbon dioxide of about 49 bars and a temperature of between 35° C. to about or at 45° C. for a defined period, generally less than several hours.

The extractor then is pressurized and the extraction solvent is introduced into the extractor as shown in step 120" of process 100". The extraction solvent typically contains carbon dioxide and a second alkanol and extraction is perform at a temperature greater than the critical temperature of 31° C., as described above, and under high pressure, greater than the critical pressure of 74 bars. For example, in an exemplary method, the extraction vessel is pressurized to about 247±15 atm bars (range between 240 to 260 bar), and the carbon dioxide is provided at a flow rate that is 50 kg/h to 120 kg/h, inclusive, such as generally about or approximately 100 kg/h.

The extraction is conducted in the presence of the second alkanol, which acts as a co-solvent modifier of the carbon dioxide. As shown in steps 125"-135", the second alkanol, such as methanol, is added in a gradient step-wise fashion such that the concentration of the second alkanol in the extraction solvent is increased over the time of extraction method. For example, the composition of the extraction solvent can be varied as shown in steps 125"-135". For example, as shown in step 125", the extraction process for a poloxamer (e.g., P188) starts using about 7% to 8% (e.g., about or 7.4%), by weight (w/w) of an alkanol (e.g., methanol) in an extraction solvent with a supercritical liquid (e.g., carbon dioxide). After a defined period, the alkanol (e.g., methanol) content of the extraction solvent is raised about 1-3%, such as up to 2% (e.g., to 9.1%). The alkanol (e.g., methanol) content is again subsequently raised about 1-3% such as up to 2% (e.g., to 10.7%) during a final period. The total time of the extraction method can be 15 hours to 25 hours, inclusive. Each gradient is run for a portion of the total time.

For an extraction process that removes components other than low molecular weight components, including components that, when administered, give rise to longer circulating forms, it desirable to have a process that maximizes the purity and removal of these components while minimizing reductions in yield. It is found that successively increasing alkanol (e.g., methanol) concentrations when starting from a higher concentration of alkanol (e.g., methanol) than in other methods, generally starting at 7% to 8% by weight, the profile is suitably modified to selectively remove these components and low molecular weight components, while minimizing reductions in yield. For example, such an exemplary method can produce yields greater than 55%, and generally greater than 60% or 65%. Residual low molecular weight components can be subsequently removed with high methanol concentrations in a short time. Therefore a stepwise methanol concentration profile where about a 7-8% (e.g., 7.4%) methanol is used for about 3 hours, a higher methanol (e.g., 9.1%) is used for about 4 hours and finally an even higher methanol (e.g., 10.7%) is used for about 8 hours produces a purified product in high yields without significantly reducing the overall yield.

When the poloxamer material is sufficiently pure, the product is prepared for further processing as shown in process 100". The product can be discharged from the extractor vessel and collected in an appropriate receiver, as shown in step 140". The product can be precipitated under reduced pressure via particles from gas saturated solutions (PGSS) techniques as shown in step 145". The product can be dried by removing residual solvents under vacuum as described herein. In an exemplary method, as shown in steps 150"-165", drying can be initiated under vacuum at high temperatures of between 35° C. to 45° C. The dried product can be collected as shown in step 160". The resulting product can be characterized, stored, transported, or formulated as shown in step 165".

5. Methods for Confirming the Identity of LCMF Poloxamers

To confirm that a poloxamer 188 preparation made by the methods herein or other methods is an LCMF poloxamer 188, the properties of the poloxamer can be assessed. The properties include, but are not limited to, the absence of a longer circulating material upon administration to a human or an animal model, the behavior of the poloxamer in reverse phase (RP)-HPLC compared to a preparation of poloxamer that contains the LCM material such as the poloxamer described in U.S. Pat. No. 5,696,298 and commercially available poloxamer 188 (e.g., those sold under the trademarks Pluronic® F-68, Flocor®, Kolliphor® and Lutrol®), and the behavior in RP-HPLC under the conditions exemplified herein (see i.e., Example 7). Any method that confirms that the preparation lacks LCM material can be used.

E. PHARMACEUTICAL COMPOSITIONS AND FORMULATIONS

Compositions containing a poloxamer P188, such as any prepared by methods provided herein, are provided. In particular, provided herein are compositions containing an LCMF poloxamer, particularly an LCMF poloxamer P188. The compositions are used for and used in methods for treating any disease or condition in which P188 is known or is able to treat, such as any described in Section F.

1. Formulations

Pharmaceutical compositions containing P188, such as LCMF P188, can be formulated in any conventional manner by mixing a selected amount of the poloxamer with one or more physiologically acceptable carriers or excipients to produce a formulation. Selection of the formulation, carrier and/or excipient is within the skill of the administering professional and can depend upon a number of parameters. These include, for example, the mode of administration (i.e., systemic, oral, nasal, pulmonary, local, topical, or any other mode) and the symptom, disorder, or disease to be treated.

Effective concentrations of P188, such as an LCMF P188, are mixed with a suitable pharmaceutical carrier or vehicle for systemic, topical or local administration. Pharmaceutical carriers or vehicles suitable for administration of the copolymers include any such carriers known to those skilled in the art to be suitable for the particular mode of administration. Pharmaceutical compositions that include a therapeutically effective amount of a P188, such as an LCMF P188, also can be provided as a lyophilized powder that is reconstituted, such as with sterile water, immediately prior to administration.

The compound can be suspended in micronized or other suitable form or can be derivatized to produce a more soluble active product. The form of the resulting mixture depends upon a number of factors, including the intended mode of administration and the solubility of P188, such as LCMF P188, in the selected carrier or vehicle. The resulting mixtures are solutions, suspensions, emulsions and other such mixtures, and can be formulated as an non-aqueous or aqueous mixtures, creams, gels, ointments, emulsions, solutions, elixirs, lotions, suspensions, tinctures, pastes, foams, aerosols, irrigations, sprays, suppositories, bandages, or any other formulation suitable for systemic, topical or local administration. For local internal administration, such as, intramuscular, parenteral or intra-articular administration, the poloxamers can be formulated as a solution suspension in an aqueous-based medium, such as isotonically buffered saline or can be combined with a biocompatible support or bioadhesive intended for internal administration.

Generally, pharmaceutically acceptable compositions are prepared in view of approvals for a regulatory agency or are prepared in accordance with generally recognized pharmacopeia for use in animals and in humans. Pharmaceutical compositions can include carriers such as a diluent, adjuvant, excipient, or vehicle with which an isoform is administered. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A composition, if desired, also can contain minor amounts of wetting or emulsifying agents, or pH buffering agents, for example, acetate, sodium citrate, cyclodextrin derivatives, sorbitan monolaurate, triethanolamine sodium acetate, triethanolamine oleate, and other such agents. These compositions can take the form of solutions, suspensions, emulsions, tablets, pills, capsules, powders, and sustained release formulations. Capsules and cartridges of (e.g., gelatin) for use in an inhaler or insufflator can be formulated containing a powder mix of a therapeutic compound and a suitable powder base such as lactose or starch. Such compositions will contain a therapeutically effective amount of P188, in a form described herein, including the LCMF form, together with a suitable amount of carrier so as to provide the form for proper administration to a subject or patient.

The formulation is selected to suit the mode of administration. For example, compositions containing P188, such as LCMF P188, can be formulated for parenteral administration by injection (e.g., by bolus injection or continuous infusion). The injectable compositions can take such forms as suspensions, solutions or emulsions in oily or aqueous vehicles. Buffers, preservatives, antioxidants, and the suitable ingredients, can be incorporated as required, or, alternatively, can comprise the formulation.

Formulations suitable for parenteral administration include, but are not limited to, aqueous and non-aqueous sterile injection solutions, which can contain anti-oxidants, buffers, bacteriostats and solutes that render the formulation compatible with the intended route of administration. The formulations can be presented in unit-dose or multi-dose containers, for example, sealed ampules and vials, prefilled syringes or other delivery devices and can be stored in an aqueous solution, dried or freeze-dried (lyophilized) conditions, requiring only the addition of the sterile liquid carrier, for example, water for injection, immediately prior to use.

P188, such as LCMF P188, can be formulated as the sole pharmaceutically active ingredient in the composition or can be combined with other active ingredients. Liposomal suspensions, including tissue-targeted liposomes, also can be suitable as pharmaceutically acceptable carriers. These can be prepared according to methods known to those skilled in the art. For example, liposome formulations can be prepared as described in U.S. Pat. No. 4,522,811. Liposomal delivery also can include slow release formulations, including pharmaceutical matrices such as collagen gels and liposomes modified with fibronectin (see, for example, Weiner et al. (1985) J Pharm Sci. 74(9): 922-925). The compositions provided herein further can contain one or more adjuvants that facilitate delivery, such as, but not limited to, inert carriers, or colloidal dispersion systems. Representative and non-limiting examples of such inert carriers can be selected from water, isopropyl alcohol, gaseous fluorocarbons, ethyl alcohol, polyvinyl pyrrolidone, propylene glycol, a gel-producing material, stearyl alcohol, stearic acid, spermaceti, sorbitan monooleate, methylcellulose, as well as suitable combinations of two or more thereof.

The P188, such as LCMF P188, is included in the pharmaceutically acceptable carrier in an amount sufficient to exert a therapeutically useful effect in the absence of undesirable side effects on the subject treated. The therapeutically effective concentration can be determined empirically by testing the compounds in known in vitro and in vivo systems, such as the assays provided herein.

2. Dosage

The pharmaceutical compositions containing P188, such as LCMF P188 provided herein, can be formulated for single dosage (direct) administration, multiple dosage administration or for dilution or other modification. The concentrations of the compounds in the formulations are effective for delivery of an amount, upon administration, that is effective for the intended treatment. Those of skill in the art readily can formulate a composition for administration in accord with the methods herein. For example, to formulate a composition, the weight fraction of a compound or mixture thereof is dissolved, suspended, dispersed, or otherwise mixed in a selected vehicle at an effective concentration such that the intended effect is observed.

The precise amount or dose of the therapeutic agent administered depends on the condition being treated, the route of administration, and other considerations, such as the weight and physiological state of the subject and the subject.

If necessary, a particular dosage and duration and treatment protocol can be empirically determined or extrapolated. For example, exemplary doses of P188, such as LCMF P188 provided herein, if necessary, can be used as a starting point to determine appropriate dosages for a particular subject and condition. The duration of treatment and the interval between injections will vary with the severity of the disease or condition and the response of the subject to the treatment, and can be adjusted accordingly. Factors such as the level of activity and half-life of the P188, such as LCMF P188, can be taken into account when making dosage determinations. Particular dosages and regimens can be empirically determined by one of skill in the art.

In particular, the poloxamer can be formulated at a concentration ranging from about 10.0 mg/mL to about 300.0 mg/mL, such as at or at least 10.0, 15.0, 20.0, 25.0, 30.0, 35.0, 40.0, 45.0, 50.0, 55.0, 60.0, 65.0, 70.0, 75.0, 80.0, 85.0, 90.0, 95.0, 100.0, 105.0, 110.0, 115.0, 120.0, 125.0, 130.0, 135.0, 140.0, 145.0, 150.0, 155.0, 160.0, 165.0, 170.0, 175.0, 180.0, 185.0, 190.0, 195.0, 200.0, 205.0, 210.0, 215.0, 220.0 225.0, 230.0, 235.0, 240.0, 245.0, 250.0, 255.0, 260.0, 265.0, 270.0, 275.0, 280.0, 285.0, 290.0, 295.0 or 300.0 mg/mL, for administration. Typically, the concentration is not more than 22.5%, i.e. 225 mg/mL.

For example, when administered separately or as a component of the pharmaceutical composition described herein, the poloxamer generally is administered at a concentration of between about 0.5% to 25.0%, such as 0.5% to 20% or 25%, although more dilute or higher concentrations can be used. For example, the poloxamer can be administered at a concentration of between about 0.5% to about 25%, by weight/volume, such as at least 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10.0%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21.0%, 21.5%, 22.0%, 22.5%, 23.0%, 23.5%, 24.0%, 24.5% or 25.0% by weight/volume. In other embodiments, the poloxamer is administered at a concentration between about 0.5% to about 10% by weight/volume, such as 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10.0% by weight/volume. In yet other embodiments, the poloxamer is administered at a concentration between about 5% to about 15% by weight/volume, such as 5%, 5.5%, 6%, 6.5%, 7%, 7.5%, 8%, 8.5%, 9%, 9.5%, 10.0%, 10.5%, 11%, 11.5%, 12%, 12.5%, 13%, 13.5%, 14%, 14.5%, or 15% by weight/volume. In other embodiments, the poloxamer is administered at a concentration of between 16%-25% such as 22.5% weight/volume. For example, the concentration is 10% to 22.5%, such as 10% to 20% or 15% to 20%.

In one example, the poloxamer can be formulated as a sterile, non-pyrogenic solution intended for administration with or without dilution. The final dosage form can be a prepared in a 100 mL vial where the 100 mL contains 15 g (150 mg/mL) of purified poloxamer 188, such as LCMF P188, 308 mg sodium chloride USP, 238 mg sodium citrate USP, 36.6 mg citric acid USP and water for injection USP Qs to 100 mL. The pH of the solution is approximately 6.0 and has an osmolarity of about 312 mOsm/L. For other applications, at least 500 mls is prepared with a concentration of 10% to 20%, such as about or at 15% weight of poloxamer preparation/volume of the composition. For example, for intravenous administration, the composition is formulated to achieve the target Css when the composition is infused using a loading dose of 100 mg/kg for 1 hour followed by a maintenance infusion of 30 mg/kg/hr for 48 hours. The skilled physician or pharmacist or other skilled person, can select appropriate concentrations for the particular subject, condition treated and target circulating concentration.

3. Dosages and Administration

In the methods herein, poloxamer 188, such as an LCMF P188 described herein, can be administered to a subject for treating a disease or condition, including any disease or condition as described in Section F. In particular, poloxamer 188, such as a purified poloxamer 188 described herein, is intended for use in therapeutic methods in which other P188 compositions can be or have been used for treatment.

Treatment of diseases and conditions, such as any described in Section F, with poloxamer 188, such as a purified poloxamer 188 described herein, can be effected by any suitable route of administration using suitable formulations as described herein including, but not limited to parenteral administration, including intravenous and intra-arterial (via catheter directed administration or other route), intrapulmonary, oral or transdermal administration. Treatment typically is effected by intravenous administration.

Active agents, for example a poloxamer 188, such as an LCMF P188, are included in an amount sufficient that they exert a therapeutically useful effect in the absence of undesirable side effects on the patient treated. The amount of a P188, such as an LCMF P188, to be administered for any disease or condition, can be determined by standard clinical techniques. In addition, in vitro assays and animal models can be employed to help identify optimal dosage ranges. The precise dosage, which can be determined empirically, can depend on the particular composition, the route of administration, the desired duration of administration, the type of disease to be treated and the seriousness of the disease.

Practical limitations have restricted the clinical use of poloxamer 188 that was manufactured according to National Formulary specifications (P188-NF) (Emanuele and Balasubramanian, Drugs R D 14(2):73-83 (2014)), due to renal dysfunction in a subset of patients enrolled in early clinical trials. In addition, animal studies reveal that P188-NF increases the levels of serum creatinine and creatinine is not efficiently cleared from the kidneys at the end of the drug infusion. The purified poloxamer 188 described herein has been modified to address the limitations of P188-NF. To prevent elevation of creatinine levels and renal toxicity, poloxamer 188 was purified to remove low and high molecular weight species contaminants. In clinical studies, for example the C97-1248 study, researchers found that intravenous administration of P188-P did not induce a significant increase in serum creatinine above the levels of a placebo. The reduced low and high molecular weight species, based on assessment by high performance liquid chromatography, reduces or eliminates renal risk associated with unpurified (P188-NF) treatments. Therefore, a purified poloxamer 188, such as the LCMF poloxamer 188 described herein, does not exhibit the practical limitations present in the previously assessed, unpurified form.

If necessary, a particular dosage and duration and treatment protocol can be empirically determined or extrapolated. Dosages for poloxamer 188 previously administered to human subjects and used in clinical trials can be used as guidance for determining dosages for poloxamer 188, such as a purified poloxamer 188 described herein. Dosages for poloxamer 188 can also be determined or extrapolated from relevant animal studies. Factors such as the level of activity and half-life of poloxamer 188 can be used in making such determinations. Particular dosages and regimens can be empirically determined based on a variety of factors. Such factors include body weight of the individual, general health, age, the activity of the specific compound employed, sex, diet, time of administration, rate of excretion, drug combination, the severity and course of the disease, the patient's disposition to the disease, and the judgment of the treating physician. The active ingredient, poloxamer 188, typically is combined with a pharmaceutically effective carrier. The amount of active ingredient that can be combined with the carrier materials to produce a single dosage form or multi-dosage form can vary depending upon the host treated and the particular mode of administration.

In particular examples, the poloxamer, such as P188 (e.g., LCMF P188), is formulated for administration to a patient at a dosage of about 100 mg/kg or 100 mg/kg and up to 2000 mg/kg depending upon the condition to be treated. Doses include, for example, 100 to 500 mg/kg patient body weight, for example 100 mg/kg to 450 mg/kg, 100 to 400 mg/kg, 100 mg/kg to 300 mg/kg, 100 mg/kg to 200 mg/kg, 200 mg/kg to 500 mg/kg, 200 mg/kg to 450 mg/kg, 200 mg/kg to 400 mg/kg, 200 mg/kg to 300 mg/kg, 300 mg/kg to 500 mg/kg, 300 mg/kg to 450 mg/kg 300 mg/kg to 400 mg/kg, 400 mg/kg to 500 mg/kg, 400 mg/kg to 450 mg/kg or 450 mg/kg to 500 mg/kg patient body weight, such as at least or at least about 100, 125, 150, 200, 250, 300, 350, 400, 450, 500, 600, 700, 800, 900, 1000, 1100, 1200, 1300, 1400, 1500, 1600, 1700, 1800, 1900 and 2000 mg/kg patient body weight.

The dose of poloxamer is administered at a concentration and in a fluid volume that suits the mode of administration and the physiological needs of the patient. Generally, for longer term infusions (such as a 12, 24, or 48 hour continuous infusion) the volume administered is typically not greater than about 5.0 mL/kg/hr, such as 4.5 ml/kg/hr, 4.0 ml/kg/hr, 3.5 ml/kg/hr, 3.0 ml/kg/hr, 2.5 ml/kg/hr, 2.0 ml/kg/hr, 1.5 ml/kg/hr, 1.0 ml/kg/hr, 0.5 ml/kg/hr, 0.25 ml/kg/hr or 0.125 ml/kg/hr. For shorter term administrations (such as bolus administrations or short term infusions) the dose of poloxamer may be administered in a volume greater than 5.0 ml/kg/hr such as 7.5 ml/kg/hr or 10.0 ml/kg/hr or 12.5 ml/kg/hr or 15 ml/kg/hr or even higher depending upon the needs of the patient. The poloxamer can be administered as a single dose or in multiple doses that are repeated over various intervals, such as hourly, daily, weekly, monthly or more. For infusions, the infusions can provide the appropriate dosage to the subject over a time period that is typically 1 hour to 72 hours, such as 12 hours, 24 hours or 48 hours.

The formulations used in the methods provided herein can be administered by any appropriate route, for example, orally, nasally, pulmonary, parenterally, intravenously, intradermally, subcutaneously, intraarticularly, intracisternally, intraocularly, intraventricularly, intrathecally, intramuscularly, intraperitoneally, intratracheally or topically, as well as by any combination of any two or more thereof, in liquid, semi-liquid or solid form and are formulated in a manner suitable for each route of administration. Multiple administrations, such as repeat administrations described herein, can be effected via any route or combination of routes. The most suitable route for administration will vary depending upon the disease state to be treated. Typically, the compositions are formulated for intravenous infusions.

The effective amounts of a poloxamer, such as P188 and in particular an LCMF P188 as provided herein, can be delivered alone or in combination with other agents for treating a disease or condition. It is within the level of a skilled artisan to choose a further additional treatment to administer in conjunction with a therapeutic regimen employing LCMF P188. Such a decision will depend on the particular disease or condition being treated, the particular subject being treated, the age of the subject, the severity of the disease or condition and other factors.

F. METHODS AND THERAPEUTIC USES OF POLOXAMER 188 AND LCMF P188

Poloxamer 188 (P188) and compositions thereof, such as LCMF P188 and compositions thereof, can be used in a wide variety of applications, including cytoprotective, hemorheologic, anti-inflammatory, antithrombotic/pro-fibrinolytic applications, with clinical utility in diverse diseases including, but not limited to, acute myocardial infarction, acute limb ischemia, shock, acute stroke, heart failure, sickle cell disease, and neurodegenerative diseases. The P188 provided herein, such as the LCMF P188 or any P188 produced by a method provided herein can be used to treat any disease or condition or application in which P188 has previously been used or is known to be effective. Several uses for P188 have been reviewed in, for example, in Moloughney et al., (2012) Recent Pat Biotechnol. 6(3):200-211 and Karmarker, "Poloxamers and their applications" Pharmainfo.net Published Oct. 27, 2008, where the URL is: pharmainfo.net/pharma-student-magazine/poloxamers-and-their-applications-0. Exemplary uses for P188 include, but are not limited to, use in applications requiring membrane resealing and repair, treatment of tissue ischemia and reperfusion injury, decreasing inflammatory responses, reduction of blood viscosity, facilitating thrombolysis, promoting hemostasis, use as a vehicle for drug, nucleic acid or protein delivery, use as an emulsifier, use liquid suspension stabilizer for hydrophobic drugs, cleansing for skin wounds, use as a surfactant in the formulation of cosmetics, use to control the viscosity of personal care products and soaps, and pharmaceutical use as a laxative (see, e.g., European publication number EP 0682946).

P188, such as LCMF P188, can be used in applications requiring membrane resealing, stability, and/or repair. Such uses prevent cell loss in tissue, such as damaged tissue, by protecting cells from apoptotic and necrotic death. For example, P188 can be used to repair cell membranes following electrical injury or free radical injury (see, e.g., U.S. Pat. No. 5,605,687, U.S. Patent Publication No. 2006/0121016, and Lee et al., (1992) Proc. Natl. Acad. Sci. USA 89:4524-4528). P188 also can be used to reduce cell death following cartilage damage, such as following traumatic joint injury (see, e.g., Isaac et al., (2010) J Orthop Res. (4):553-558), for example, to help prevent osteoarthritis. P188 also has been used for neuroprotection in response to excitotoxicity, such as glutamate toxicity (Frim et al., (2004) Neuro Report. 15: 171-174). P188 also has been used as a reagent for the treatment of degenerative diseases, such as Alzheimer's disease, by repairing membranes damaged by misfolded proteins (see, e.g., U.S. Patent Publication No. 20100316590).

P188 also has been used to treat and prevent cardiomyopathy and heart disease associated with reduced expression of dystrophin (see, e.g., U.S. Pat. Nos. 7,846,426 and 8,580,245), and to treat chronic heart failure caused by mechanisms other than the loss of dystrophin (see, e.g., U.S. Patent Publication No. 2009/0246162). Compositions containing P188 also can be used to inhibit thrombosis, reduce myocardial infarct size, decrease blood viscosity and improve perfusion of damaged tissue following myocardial infarction (Justicz et al., (1991) Am Heart J. 122(3 Pt 1):671-680; O'Keefe et al., (1996) Am. J. Cardiol. 78:747-750).

P188 also can be used in methods of cell transplantation to minimize damage to the cell membrane of transplanted cells during the procedure. For example, compositions containing P188 can be used to improve the survival of adipocytes during grafting of fat tissues, fat cells, stem cells and other cells derived from fat tissue (see, e.g., U.S. Pat. No. 8,512,695 and U.S. Patent Publication No. 2010/0104542), such as in applications of soft tissue reconstruction or augmentation. P188 has also been used to improve survival and reinnervation of transplanted dopaminergic cells for Parkinson's disease therapy (Quinn et al., (2008) Eur J Neurosci. 27(1):43-52).

P188 also can be used as a therapeutic agent to treat chronic microvascular diseases, such as, but not limited to, macular degeneration, diabetic retinopathy and congestive heart failure (see, e.g., U.S Patent Publication No. US2011/0212047). Uses of P188 for the treatment of tissue ischemia and reperfusion injury, such as in models of superior mesenteric artery occlusion (SMAO), also have been described (see, e.g., Hunter et al., (2010) Ann Clin Lab Sci. 40(2):115-125). Compositions containing P188 also has been used to treat skeletal muscle disorders, such as Duchenne muscular dystrophy (DMD) and related disorders (see, e.g., U.S Patent Publication No. 2011/0033412).

P188 also has been used to enhance blood flow, for example, by reducing blood viscosity, for example, by preventing adhesive interactions in the blood to (see, e.g., U.S. Publication, No. 2010/0183519). Such uses can reduce problems associated with reduced of blood flow, such as production of fat emboli (see, e.g., Adams et al., (1960) Surg. Forum 10:585 and Danielson et al., (1970) J Thorac Cardiovasc Surg. 59(2):178-184), and erythrocyte sedimentation (Hoppensteadt et al., (2014) FASEB J. 28(1):suppl. 1139.6). P188 also has been used to treat hemorrhagic shock (Mayer et al., (1994) Ann Clin Lab Sci. 24(4):302-311).

P188 also has been used to treat sickle cell disease (SD), which refers to homozygous sickle cell anemia (SS) as well as mixed heterozygous states, such as SC, SD, and S-β thalassemia (see, e.g., Adams-Graves et al., (1997) Blood 90:2041-2046; Ballas et al., Hemoglobin 2004, 28(2):85-102; Gibbs and Hagemann, (2004) Ann. Pharmacother. 38:320-324; Orringer JAMA. 2001; 286(17):2099-2106).

The inflammatory response also can be decreased by the use of P188, for example by inhibiting phagocyte migration and, for example, reducing the influx and adherence of neutrophils (see, e.g., Lane et al., (1984) Blood. 64:400-405; Schaer et al., (1994) Circulation. 90(6):2964-2975).

P188 also can be used in therapies for wound healing and sealing (see, e.g., U.S. Provisional Patent Application No. 62/021,676, U.S. Pat. No. 8,758,738, and U.S. Patent Publication No. 20140056839).

Additional uses of P188 include its use as a tissue culture media additive, including as a supplement for cryostorage media (see, e.g., Kerleta et al., (2010) ALTEX. 27(3):191-197), and an additive to blood and blood products, such packed red blood cells, to prevent or reduce storage lesion compromised blood.

P188 also has been used in the formulation of various cosmetics and pharmaceuticals. P188 can be used to increase the solubility and bioavailability of pharmaceutical compositions (see, e.g., U.S. Patent Publication Nos. 20040258718, 20090214685, 20100087501, 20100249240, 20110008266, 20120277199, and U.S. Pat. Nos. 8,133,918, 8,460,644 and 8,709,385), nucleic acids (see, e.g., U.S. Patent Publication Nos. 20030206910 and 20060013883), anti-microbial agents (see, e.g., U.S. Patent Publication No. 20060078616), and proteins (see, e.g., U.S. Patent Publication Nos. 20100310669 and 2012/0141619, U.S. Pat. No. 8,137,677, and Jeong B., et al., (2002) Adv Drug Del Rev, 54(1); 37-51). P188 can be used as a pharmaceutical carrier for the delivery of pharmaceutical agents, for example, for ophthalmic delivery (Qi et al. (2007) Int. J. Pharm. 337: 178-187), mucoadhesive delivery (Chang et al., (2002) J. Controlled Rel. 82:39-50), rectal delivery (Choi et al. (1998) Int. J. Pharm. 165:23-32; Yong et al, (2006) Int. J. Pharm. 321:56-61; ElHady et al., (2003) Saudi Pharmaceutical Journal. 11:159-171; Yong et al., (2004) Eur. J. Pharm. Sci. 23:347-353; Yun et al, (1999) Int. J. Pharm. 189:137-145; and Paek et al., (2006) Biological & Pharmaceutical Bulletin. 29:1060-1063), and transdermal delivery (Cappel et al., (1991) Int. J. Pharm. 69:155-167). P188 also can be used as an emulsifier, suspension stabilizer in liquid orals, parenteral and topical dosage forms and also as solubilizer for hydrophobic drugs. In solid dosage forms, P188 can be used as a wetting agent, plasticizer, or tablet lubricant and has wide application in formulation of gels due to its thermo-reversible gelation behavior (see, e.g., Desai et al, (2007) Drug Deliv. 14(7):413-426 and Muzíková et al., (2013) Acta Pol Pharm. 70(6):1087-1096).

G. EXAMPLES

The following examples are included for illustrative purposes only and are not intended to limit the scope of the inventions herein.

Example 1

Continuous Process Purification of Poloxamer 188 by Extraction with Methanol/Supercritical $CO_2$ Co-Solvent A continuous process purification of poloxamer 188 by extraction with a methanol/supercritical $CO_2$ co-solvent was evaluated. The continuous process allows for high throughput. A feed solution of poloxamer 188 (Asahi Denka Kogyo, Japan) in methanol was pumped at the midpoint of a high pressure extraction column packed with suitable packing material. Supercritical $CO_2$ (Carboxyque, France) mixed with methanol was pumped through the extraction column from the bottom in a counter current fashion (flow rate=30 kg/h to 40 kg/h). The average concentration of methanol was 13%, and was provided as a gradient of 9 to 13.2 weight %. The gradient was controlled by controlling the methanol, $CO_2$ and poloxamer flow rates at the feed port in the middle of the column and the $CO_2$/methanol flow rate introduced at the bottom of the column. The column pressure was 200±15 bars. The temperature of the feed solution and supercritical $CO_2$/methanol solvent was a gradient of 36 to 44° C. The column jacket temperature and extraction temperature were a gradient of 36 to 54° C.

Low molecular weight (LMW) polymers were removed at the top of the column while purified product containing methanol was removed from the bottom of the extraction column. The purified product was collected hourly and precipitated under reduced pressure via a Particle from Gas Saturated Solutions (PGSS) technique. The purified product was dried under vacuum at not more than 40° C. to remove residual methanol.

The approximate yield of purified poloxamer per feed was approximately 60%. The peak average molecular weight was approximately 9,000 Daltons. Low molecular weight components (less than 4,500 Daltons) were approximately 1.0%. Polydispersity was approximately 1.0.

Example 2

Assessing Equilibrium Concentrations of Methanol and Effect on Product Discharge In order to minimize handling of the purified poloxamer 188 in an open environment after purification, concentrations of methanol in the purified poloxamer 188 product suitable for a smooth extrusion of the product from the extractor without opening the lid were determined. Two batches of poloxamer 188 (approximately 8,000 and 9,000 Da) were assessed to identify equilibrium concentrations of poloxamer 188/methanol/$CO_2$ in the extraction vessel. An extraction vessel was charged with 0.25 grams of poloxamer 188 per mL of extraction cell capacity, at 3,000 psig (208 bars) and 4,500 psig (311 bars). The equilibrium concentration of methanol in the charged polymer 188 product inside the extraction vessel was measured in dedicated experiments and during 26-hour runs. The results showed that the equilibrium concentration of methanol in the charged poloxamer 188 product in the extraction vessel at 6.6% to 8.6% methanol/$CO_2$ is approximately 25 to 35% methanol.

To assess which concentrations in the purified product were suitable for discharge of the product from the extractor without opening the lid, the concentration of raffinate left in a 12 L extraction vessel was adjusted to various levels between 25 and 35%. The product was discharged through a rapid depressurization system. Correlation of drying characteristics with the discharge conditions was evaluated. The results showed that at higher methanol concentrations, at the higher end of 25% to 35% concentration range, approximately 2600 grams of wet product were discharged in less than 10 minutes to provide a fine, free-flowing powder. Product appearance did not change with a change in head pressure from 4500 to 1000 psi (311 to 70 bars). Slower discharge rates and lower methanol concentrations produced coarse particles.

Example 3

Effect of Solvent Distribution Systems on Supercritical Fluid Extraction (SFE)

The effect of the solvent distribution system on supercritical fluid extraction (SFE) using a methanol/supercritical $CO_2$ co-solvent was determined. The distribution systems can include metallic or ceramic spheres of various sizes packed at the bottom. Porosity of this bed can be precisely controlled by selecting different size spheres or using a mixture of different size spheres. The porosity of the system controls the bubble size and extraction efficiency. These spheres can be easily removed and cleaned. Various distribution systems were compared for their effects on the SFE process, and for their efficiency in extracting low molecular weight (LMW) material in comparison to total material extracted. Efficiency is typically determined by yield and throughput for specified target low molecular weight species (% of LMW components <4,500 Daltons).

A. Method

An SFE process was conducted with a 3.08 L cell under the following conditions: T=40° C., pressure=300 bars, methanol flow rate=6.6% of total flow rate (6.5-7 g/min methanol flow rate for 95-100 g/min $CO_2$ flow rate; 10-10.5 g/min methanol flow rate for 140-148 g/min $CO_2$ flow rate), cell length=5', and ID=2". A series of experiments were performed by performing the process using different solvent distribution systems as follows: no system; stainless steel (SS) spheres at the bottom of the cell; an aluminum suction strainer with SS-spheres; a suction screen (40 mesh) with SS-spheres; a bent tube with 6 holes ($1/16$" diameter); or a bent tube with 12 holes ($1/16$" diameter).

Extract samples collected for the first, second, third and fourth hours of extraction were analyzed by GPC and gravimetric analysis. The weight average molecular weight (Mw), molecular weight of the highest peak (Mp) and polydispersity index (PD) (defined as Mw/number average molecular weight) were calculated.

B. Results

For each distribution system tested, the run conditions and parameters for each experiment are summarized, as are the GPC Results and gravimetric analysis 1. Distribution System—None

TABLE 1

| Exp. #1 Run Conditions | |
|---|---|
| Cell | Length = 5', ID = 2" |
| Cell Temperature | 40° C. |
| Extraction Pressure | 300 bars |
| $CO_2$ flow rate | 95-100 g/min |
| MeOH flow rate | 6.5-7 g/min (6.6% of total flow rate) |
| Residence time | 25.86 min |
| Calculated Linear Velocity | 5.88 cm/min |
| Amount of raw materials loaded into the extractor | 599 g |

TABLE 2

Exp. #1 Gel permeation chromatography (GPC) and Gravimetric Results

| Sample Description | Amount (g) | GPC-Mp | GPC-Mw | PD | % Low Mol. Weight |
|---|---|---|---|---|---|
| Dry extract collected for the 1st hour | 18.39 | 8801 | 7768 | 1.15 | 13.96 |
| Dry extract collected for the 2nd hour | 24.45 | 8934 | 7616 | 1.24 | 17.69 |
| Dry extract collected for the 3rd hour | 24.40 | 9075 | 7785 | 1.23 | 16.62 |
| Dry extract collected for the 4th hour | 25.52 | 8999 | 7839 | 1.20 | 15.04 |

Total Dry extract collected = 92.76 g (15.26% of load)
Wet product weight after discharge: 630 g
Product yield = 481.8 g (79.2%)
Total Low Mwt extracted = 14.8 g
% Methanol in wet product = 23.52%

2. Distribution System—1000 Stainless Steel Spheres at the Bottom of the Cell

TABLE 3

Exp. #2 Run Conditions

| | |
|---|---|
| Cell | Length = 5', ID = 2" |
| Cell Temperature | 40° C. |
| Extraction Pressure | 300 bar |
| CO2 flow rate | 95-100 g/min |
| MeOH flow rate | 6.5-7 g/min (6.6% of total flow rate) |
| Residence time | 25.86 min |
| Calculated Linear Velocity | 5.88 cm/min |
| Amount of raw materials loaded into the extractor | 605 g |

TABLE 4

Exp. #2 Gel permeation chromatography (GPC) and Gravimetric Results

| Sample Description | Amount (g) | GPC-Mp | GPC-Mw | PD | % Low Mol. Weight |
|---|---|---|---|---|---|
| Dry extract collected for the 1st hour | 7.69 | 9320 | 5682 | 1.55 | 46.88 |
| Dry extract collected for the 2nd hour | 10.39 | 9459 | 6441 | 1.48 | 37.48 |
| Dry extract collected for the 3rd hour | 9.85 | 9453 | 6749 | 1.42 | 33.48 |
| Dry extract collected for the 4th hour | 11.2 | 9408 | 6900 | 1.37 | 31.08 |

Total Dry extract collected = 39.05 g (6.45% of load)
Wet product weight after discharge: 684.6 g
Product yield = 513 g (84.9%)
Total Low Mwt extracted = 14.28 g
% Methanol in wet product = 25%

The results show that the addition of 1000 SS-spheres at the bottom of the cell for better $CO_2$ and methanol distribution decreases the main product carry-over and increases the efficiency of the process by 59%. Thus, the results show that the system provides an effective $CO_2$/MeOH solvent distribution using stainless steel SS spheres at the bottom of the extractor.

3. Distribution System—1000 Stainless Steel Spheres at the Bottom of the Cells with Higher $CO_2$ Flow Rate and Linear Velocity

TABLE 5

Exp. #3 Run Conditions

| | |
|---|---|
| Cell | Length = 5', ID = 2" |
| Cell Temperature | 40° C. |
| Extraction Pressure | 300 bar |
| CO2 flow rate | 140-148 g/min |
| MeOH flow rate | 10-10.5 g/min (6.6% of total flow rate) |
| Residence time | 17.5 min |
| Calculated Linear Velocity | 8.69 cm/min |
| Amount of raw materials loaded into the extractor | 599 g |

TABLE 6

Exp. #3 Gel permeation chromatography (GPC) and Gravimetric Results

| Sample Description | Amount (g) | GPC-Mp | GPC-Mw | PD | % Low Mol. Weight |
|---|---|---|---|---|---|
| Dry extract collected for the 1st hour | 25.89 | 8969 | 7601 | 1.29 | 19.35 |
| Dry extract collected for the 2nd hour | 31.97 | 8970 | 7505 | 1.28 | 20.97 |
| Dry extract collected for the 3rd hour | 32.67 | 9085 | 7658 | 1.25 | 19.61 |
| Dry extract collected for the 4th hour | 30.35 | 9345 | 8050 | 1.22 | 16.39 |

Total Dry extract collected = 120.88 g (20.18% of load)
Wet product weight after discharge: 559.2 g
Product yield = 441.3 g (73.7%)
Total Low Mwt extracted = 23.09 g
% Methanol in wet product = 21.09%

The results show that this process was not as efficient as the process described in the previous experiment using a lower $CO_2$ flow rate and linear velocity.

4. Distribution System—Aluminum Suction Strainer with SS-Spheres

TABLE 7

Exp. #4 Run Conditions

| | |
|---|---|
| Cell | Length = 5', ID = 2" |
| Cell Temperature | 40° C. |
| Extraction Pressure | 300 bar |
| CO2 flow rate | 140-148 g/min |
| MeOH flow rate | 10-10.5 g/min (6.6% of total flow rate) |
| Residence time | 17.5 min |
| Calculated Linear Velocity | 8.69 cm/min |
| Amount of raw materials loaded into the extractor | 608 g |

TABLE 8

Exp. #4 Gel permeation chromatography (GPC) and Gravimetric Results

| Sample Description | Amount (g) | GPC-Mp | GPC-Mw | PD | % Low Mol. Weight |
|---|---|---|---|---|---|
| Dry extract collected for the 1st hour | 5.95 | 3801 | 4006 | 1.53 | 69.54 |
| Dry extract collected for the 2nd hour | 8.32 | 3873 | 4884 | 1.37 | 57.21 |

TABLE 8-continued

Exp. #4 Gel permeation chromatography (GPC) and Gravimetric Results

| Sample Description | Amount (g) | GPC-Mp | GPC-Mw | PD | % Low Mol. Weight |
|---|---|---|---|---|---|
| Dry extract collected for the 3$^{rd}$ hour | 8.8 | 3925 | 5363 | 1.31 | 50.05 |
| Dry extract collected for the 4$^{th}$ hour | 8.02 | 3947 | 5539 | 1.29 | 47.37 |

Total Dry extract collected = 31.09 g (5.11% of load)
Total Low Mwt extracted = 17.1 g The results show that the usage of aluminum suction strainer with SS-spheres in it as a distribution system instead of just 1000-SS spheres at the bottom makes the process 4 times more efficient even at higher linear velocity. For example, the method resulted in less extracted material removed, while still removing similar levels of the LMW fraction, i.e., in this example, 31.09 grams extracted material versus 120.88 grams in a previous experiment with extracted LMW fraction of 17.1 grams versus 23.09 grams, respectively. Thus, the results show that the system provided an effective $CO_2$/MeOH solvent distribution using an aluminum suction strainer at the bottom of the extractor.

5. Distribution System—Suction Screen 40 mesh with SS-Spheres

TABLE 9

Exp. #5 Run Conditions

| | |
|---|---|
| Cell | Length = 5', ID = 2" |
| Cell Temperature | 40° C. |
| Extraction Pressure | 300 bar |
| CO2 flow rate | 140-148 g/min |
| MeOH flow rate | 10-10.5 g/min (6.6% of total flow rate) |
| Residence time | 17.5 min |
| Calculated Linear Velocity | 8.69 cm/min |
| Amount of raw materials loaded into the extractor | 601 g |

TABLE 10

Exp. #5 Gel permeation chromatography (GPC) and Gravimetric Results

| Sample Description | Amount (g) | GPC-Mp | GPC-Mw | PD | % Low Mol. Weight |
|---|---|---|---|---|---|
| Dry extract collected for the 1$^{st}$ hour | 6.56 | 3747 | 4081 | 1.47 | 68.13 |
| Dry extract collected for the 2$^{nd}$ hour | 9.85 | 3723 | 4736 | 1.37 | 58.78 |
| Dry extract collected for the 3$^{rd}$ hour | 10.04 | 3741 | 5163 | 1.32 | 52.36 |
| Dry extract collected for the 4$^{th}$ hour | 7.35 | 3806 | 5280 | 1.3 | 50.36 |

Total Dry extract collected = 33.8 g (5.62% of load)
Wet product weight after discharge: 671.8 g
Product yield = 512.7 g (85.31%)
Total Low Mwt extracted = 19.22 g
% Methanol in wet product = 23.68%

The results show that the efficiency of extraction in a distribution system using suction screen 40 mesh was similar to the aluminum suction strainer with SS-spheres as described in the previous example.

6. Distribution System—Bent Tube with 6 Holes ⅟₁₆"

TABLE 11

Exp. #6 Run Conditions

| | |
|---|---|
| Cell | Length = 5', ID = 2" |
| Cell Temperature | 40° C. |
| Extraction Pressure | 300 bar |
| CO2 flow rate | 140-148 g/min |
| MeOH flow rate | 10-10.5 g/min (6.6% of total flow rate) |
| Residence time | 17.5 min |
| Calculated Linear Velocity | 8.69 cm/min |
| Amount of raw materials loaded into the extractor | 607 g |

TABLE 12

Exp. #6 Gel permeation chromatography (GPC) and Gravimetric Results

| Sample Description | Amount (g) | GPC-Mp | GPC-Mw | PD | % Low Mol. Weight |
|---|---|---|---|---|---|
| Dry extract collected for the 1$^{st}$ hour | 6.48 | 8781 | 6155 | 1.49 | 39.76 |
| Dry extract collected for the 2$^{nd}$ hour | 9.63 | 8701 | 6519 | 1.36 | 33.63 |
| Dry extract collected for the 3$^{rd}$ hour | 9.74 | 8690 | 6786 | 1.29 | 29.41 |
| Dry extract collected for the 4$^{th}$ hour | 9.7 | 8704 | 7003 | 1.26 | 25.95 |

Total Dry extract collected = 35.55 g (5.86% of load)
Wet product weight after discharge: 647 g
Product yield = 460.5 g (75.9%)
Total Low Mwt extracted = 11.2 g
% Methanol in wet product = 28.33%

The results show that the bent tube with 6 holes ⅟₁₆" diameter was less efficient than the previous distribution system.

7. Distribution System—Bent Tube with 12 Holes ⅟₁₆" Diameter

TABLE 13

Exp. #7 Run Conditions

| | |
|---|---|
| Cell | Length = 5', ID = 2" |
| Cell Temperature | 40° C. |
| Extraction Pressure | 300 bar |
| CO2 flow rate | 140-148 g/min |
| MeOH flow rate | 10-10.5 g/min (6.6% of total flow rate) |
| Residence time | 17.5 min |
| Calculated Linear Velocity | 8.69 cm/min |
| Amount of raw materials loaded into the extractor | 607 g |

TABLE 14

Exp. #7 Gel permeation chromatography (GPC) and Gravimetric Results

| Sample Description | Amount (g) | GPC-Mp | GPC-Mw | PD | % Low Mol. Weight |
|---|---|---|---|---|---|
| Dry extract collected for the 1$^{st}$ hour | 6.79 | 9162 | 5988 | 1.550 | 44.25 |
| Dry extract collected for the 2$^{nd}$ hour | 8.11 | 9208 | 6535 | 1.431 | 36.49 |

TABLE 14-continued

Exp. #7 Gel permeation chromatography (GPC) and Gravimetric Results

| Sample Description | Amount (g) | GPC-Mp | GPC-Mw | PD | % Low Mol. Weight |
|---|---|---|---|---|---|
| Dry extract collected for the 3$^{rd}$ hour | 8.28 | 9223 | 6721 | 1.364 | 34.17 |
| Dry extract collected for the 4$^{th}$ hour | 8.45 | 9341 | 7226 | 1.294 | 27.22 |

Total Dry extract collected = 31.63 g (5.41% of load)
Wet product weight after discharge: 684.1 g
Product yield = 512 g (84.3%)
Total Low Mwt extracted = 11.09 g
% Methanol in wet product = 24.91%

The results show that the bent tube with 12 holes of 1/16" diameter is slightly more efficient than the previous experiment using a distribution system with 6 holes, but less efficient than the suction screen and stainless steel spheres.

C. Summary

The highest efficiencies of purification were observed in methods in which the distribution system was an aluminum suction strainer with stainless steel spheres or a suction screen mesh with stainless steel spheres (see, e.g., experiments 4 and 5). Increasing the number of holes in a bent tube distribution system also increased the efficiency of purification to some degree (see, e.g., experiment 7). Thus, the results show that the distribution system plays a role in SFE equipment and its design makes the process more or less efficient. A suitable design is a suction screen or a suction strainer with stainless steel spheres. The bent tube can also be used as a distribution system, but with as many holes as possible. For most of the other experiments described, experiments were performed with a suction screen distribution system.

Example 4

12-L Scale Dual-Step Extraction Batch Process Purification of Poloxamer 188

A process is designed to enrich with high molecular weight components (>13,000 Daltons). In typical extraction profiles, the increase in high molecular weight components after purification is not significant. A dual-step batch process purification of poloxamer 188 is performed on a 12-L scale by controlling the methanol concentration. The poloxamer 188 prior to extraction contains approximately 1% high molecular weight components and 5% low molecular weight components as measured by Gel Permeation Chromatography (GPC).

A 12-L extraction system containing a stirred extraction vessel, cyclone separators, $CO_2$ solvent circulation and methanol co-solvent system is tested for leaks. The extraction system is pressurized with $CO_2$ to 310±15 bars at the start of the campaign. Methanol (2 kg) is dispensed into the feed mix tank with liner and warmed to 40° C. Approximately 3700 grams of poloxamer 188 is added to the feed tank and stirred until completely mixed. 5100 grams of the mixed solution is pumped into the extractor. The $CO_2$ flow rate is maintained at 390 gm/min. Two (2) successive extractions are performed by adjusting the methanol concentration. Extraction is conducted for 12 hours±30 minutes at 7.6% MeOH/$CO_2$ with a methanol flow rate of 27.6±1.0 gm/min. Extraction is continued for 12 hours±15 minutes at 8.6% MeOH/$CO_2$ at a methanol flow rate of 36.6±1.0 gm/min.

After the 24-hr purification, the extractor is discharged through the rapid depressurization system (Particle from Gas Saturated Solutions (PGSS)) and the wet product is collected in the liners. A sample of wet product (~600 gm) is transferred to a flask and dried using a rotary evaporator for approximately 3 hours at room temperature and moderate vacuum, followed by 30 minutes at room temperature and high vacuum and 30 additional minutes at 35° C. The dried product is collected and tested by Gel Permeation Chromatography (GPC) for molecular weight distribution. No low molecular weight (LMW) components are detected in the purified product. The purified product contained approximately 4.5% high molecular weight (HMW) components.

Example 5

Batch Process Purification of Poloxamer 188 by Extraction with Methanol/Supercritical $CO_2$ Cosolvent A batch process purification of poloxamer 188 by extraction with a methanol/supercritical $CO_2$ cosolvent was evaluated. Poloxamer 188 (Asahi Denka Kogyo, Japan) was purified by adjusting the solvent characteristics by controlling the extraction solvent temperature, pressure and methanol co-solvent content. The processes differed in the pressure and the co-solvent content.

Poloxamer 188 (13-14 kg) was mixed with methanol solvent in a high pressure extraction vessel. A co-solvent of methanol and supercritical $CO_2$ (BOC gases, USA) was mixed and pumped through the extraction vessel. The extraction was started with a lower methanol concentration that was successively increased while monitoring the composition of the fraction removed during the extraction. The average methanol concentration was 7.3% (by weight). The concentration was increased stepwise from 6.6% to 7.6% to 8.6%. The extraction vessel pressure was 300±15 bars. The methanol/supercritical $CO_2$ solvent temperature and extractor jacket temperature were 40±5° C. The extraction temperature was adjusted to 35-45° C. The eluted fractions were analyzed by Gel Permeation Chromatography (GPC). The molecular weight distribution of the purified poloxamer 188 recovered from the extraction vessel was narrower than for the starting material.

The resulting yield was approximately 75%. The peak average molecular weight was approximately 9,000 Daltons. Low molecular weight components (less than 4,500 Daltons) were approximately 1.0%. Polydispersity was approximately 1.

Example 6

12-L Scale Multi-Step Extraction Batch Process Purification of Poloxamer 188 and Analysis by Gel Permeation Chromatography (GPC)

A. Supercritical Fluid Extraction (SFE) Method

Four batches of poloxamer 188 were purified by SFE Batch Process in a 12 liter extraction vessel. Each batch was purified as described below. The system was pressurized with $CO_2$ and the pressure was maintained above 900 psig (63 bars) between batches. Methanol (2000±20 gm) was dispensed into the feed mix tank with liner and warmed to 40° C. Poloxamer 188 (3696±20 gm) was dispensed into the feed tank and stirred until mixed. Ninety percent (90%) of the poloxamer 188 solution was pumped into the extractor, and the system was pressurized to 310±15 bars. The $CO_2$ flow rate was maintained at 390 gm/min. Three (3) successive extractions were performed by adjusting the methanol concentration with a controlled stepwise increase through 6.6 weight %, 7.6 weight % or 8.6 weight %. At each methanol concentration, extraction was conducted for a defined time period as described in Table 15. In-process samples were collected from the bottom of the extractor after the designated times during each extraction.

TABLE 15

Extraction conditions for multi-step purification of poloxamer 188.

| Extraction | Time (hours) | In-process sample collection times (hr) | $CO_2$ flow rate (gm/min) | Methanol flow rate (gm/min) | Percent methanol in $CO_2$ |
|---|---|---|---|---|---|
| 1 | 12 (±0.5) | 4, 8 and 12 | 390 | 27.6 (±1.0) | 6.6% |
| 2 | 10 (±0.5) | 3, 6 and 10 | 390 | 32.1 (±1.0) | 7.6% |
| 3 | 4 (±0.25) | 2 and 4 | 390 | 36.6 (±1.0) | 8.6% |

At the end of the 26-hour purification process, the extractor was discharged through the rapid depressurization system and the wet product was collected in the liners. A sub-lot of wet product (~600 g) was transferred to a flask and dried using a rotary evaporator for approximately 3 hours at room temperature and moderate vacuum, followed by 30 minutes at room temperature and high vacuum and an additional 30 minutes at 35° C. and high vacuum. The dried product was collected as a sub-lot. This drying process was repeated with the remaining wet product to make 3 sub-lots of dried product. The 3 sub-lots were combined in a 10 L drum and mixed for 30 minutes to produce purified poloxamer 188. The yield per feed was approximately 55%.

B. Characterization of Purified Product

The starting and purified poloxamer 188 products were assessed by Gel Permeation Chromatography (GPC). The results are set forth in FIG. 6A-6B.

Figure 6A:
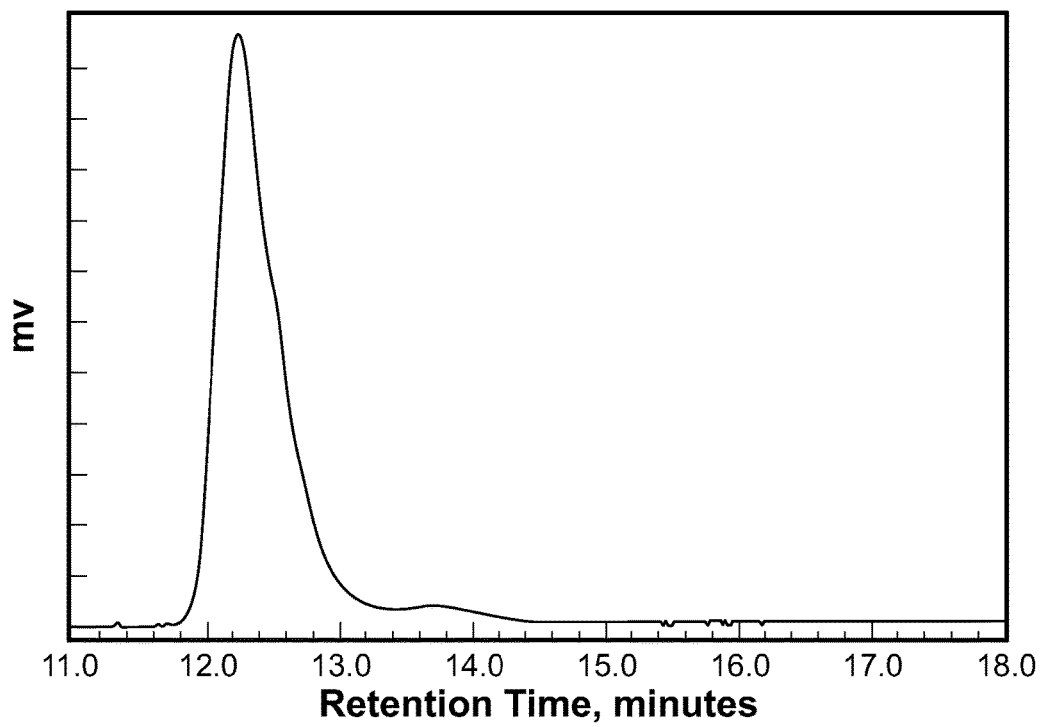
FIG. 6A shows a gel permeation chromatography (GPC) of low molecular weight substance content in a commercially available poloxamer 188.

FIG. 6A shows that GPC profile of the starting poloxamer 188. In the GPC trace, retention time is plotted against relative amounts of different molecular weight species. Increasing retention time on the x-axis corresponds to decreasing molecular weight. The GPC trace of the starting poloxamer 188 shows a narrow molecular weight distribution with a small additional peak at the low molecular weight side. The area under the curve for the low molecular weight component is approximately 4-7%, with an average molecular weight of less than 4,500 Daltons.

Figure 6B:
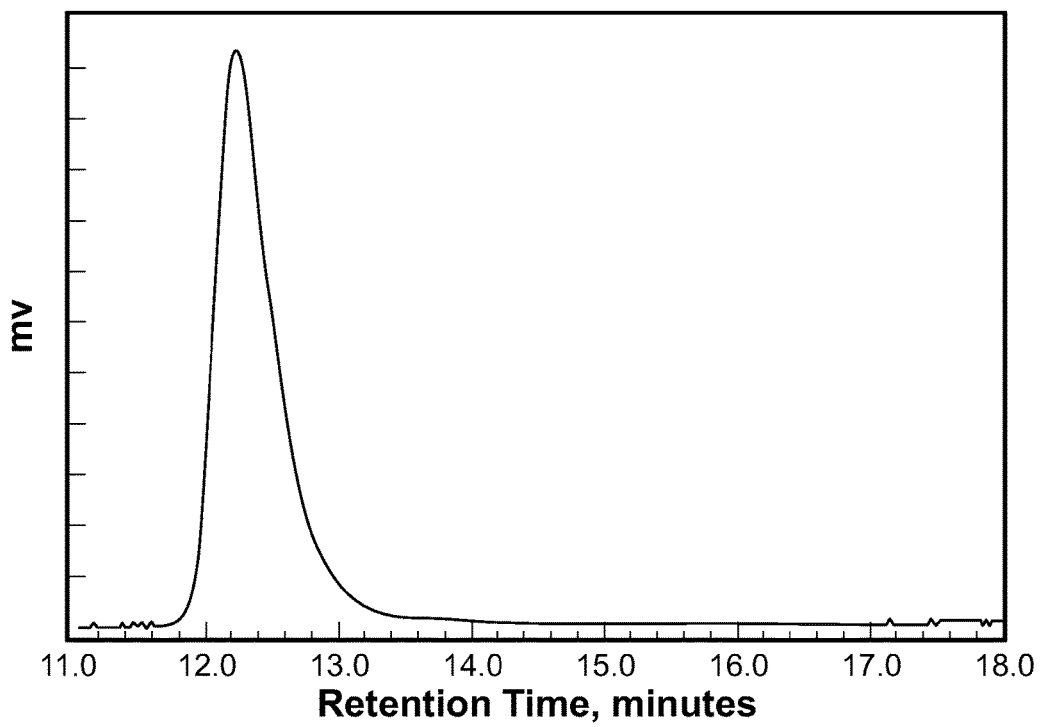
FIG. 6B shows a gel permeation chromatography (GPC) of low molecular weight substance content in a poloxamer 188 material purified according to an embodiment provided herein.

FIG. 6B shows the GPC profile for the purified poloxamer 188. The purified poloxamer 188 has a narrower molecular weight distribution than the commercially available poloxamer 188. In comparison, the GPC trace of the purified poloxamer 188 shows a narrow molecular weight distribution with significantly smaller amounts of low molecular weight peak (less than 1.5% of the area of the main peak).

Example 7

Preparation and Administration of Long Circulating Material Free (LCMF) Poloxamer 188

A. Supercritical Fluid Extraction (SFE) Process

A multi-step extraction batch process of poloxamer 188 was performed with extraction conducted at a pressure of 247±15 atm (approximately 200-260 bars) and a controlled step-wise increase of methanol of 7.4, 9.1 and 10.7 weight % methanol. Before purification, the poloxamer 188 raw material (BASF Corporation, Washington, N.J.) was characterized by Gel Permeation Chromatography (GPC). Molecular weight analysis demonstrated that raw material had an average molecular weight of the main peak of about 8,500±750 Da, no more than 6.0% low molecular weight (LMW) species of less than 4,500 Da and no more than 1% high molecular weight species (HMW) greater than 13,000 Da. In addition, the polydispersity was no more than 1.2.

A 50-L, high pressure, stainless steel, extractor vessel was charged with 14 kg of commercial grade poloxamer 188 (BASF Corporation, Washington, N.J.) and 7 kg of methanol, pressurized with $CO_2$ (49±10 atm, i.e. 720±147 psi) (Messer France, S.A.S., Lavera, France) and heated to 35° C. to 50° C. for 40-80 minutes until a homogenous solution was obtained. $CO_2$ (supplied either from a main supply tank or via recycling through an extraction system), was cooled in a heat exchanger and fed into a temperature-controlled, high pressure, stainless steel, solvent reservoir. A high-pressure pump increased the pressure of liquid $CO_2$ to the desired extraction pressure. The high pressure $CO_2$ stream was heated to the process temperature by a second heat exchanger. Methanol (Merck KGaA, Darmstadt, Germany) was fed from a main supply tank into the $CO_2$ solvent stream to produce the extraction methanol/$CO_2$ cosolvent, which was fed through inlet systems into the extractor vessel as a fine mist at a pressure of 247±15 atm (3600±psi) or 240 to 260 bars and a temperature of 40° C.

A 7.4% methanol/$CO_2$ extraction cosolvent was percolated through the poloxamer solution for 3 hours at a methanol flow rate typically at 8 kg/hr (range 6.8 kg/hr to 9.2 kg/hr; 108 kg/hr total flow rate). The extraction continued with a 9.1% methanol/$CO_2$ co-solvent for 4 more hours at a methanol flow rate typically at 10 kg/hour (range of 8.5 kg/hr to 11.5 kg/hr; 110 kg/hr total flow rate). The extraction further continued with a 10.7% methanol/$CO_2$ cosolvent for 8 more hours at a methanol flow rate typically at 12 kg per hour (range of 10.2 kg/hr to 13.8 kg/hr; 112 kg/hr total flow rate). Throughout the extraction process, extraction of soluble species were continuously extracted from the top of the extractor. The extraction solvent was removed from the top of the extractor and passed through two high pressure, stainless steel, cyclone separators arranged in series to reduce system pressure from 247 atm (3600 psi) to 59 atm (870 psi) and then from 59 atm to 49 atm (720 psi) and to separate $CO_2$ from the methanolic stream. The separated $CO_2$ was condensed, passed through the heat exchanger and stored in the solvent reservoir. Pressure of the methanol waste stream was further reduced by passing through another cyclone separator. The purified poloxamer 188 remained in the extractor.

After extraction, the purified poloxamer 188 solution was discharged from the bottom of the extractor into a mixer/dryer unit equipped with a stirrer. The poloxamer 188 product was precipitated under reduced pressure via a Particle from Gas Saturated Solutions (PGSS) technique. The precipitate contained approximately 20% to 35% methanol. The purified poloxamer 188 was dried under vacuum at not more than 40 or 45° C. to remove residual methanol. The feed yield of the product gave an average yield of 65%.

Molecular weight analysis of the purified product as determined by GPC demonstrated that the purified product met the acceptance specifications. There was an average molecular weight of the main peak of about 8,500±750 Da and an average molecular weight average of 8,500±750 Da, no more than 1.5% low molecular weight (LMW) species of less than 4,500 Da and no more than 1.5% high molecular weight species (HMW) greater than 13,000 Da. In addition, the polydispersity was no more than 1.05. Thus, the results showed that the procedures resulted in a measurable reduction in the LMW species, and an improvement in the polydispersity of the purified product.

The resulting purified poloxamer 188 was formulated into a clear, colorless, sterile, non-pyrogenic, aqueous solution containing the purified poloxamer at 150 mg/ml, sodium chloride at 3.08 mg/ml, sodium citrate (dihydrate) at 2.38 mg/ml, and citric acid anhydrous at 0.366 mg/ml in water for injection. The solution was sterile filtered and filled into 100 ml glass vials, covered with a nitrogen blanket, and closed with a butyl rubber stopper and aluminum overseal. The resulting osmolarity of the solution was approximately 312 mOsm/L. The LCMF poloxamer-188 composition did not contain any bacteriostatic agents or preservatives.

B. Characterization of the Plasma Concentration Time Course Following Intravenous Administration of Purified (LCMF) Poloxamer 188 Using HPLC-GPC (Method 1)

Purified LCMF poloxamer 188 generated as described above was administered intravenously to 62 healthy volunteers as part of assessment to determine its effect on the QT/QTc interval. Eight of the 62 subjects were randomly selected for quantitative analysis of the plasma poloxamer levels using an HPLC-GPC method. Following administration, blood samples were obtained by venipuncture into heparin anti-coagulated tubes at baseline, during drug administration (hours 1, 2, 3, 4, 5, and 6) and post administration at hours 1, 1.5, 2, 2.5, 5, 6, and 18. Plasma was separated by centrifugation and stored frozen until analysis. The purified poloxamer 188 was administered as either a high dose of a loading dose of 300 mg/kg/hr for one hour followed by a maintenance dose of 200 mg/kg/hr for 5 hours or a lower dose of 100 mg/kg for 1 hour followed by 30 mg/kg/hr for 5 hours. A mean maximum concentration (Cmax) of the administered purified poloxamer 188 of 0.9 mg/mL was attained by the end of the one hour loading infusion. The mean concentration at steady state (Css) was about 0.4 mg/ml was attained during maintenance infusion. The plasma concentration declined rapidly following discontinuation of the maintenance infusion. The LCMF product purified as described above did not demonstrate the long circulating higher molecular weight material, observed with prior poloxamer 188 and as defined herein, in the plasma.

Figure 7A:
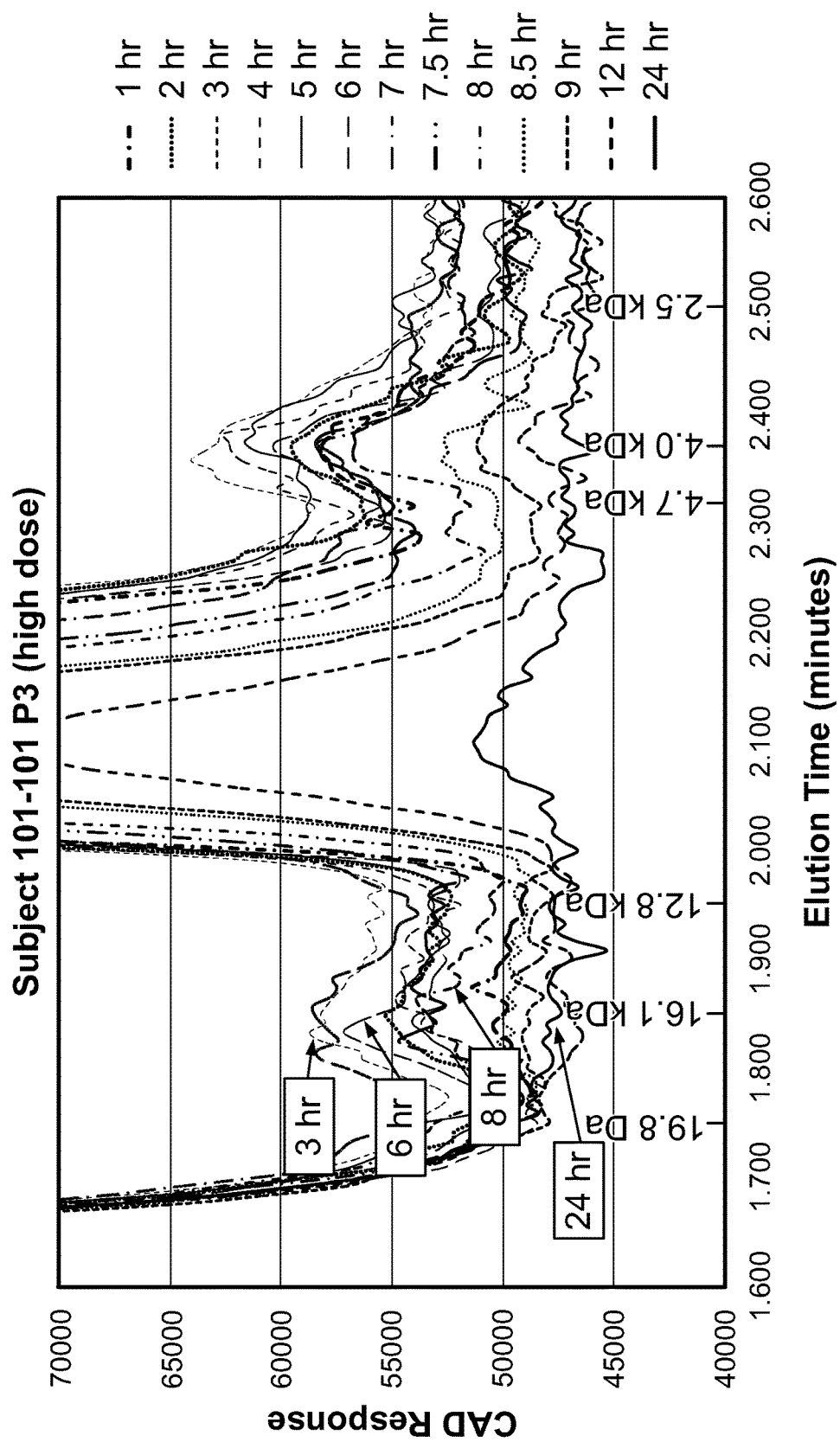
FIG. 7A shows serial HPLC-GPC of plasma obtained at all time points following administration of the purified LCMF poloxamer 188 for a single subject.
Figure 7B:
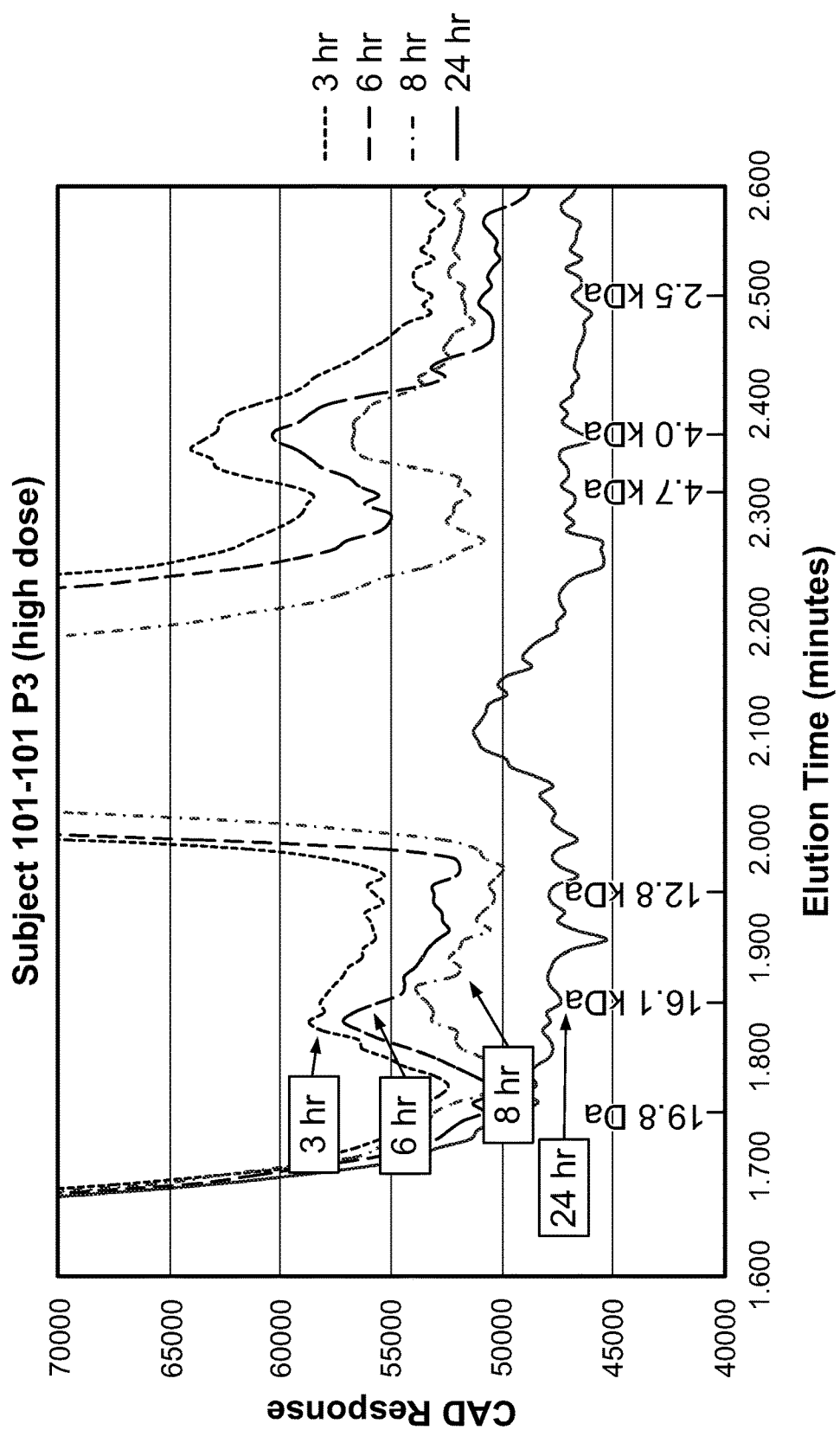
FIG. 7B shows serial HPLC-GPC of plasma obtained at 3 hour, 6 hour, 8 hour and 24 hour time points following administration of the purified LCMF poloxamer 188 for a single subject.

To confirm the absence of such long circulating material in plasma, plasma from subjects receiving the higher dose were similarly studied using HPLC-GPC. FIGS. 7A and 7B show serial HPLC-GPC of plasma obtained at various time points following administration of the purified LCMF poloxamer 188 for a single subject. FIG. 7A shows the chromatograms at all time points, while FIG. 7B shows selected time points for comparison. In both figures, the chromatogram is enlarged to show the high molecular weight portion (19.8 K Daltons-12.4 K Daltons) of the polymeric distribution. Also shown are the main peak portion (12.8-4.7 K Da) and the lower molecular weight portion (4.7-2.5 K Da). The HPLC-GPC method quantifies plasma levels based on the height of the eluting peak relative to standards of known concentration (i.e. the higher the eluting peak, the higher the plasma level). The GPC method also identifies the molecular weight range by comparison of the sample elution time to that of standards of known molecular weight.

The chromatograms show that over time the high molecular weight portion of the poloxamer 188 polymeric distribution declines in relative proportion to the main peak and lower molecular weight components. Thus, the polymeric distribution shows that the high molecular weight portion clears from the circulation in a substantially uniform manner. The results also show that the higher molecular weight species do not exhibit a longer circulating half-life (relative to the other polymeric components) and do not accumulate in the circulation following intravenous administration.

C. Comparison of the Plasma Concentration Time Course Following Intravenous Administration of Purified LCMF Poloxamer 188 and Purified LCM-Containing Poloxamer 188 by HPLC-GPC 1. Administration of the Long Circulating Material (LCM)-Containing Poloxamer 188

The (LCM-containing) purified poloxamer 188 was administered to 6 healthy volunteers as an intravenous loading dose of 100 mg/kg/hr for one hour followed by 30 mg/kg/hr for 48 hours as part of a safety and pharmacokinetics study (Grindel et al). Blood samples were obtained by venipuncture into EDTA anticoagulated tubes prior to drug administration (baseline), during administration (at 1 hour, 6 hours, 12 hours 18 hour 24 hours 36 and 48 hours) and at 30 minutes, 1 hour, 1.5 hours, 2 hours, 4 hours, 6 hours, 8 hours, 12 hours, 14 hours, 20 hours and 24 hours post drug administration. Plasma was separated and stored frozen until analysis using an HPLC-GPC method. Analysis of the plasma samples revealed the clearance kinetics of the main peak and the HMW peak for the (LCM-containing) purified poloxamer 188 a. HMW Peak (the Long Circulating Material)

Following administration at the above dose, the HMW component (detected in the HPLC-GPC assay as a peak of approximately 16,000 Daltons) was accumulating during the drug administration period and did not reach its mean Cmax concentration of 225 µg/ml (n=6) until 2 hours after the end of drug administration. By 6 hours after discontinuation of infusion, mean plasma levels remained at 202 ug/ml, a concentration that had declined by only about 10% from the Cmax value. Over the 24 hour post infusion blood collection period, mean plasma levels only declined by 22.5% to a plasma concentration of 165 µg/ml. Based on these changes in the plasma concentration time course an elimination half-life of >48 hours is estimated.

b. Main Peak

Following administration at the dose above, the main peak achieved an apparent mean steady state concentration of 522 µg/ml (n=6) that was maintained during drug infusion. One hour after discontinuation of infusion, plasma levels dropped from the steady state concentration by 52% to 255 µg/ml. By 6 hours after discontinuation, plasma levels had dropped by 85% to 81 µg/ml. By 24 hours post infusion, plasma levels declined by 96% to a plasma concentration of about 19 µg/ml (n=6). Based on these changes in the plasma concentration time course the half-life is estimated to be about 5 hours.

2. LCMF Poloxamer 188 (Prepared as Described Above)

LCMF poloxamer was administered to 62 healthy volunteers at a dose of 300 mg/kg for one hour followed by 200 mg/kg/hr for 5 hours as part of the assessment to determine its effect on the QT/QTc interval as previously described. Eight of the 62 subjects were randomly selected for quantitative analysis of the plasma poloxamer levels using a similar HPLC-GPC method as described in part (B) above but with improved linearity at lower plasma levels.

a. HMW Peak

Following administration at the above dose, the HMW component, which was detected in the HPLC-GPC assay as a peak of approximately 16,000 Daltons, accumulated to a small extent during drug administration, and achieved its Cmax (mean value of 117 µg/ml, n=8) by end infusion. By 1 hour after discontinuation of drug administration, plasma levels had declined by 27% from the Cmax value to 86 µg/ml. By 6 hours after the end of drug administration, mean plasma levels had declined by 71% from the Cmax value to 34 µg/ml. By 18 hours after the end of infusion, the mean plasma level had declined by 82% to a concentration of 19 µg/ml (n=8). Based on these changes in the plasma concentration over time, the elimination half-life for the HMW component was estimated to be between 6-9 hours.

b. Main Peak

Following administration at the dose above, the main peak achieved an apparent mean steady state concentration of 2,637 µg/ml that was maintained during the 6 hour infusion period (n=8). One hour after discontinuation of infusion, mean plasma levels had decreased from steady state by 67% to 872 µg/ml and by 6 hours after discontinuation, mean plasma levels had declined by 93% (from steady state) to 184 µg/ml. By 18 hours after discontinuation of infusion, mean plasma levels declined by over 98% (from steady state) to a plasma concentration of about 34 µg/ml (n=6). Based on these changes in the plasma concentration time course, the elimination half-life is estimated to be about 3 hours.

c. Summary Comparison Table

A comparison of the relative rates of clearance from the plasma at similar time points following administration is shown in Table 16 below. The data demonstrate a marked difference in the rate of decline in plasma concentration between (LCM-containing) purified poloxamer 188 and the LCMF poloxamer 188, demonstrating that LCMF poloxamer 188 clears faster. The difference is apparent for the HMW peak and for the main peak. The difference is most apparent for the HMW peak. This shows that the LCMF poloxamer is different from the LCM-containing poloxamer of the prior art.

TABLE 16

|  | HMW Peak | | Main Peak | |
| --- | --- | --- | --- | --- |
|  | LCMF | (LCM-containing) purified poloxamer 188 | LCMF | (LCM-containing) purified poloxamer 188 |
| % decrease 1 hr | 27 | 0 | 67 | 52 |
|  | 71 | 10 | 93 | 85 |
| Apparent elimination t½ | 6-9 hours | >48 hours | About 3 hours | About 5 hours |

D. Analytical Data Confirming that Purified LCMF Poloxamer 188 is Different from Purified Poloxamer 188 Containing LCM 1. Analytical Test (RP-HPLC Assay) to Compare Various Poloxamers In reversed phase chromatography there is a hydrophobic stationary phase (the column) and a more polar mobile phase. Because of this "reversed" phase condition, RP-HPLC is commonly used to separate compounds based on relative hydrophobicity. More hydrophobic compounds exhibit a longer column retention time compared to more hydrophilic compounds.

The following HPLC conditions were used to compare column retention times for various poloxamers with known differences in their hydrophilic/lipophilic balance (HLB), along with purified poloxamer 188 containing LCM and the LCMF poloxamer 188:

| Column | Xterra RP18, 3.5 um, 4.6 × 100 mm |
| --- | --- |
| Mobile Phase | A: 0.1% HOAc in Water |
|  | B: Acetonitrile |
| Gradient | Time | % B |

| Time | % B |
| --- | --- |
| 0 | 50 |
| 1.0 | 50 |
| 15.0 | 90 |
| 16.0 | 90 |
| 16.1 | 50 |
| 20.0 | 50 |

| Flow Rate | 0.50 ml/min |
| --- | --- |
| Column Temp | 40° C. |
| ELS*Detection | $N_2$: 0.5 liter/minute, Nebulizer: 75° C., Evaporator: 75° C. |
| Sample Preparation | Drug Product - No dilution Purified Poloxamer 188, 150 mg/mL in 10 mM NaCitrate pH 6 |
| Injection Volume | 10 µL |

*ELS = evaporative light scattering

Results

The results show that the LCMF poloxamer 188 is different from the prior art purified poloxamer 188. It has different pharmacokinetic properties, which reflect that it is more hydrophilic than the prior art material that contains the longer circulating material.

Figure 9:
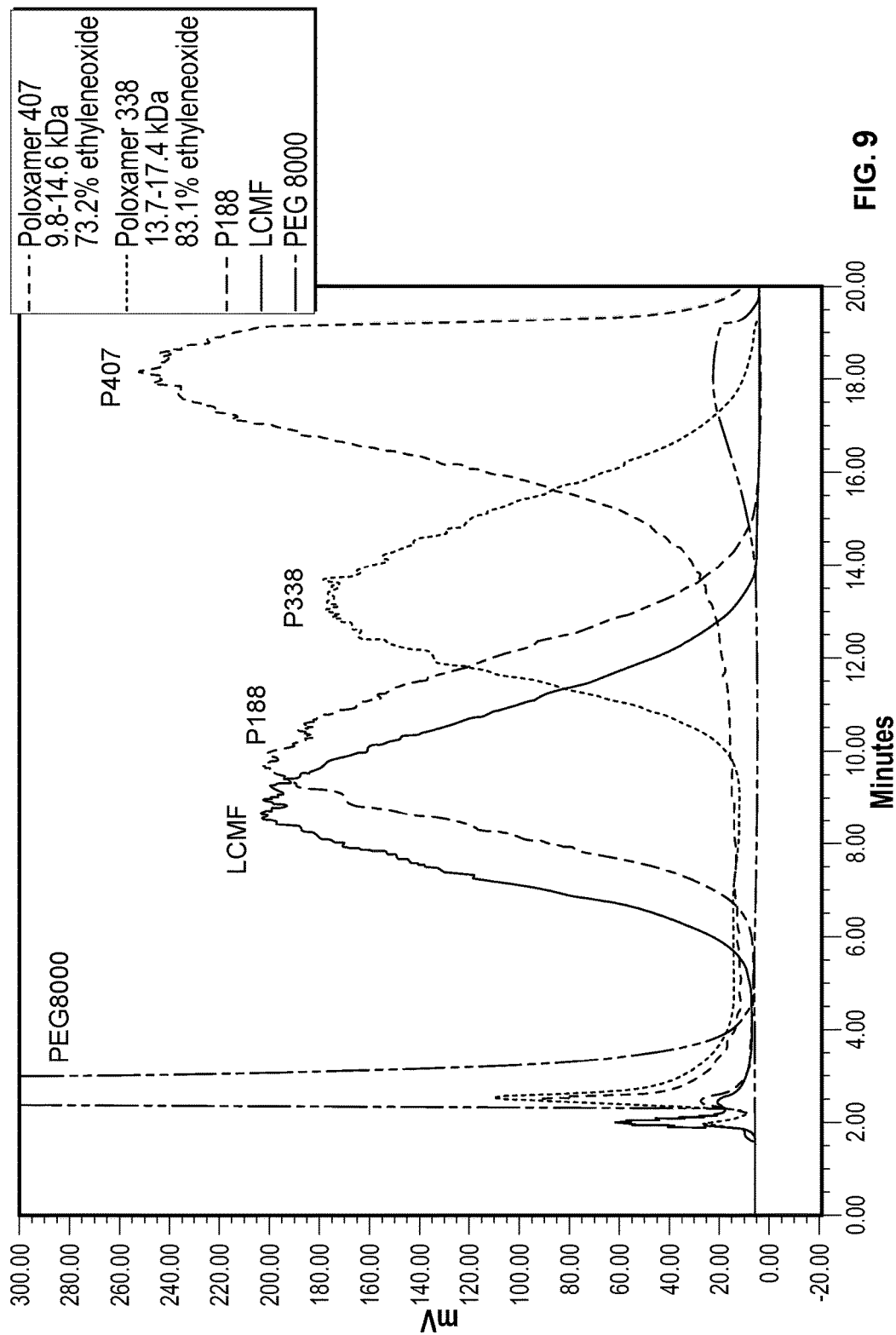
FIG. 9 shows a Reverse Phase High Performance Liquid Chromatography (RP-HPLC) chromatogram comparing profiles of compositions of 15% LCMF 188 with 15% P188 (available under the trademark Flocor®), relative to other poloxamers and polymers (of different hydrophobicity/hydrophilicity) showing that the LCMF 188 is more hydrophilic than the P188.

FIG. 9 shows the RP-HPLC chromatograms for a highly hydrophilic polymer (PEG 8000), the LCMF poloxamer 188, the LCM-containing purified poloxamer 188, and two poloxamers with decreasing HLB values (increasing hydrophobicity), Poloxamer 338 and Poloxamer 407, respectively. The most hydrophilic polymer, PEG 8000, exhibits little retention on the column consistent with its highly hydrophilic nature. Poloxamer 338 (HLB>24) and Poloxamer 407 (HLB 18-23) exhibit far longer retention times (add the $t_R$ and k' values) in accord with their known HLB values. The LCMF purified poloxamer 188 elutes more quickly than the LCM-containing purified poloxamer 188, (the average $t_R$ and k' for LCMF purified poloxamer is about 8.8 (8.807) and about 3.2 (3.202), respectively, compared to about 10.0 (9.883) and 3.7 (3.697) for LCM containing purified poloxamer) indicating that the LCMF poloxamer 188 is relatively more hydrophilic than the LCM containing purified poloxamer 188.

Figure 10:
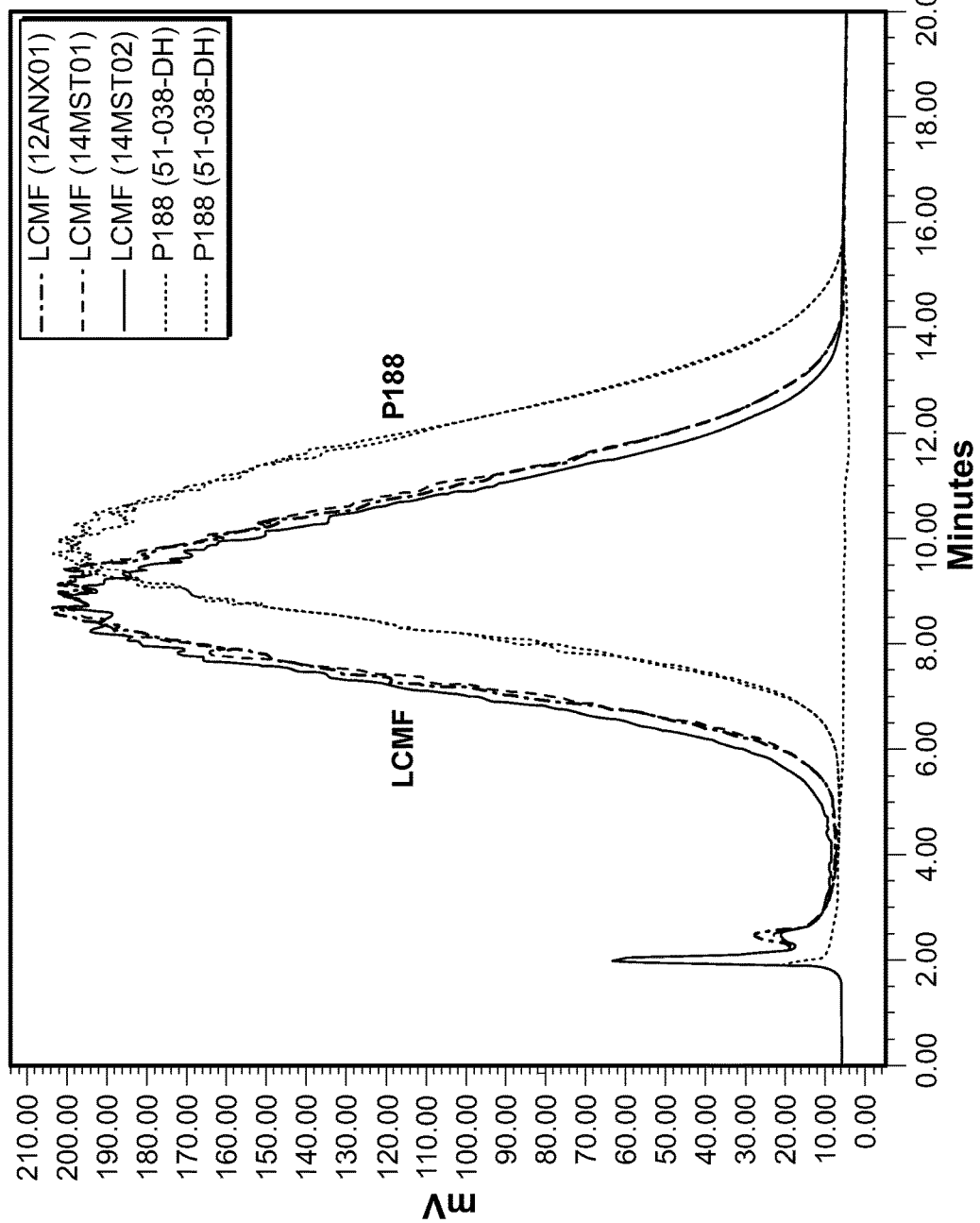
FIG. 10 shows a RP-HPLC chromatogram comparing different lots of LCMF poloxamer 188 with purified poloxamer 188 confirming the difference in hydrophilicity.

FIG. 10 shows the chromatograms for 3 different lots of purified LCMF poloxamer 188 and two (2) different lots of purified (LCM-containing) poloxamer 188. These results demonstrate a robust reproducibility for the different lots of materials, and show that the difference between the two materials cannot be accounted for by assay variability. These results demonstrate that the polymeric distribution of LCMF poloxamer 188 is more hydrophilic than purified poloxamer 188.

2. The Different Pharmacokinetic Behavior of the LCMF Purified Poloxamer and the LCM-Containing Poloxamer Correlate with the Differences in their Hydrophilicity As described herein (see, e.g., Example 7B, above, and FIGS. 9-10) and TABLE 1), the LCMF poloxamer 188 exhibits a markedly different pharmacokinetic behavior following administration to human subjects when compared to purified poloxamer 188, which contains the long circulating material (LCM) following in vivo administration. The data provided in this example indicate that LCMF poloxamer 188 is more hydrophilic compared to purified poloxamer 188 that gives rise to the long circulating material.

The polymeric size distribution of purified variants of poloxamer 188 purified LCM-containing poloxamer 188, and the LCMF poloxamer 188 is similar with regard to size as shown by HPLC-GPC. Both meet the criteria:

| Test Attribute | Acceptance Criteria | Test Method |
|---|---|---|
| Molecular Weight Analysis | | |
| Peak MW | 8500 ± 750 Da | HPLC-GPC |
| Weight Average MW | 8500 ± 750 Da | |
| % LMW (<4500 Da) | NMT* 1.5% | |
| % HMW (>13000 Da) | NMT 1.5% | |
| Polydispersity | NMT 1.05 | |

*NMT = Not More Than

While the polymeric size distribution, as shown by HPLC-GPC, of both purified poloxamers is similar, as demonstrated by the RP-HPLC herein, the molecules that comprise the polymeric distribution of LCMF poloxamer 188 are more hydrophilic.

When injected into an animal, a more hydrophilic polymeric distribution clears from the circulation at a faster rate. This accounts for the decreased presence of a longer circulating material in the LCMF poloxamer 188 preparation. The results also indicate that, as observed and described above, the main peak of the polymeric distribution clears faster. For example, the plasma concentration time course data from a clinical trial show a shorter elimination half-life for the main peak and the high molecular weight peak of the LCMF poloxamer 188 compared to the purified poloxamer 188 containing LCM.

Since the rheologic, cytoprotective, anti-adhesive and antithrombotic effects of P188 are optimal within the predominant or main copolymers of the distribution, which are approximately 8,400 to 9,400 Daltons (which have a circulating half life of about 4-7 hours), the presence of larger, more hydrophobic, longer circulating half-life components of poloxamer 188 is not desirable. For example, among the desired activities of P188 is its rheologic effect to reduce blood viscosity and inhibit red blood cell (RBC) aggregation, which account for its ability to improve blood flow in damaged tissues. In contrast, more hydrophobic, higher molecular weight poloxamers such as P338 (also called Pluronic® F108) and P308 (Pluronic® F98), increase blood viscosity and RBC aggregation (Armstrong et al. (2001) *Biorheology*, 38:239-247). This is the opposite effect of P188 and indicates that higher molecular weight, hydrophobic poloxamer species can have undesirable biological effects.

The results, thus, indicate that the hydrophobic components contained in the high molecular weight peak of purified (LCM-containing) poloxamer 188 are an unwanted impurity. Thus a poloxamer 188, such as LCMF poloxamer 188 with a reduced amount of these components, is desirable.

Example 8

Effect of Adjusting the Methanol Concentration in a Multi-Step Extraction Batch Process Employing a Controlled Step-Wise Increase of Methanol The method substantially as described in the Example above was performed, except the multi-step extraction batch process of poloxamer 188 was performed with extraction conducted by altering the methanol concentrations in the controlled step-wise increase of methanol as follows. The maximum pressure that is feasible is typically 250 atm. Thus, processes to adjust the methanol concentration and extraction time can be employed to accommodate the pressure limitation.

A. Controlled Stepwise Increase: 6.3, 7.1 and 8.1 Weight % Methanol

Poloxamer 188 (14 kg) was purified as described in Example 8, except that a 6.3% methanol/$CO_2$ extraction cosolvent was percolated through the poloxamer solution for 3 hours at a methanol flow rate of 107 kg/hr. The extraction continued with a 7.1% methanol/$CO_2$ cosolvent for 8 more hours at a methanol flow rate of 108 kg/hr. The extraction further continued with an 8.1% methanol/$CO_2$ cosolvent for 7 more hours at a methanol flow rate of 109 kg/hr. At the end of the process, the extractor contents were discharged and dried to remove residual methanol as described in part A. The yield of the purified poloxamer 188 was 66%. The results also demonstrated that the process resulted in a measurable reduction in the LMW species.

B. Controlled Stepwise Increase: 3.8, 9.1 and 10.7 Weight % Methanol

Poloxamer 188 (14 kg) was purified as described in Example 8, except that a 3.8% methanol/$CO_2$ extraction co-solvent was percolated through the poloxamer solution for 4 hours at a methanol flow rate of 104 kg/hr. The extraction continued with a 9.1% methanol/$CO_2$ cosolvent for 3 more hours at a methanol flow rate of 108 kg/hr. The extraction further continued with a 10.7% methanol/$CO_2$ cosolvent for 8 more hours at a methanol flow rate of 112 kg/hr. At the end of the process, the extractor contents were discharged and dried to remove residual methanol as described in part A. The yield of the purified poloxamer 188 was 57%. The results also demonstrated that the process resulted in a measurable reduction in the LMW species.

Example 9

Batch Process Purification of Poloxamer 188 by Extraction with Methanol/High Pressure $CO_2$ Co-Solvent A batch process purification of poloxamer 188 by extraction with a methanol/high pressure $CO_2$ cosolvent is evaluated. Poloxamer 188 (13-14 kg) is purified by extraction with a methanol/high pressure $CO_2$ solvent. Poloxamer 188 is stirred with methanol in a high pressure extraction vessel until mixed. A co-solvent of methanol and high pressure $CO_2$ is pumped through the extraction vessel. The solvent characteristics of the extraction solvent are adjusted by controlling the extraction solvent temperature, pressure and the amount of methanol co-solvent. Specifically, the combination of these three parameters are selected for removal of low molecular weight (LMW) and high molecular weight (HMW) components from the commercial-grade poloxamer 188. The starting concentration of methanol is approximately 2.5 wt % and is successively increased in increments up to 25 wt %. The Extraction vessel pressure is 75±10 bars, and the extraction temperature, methanol/$CO_2$ co-solvent temperature and extractor jacket temperature is 20-25° C. The extraction process is done in a sequential fashion to successively remove various components from the extractor.

The Extraction solvent is removed and eluted fractions were analyzed by Gel Permeation Chromatography (GPC). After purification, the purified poloxamer 188 is recovered from the extraction vessel and analyzed by GPC. Initially, low molecular weight (LMW) components are removed during extraction and the main fraction is removed at higher concentrations of methanol. High molecular weight components are removed at the later stages of the extraction process. The molecular weight distribution of the purified poloxamer 188 is narrower than for the starting material.

The yield of the polymer is estimated to be 60 to 80% with less than 1.5% low molecular weight components (less than 4,500 Daltons). The peak average molecular weight is about 8,500±750 Daltons.

Since modifications will be apparent to those of skill in this art, it is intended that this invention be limited only by the scope of the appended claims.

What is claimed is:

1. A long circulating material free (LCMF) poloxamer 188, wherein:
   the LCMF poloxamer 188 is a polyoxyethylene/polyoxypropylene copolymer that has the formula $HO(CH_2CH_2O)_{a'}$—$[CH(CH_3)CH_2O]_b$—$(CH_2CH_2O)_a$ H, wherein:
   each of a and a' is an integer such that the percentage of the hydrophile ($C_2H_4O$) is between approximately 60% and 90% by weight of the total molecular weight of the copolymer;
   a and a' are the same or different;
   b is an integer such that the molecular weight of the hydrophobe ($C_3H_6O$) is between approximately 1,300 and 2,300 Daltons;
   no more than 1.5% of the total components in the polymeric distribution of the co-polymer are low molecular weight components having an average molecular weight of less than 4,500 Daltons;
   no more than 1.5% of the total components in the polymeric distribution of the co-polymer are high molecular weight components having an average molecular weight of greater than 13,000 Daltons;
   the polydispersity value of the copolymer is less than approximately 1.07 or less than 1.07; and
   following intravenous administration to a human subject, the circulating plasma half-life of any components not comprising the main peak in the distribution of copolymer is no more than 5.0-fold the circulating half-life of the main component in the distribution of the copolymer.

2. The LCMF poloxamer of claim 1, wherein all components comprising the polymeric distribution of the copolymer have a circulating half-life in the plasma of the subject that is no more than 4.0-fold, or 3.0-fold longer than the circulating half-life of the main component of the co-polymer following intravenous administration to a subject.

3. The LCMF poloxamer of claim 1, wherein all components in the distribution of the copolymer, when administered to a human subject, have a circulating half-life in the plasma of the subject that is no more than 3-fold longer than the circulating half-life of the main component in the distribution of the co-polymer.

4. The LCMF poloxamer of claim 1, wherein all components in the distribution of the copolymer, when administered to a human subject, have a half-life in the plasma of the subject that is no more than 10 or 12 hours.

5. The LCMF poloxamer of claim 1, wherein the polyoxyethylene/polyoxypropylene copolymer is a poloxamer with a hydrophobe having a molecular weight of about 1,400 to 2,000 Da or 1,400 to 2,000 Da, and a hydrophile portion constituting approximately 70% to 90% or 70% to 90% by weight of the copolymer.

6. The LCMF poloxamer of claim 1, wherein: the molecular weight of the hydrophobe ($C_3H_6O$) is about or is 1,750 Da; and the average molecular weight of the polyoxyethylene/polyoxypropylene copolymer is 7,680 to 9,510 Daltons.

7. The LCMF poloxamer of claim 6, wherein the average molecular weight of the polyoxyethylene/polyoxypropylene copolymer is 8,400-8,800 Daltons.

8. The LCMF poloxamer 188 of claim 1, wherein:
   the LCMF poloxamer 188 is a polyoxyethylene/polyoxypropylene copolymer that has the formula $HO(CH_2CH_2O)_{a'}$—$[CH(CH_3)CH_2O]_b$—$(CH_2CH_2O)_a$ H;
   each of a and a' is an integer such that the percentage of the hydrophile ($C_2H_4O$) is between approximately 60% and 90% by weight of the total molecular weight of the copolymer;
   a and a' are the same or different;
   b is an integer such that the molecular weight of the hydrophobe ($C_3H_6O$) is between approximately 1,300 and 2,300 Daltons;
   no more than 1.5% of the total components in the distribution of the co-polymer are low molecular weight components having an average molecular weight of less than 4,500 Daltons;
   no more than 1.5% of the total components in the distribution of the co-polymer are high molecular weight components having an average molecular weight of greater than 13,000 Daltons;
   the polydispersity value of the copolymer is less than approximately 1.07 or less than 1.07; and
   the LCMF poloxamer is more hydrophilic than a purified poloxamer 188 that contains the long circulating material (LCM).

9. The LCMF poloxamer 188 of claim 1, wherein:
   the LCMF poloxamer 188 is a polyoxyethylene/polyoxypropylene copolymer that has the formula —HO$(CH_2CH_2O)_{a'}$—$[CH(CH_3)CH_2O]_b$—$(CH_2CH_2O)_a$ H—;
   each of a and a' is an integer such that the percentage of the hydrophile ($C_2H_4O$) is between approximately 60% and 90% by weight of the total molecular weight of the copolymer;
   a and a' are the same or different;
   b is an integer such that the molecular weight of the hydrophobe ($C_3H_6O$) is between approximately 1,300 and 2,300 Daltons;
   no more than 1.5% of the total components in the distribution of the co-polymer are low molecular weight components having an average molecular weight of less than 4,500 Daltons;
   no more than 1.5% of the total components in the distribution of the co-polymer are high molecular weight components having an average molecular weight of greater than 13,000 Daltons;
   the polydispersity value of the copolymer is less than approximately 1.07 or less than 1.07;
   the LCMF poloxamer 188 has a mean retention time ($t_R$) as assessed by reverse phase-high performance liquid chromatography (RP-HPLC) that is shorter than purified LCM-containing poloxamer 188 under the same RP-HPLC conditions; and
   the capacity factor (k') of LCMF poloxamer 188 as assessed by RP-HPLC is less than the k' for purified LCM-containing poloxamer 188 under the same RP-HPLC conditions.

10. The LCMF poloxamer of claim 1, produced by a method comprising supercritical fluid extraction pressurized with CO2.

11. The LCMF poloxamer of claim 1, produced by a method comprising:
a) introducing a poloxamer 188 solution into an extractor vessel, wherein the poloxamer 188 is dissolved in a first alkanol to form a poloxamer 188 solution;
b) admixing the poloxamer 188 solution with an extraction solvent comprising a second alkanol and supercritical carbon dioxide under a temperature and pressure to maintain the supercritical carbon dioxide for a first defined period, wherein:
the temperature is above the critical temperature of carbon dioxide but is no more than 40° C.;
the pressure is 220 bars to 280 bars; and
the alkanol is provided at an alkanol concentration that is 7% to 8% by weight of the total extraction solvent; and
c) increasing the concentration of the second alkanol in step b) in the extraction solvent a plurality of times in gradient steps over time of the extraction method, wherein:
each plurality of times occurs for a further defined period; and in each successive step, the alkanol concentration is increased 1-2% compared to the previous concentration of the second alkanol; and
d) removing the extraction solvent from the extractor vessel to thereby remove the extracted material from the raffinate poloxamer preparation.

12. The LCMF poloxamer of claim 11, wherein:
in step a), the ratio of poloxamer to first alkanol, by weight is about or is from 2:1 to 3:1, inclusive; and
the plurality of times in step c) occurs in two, three, four or five gradient steps.

13. A pharmaceutical composition, comprising the LCMF poloxamer 188 of claim 1 in a pharmaceutically acceptable formulation.

14. A method of treating a disease or condition in a subject, comprising administering the pharmaceutical composition of claim 13 to the subject, wherein the disease or condition is selected from the group consisting of heart failure, myocardial infarction, limb ischemia, shock, stroke, ischemic stroke, sickle cell disease, neurodegenerative diseases, macular degeneration, diabetic retinopathy and congestive heart failure.

15. The method of claim 14, wherein the condition is heart failure that is acute heart failure or chronic heart failure.

16. The method of claim 14, wherein the condition is acute myocardial infarction, acute limb ischemia or acute stroke.

17. The method of claim 14, wherein the condition is sickle cell disease.

18. A composition, comprising the long circulating material free (LCMF) poloxamer 188 of claim 1, wherein:
the composition is formulated for intravenous administration; and
the composition comprises 5-50 gm of the LCMF poloxamer.

19. A composition, comprising an the LCMF poloxamer of claim 1, wherein:
the composition is formulated for intravenous administration; and
the composition comprises 5-50 gm of the LCMF poloxamer.

20. A composition comprising the LCMF poloxamer 188 of claim 1 and one or more components selected from the group consisting of blood, and blood product.

21. The composition of claim 20, wherein said one or more components is packed red blood cells or platelets.

22. A transfusion method comprising administering the composition of claim 21 to a subject, wherein:
the subject has a disease or disorder or condition selected from the group consisting of sickle cell disease, acute chest syndrome, peripheral artery disease, heart failure, stroke, peripheral vascular disease, macular degeneration, respiratory distress syndrome (ARDS), multiple organ failure, ischemia, shock, acidosis, hypothermia, anemia, trauma, blood loss and blood disorders.

23. The method of claim 22, wherein the disease, disorder or condition is selected from among hemorrhagic shock, septic shock, acute ARDS, anemic decompensation and blood loss.

24. A method of preparing the long circulating material free (LCMF) poloxamer 188 of claim 1, comprising:
a) introducing a poloxamer 188 solution into an extractor vessel, wherein the poloxamer 188 is dissolved in a first alkanol to form a poloxamer 188 solution;
b) admixing the poloxamer 188 solution with an extraction solvent comprising a second alkanol and supercritical carbon dioxide under a temperature and pressure to maintain the supercritical carbon dioxide for a first defined period, wherein:
the temperature is above the critical temperature of carbon dioxide but is no more than 40° C.;
the pressure is 220 bars to 280 bars; and
the alkanol is provided at an alkanol concentration that is 7% to 8% by weight of the total extraction solvent;
c) increasing the concentration of the second alkanol in step b) in the extraction solvent a plurality of times in gradient steps over time of the extraction method, wherein:
each plurality of times occurs for a further defined period; and
in each successive step, the alkanol concentration is increased 1-2% compared to the previous concentration of the second alkanol; and
d) removing the extraction solvent from the extractor vessel to thereby remove the extracted material from the raffinate poloxamer preparation to thereby produce the LCMF poloxamer.

25. The method of claim 24, wherein in step a), the ratio of poloxamer to first alkanol, by weight, is about or is from 2:1 to 3:1, inclusive.

26. The method claim 24, wherein step c) occurs in two steps comprising:
i) increasing the concentration of the second alkanol from about 7% to 8% to about 8.1% to 9.5% for a second defined period; and
ii) increasing the concentration of the second alkanol from about 8.2% to 9.5% to about 9.6% to 11.5% for a third defined period.

27. The method of claim 24, wherein the first defined period, second defined period and third defined period each are performed for 2 hours to 12 hours.

28. The method of claim 24, wherein: the first and second alkanol are each independently selected from the group consisting of methanol, ethanol, propanol, butanol, pentanol and a combination thereof.

29. The method of claim 24, wherein step d) of removing the extracted material occurs throughout steps b) and c).

* * * * *